United States Patent

Chandrakumar et al.

[11] Patent Number: 5,773,646
[45] Date of Patent: Jun. 30, 1998

[54] META-SUBSTITUTED PHENYLENE DERIVATIVES

[75] Inventors: Nizal Chandrakumar, Vernon Hills; Barbara B. Chen, Glenview, both of Ill.; Helen Y. Chen, Livingston, N.J.; Michael Clare, Sokie, Ill.; Alan F. Gasiecki, Vernon Hills, Ill.; Richard A. Haack, Chicago, Ill.; James W. Malecha, Libertyville, Ill.; Peter G. Ruminski, Ballwin, Mo.; Mark A. Russell, Gurnee, Ill.

[73] Assignee: G. D. Searle & Co., Chicago, Ill.

[21] Appl. No.: 825,086

[22] Filed: Mar. 27, 1997

Related U.S. Application Data

[60] Provisional application No. 60/014,464 Mar. 29, 1996.

[51] Int. Cl.$^6$ ..................... C07C 241/00; C07C 321/00; C07C 205/00; C07C 229/00

[52] U.S. Cl. ................ 562/439; 562/426; 560/9; 560/21; 560/34; 560/35; 560/37; 560/48; 548/310.7; 548/321.5

[58] Field of Search .................... 562/426, 439; 560/9, 21, 34, 35, 37, 48

[56] References Cited

U.S. PATENT DOCUMENTS 5,523,302  6/1996  Cain et al. .................. 514/252

FOREIGN PATENT DOCUMENTS

| 0 478 328 A1 | 4/1992 | European Pat. Off. ...... C07C 271/22 |
| 0 478 363 A2 | 4/1992 | European Pat. Off. ...... C07D 211/22 |
| WO 95/32710 | 12/1995 | WIPO ........................ A61K 31/18 |

*Primary Examiner*—Gary Geist
*Assistant Examiner*—Brian J. Davis
*Attorney, Agent, or Firm*—Cynthia S. Kovacevic; Roger A. Williams

[57] ABSTRACT

The present invention relates to a class of compounds represented by the Formula I

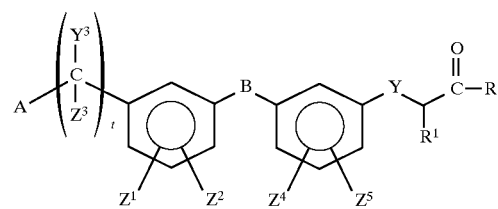

or a pharmaceutically acceptable salt thereof, pharmaceutical compositions comprising compounds of the Formula I, and methods of selectively inhibiting or antagonizing the $\alpha_v\beta_3$ integrin.

30 Claims, No Drawings

META-SUBSTITUTED PHENYLENE DERIVATIVES

This application claims the benefit of U.S. provisional application No. 60/014,464 filed Mar. 29, 1996.

FIELD OF THE INVENTION

The present invention relates to pharmaceutical agents (compounds) which are useful as $\alpha_v\beta_3$ integrin antagonists or inhibitors and as such are useful in pharmaceutical compositions and in methods for treating conditions mediated by $\alpha_v\beta_3$ by inhibiting or antagonizing $\alpha_v\beta_3$ integrins.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked $\alpha$ and $\beta$ polypeptide subunits. Currently eleven different $\alpha$ subunits have been identified and six different $\beta$ subunits have been identified. The various $\alpha$ subunits can combine with various $\beta$ subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis, Paget's disease, humoral hypercalcemia of malignancy, angiogenesis, including tumor angiogenesis, retinopathy, arthritis, including rheumatoid arthritis, periodontal disease, psoriasis and smooth muscle cell migration (e.g. restenosis). Additionally, it has been found that such agents would be useful as antivirals, antifungals and antimicrobials. Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy (Adonis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic targets for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (a loss of bone), which leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

SUMMARY OF THE INVENTION

The present invention relates to a class of compounds represented by the Formula I

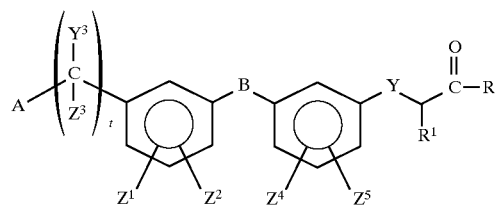

or a pharmaceutically acceptable salt thereof, wherein

A is

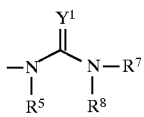

wherein $Y_1$ is selected from the group consisting of $N-R^2$, O, and S;

$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy, oxo and phenyl;

or $R^2$ taken together with $R^7$ forms a 5 membered heteroaromatic ring;

or $R^2$ taken together with $R^7$ forms a 5 membered heteroaromatic ring fused with a phenyl group optionally substituted with one or more substituent selected from the group consisting of alkoxycarbonyl and alkoxy;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; $-SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein $R^{10}$ is defined above;

or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl;

or

A is

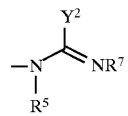

wherein $Y^2$ is selected from the group consisting of hydrogen; alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; $-S-R^9$ and $-O-R^9$ wherein $R^9$ is selected from the group consisting of H; alkyl; aralkyl; aryl; alkenyl; and alkynyl; or $R^9$ taken together with $R^7$ forms a 4–12 membered mononitrogen containing sulfur or oxygen containing heterocyclic ring; and $R^5$ and $R^7$ are as defined above;

or $Y^2$ (when $Y^2$ is carbon) taken together with $R^7$ forms a 4–12 membered mononitrogen containing ring optionally substituted with alkyl, aryl or hydroxy;

or A is selected from the group consisting of

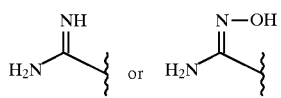

$Z^1$, $Z^2$, $Z^4$ and $Z^5$ are independently selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles; and A, wherein A is defined above;

B is selected from the group consisting of

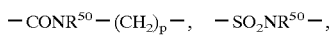

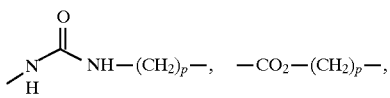

—CH$_2$CH$_2$—, alkenylene and alkynylene optionally substituted by oxo;

—CH$_2$O—;  —S—CH$_2$—;

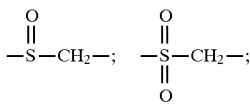

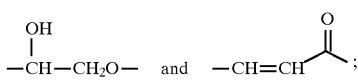

wherein p is an integer selected from the group consisting of 0, 1 and 2; wherein n is an integer selected from the group consisting of 0, 1, 2 and 3 R$^{50}$ is selected from the group consisting of H and alkyl;

Y is selected from the group consisting of

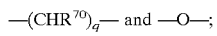

wherein q is an integer selected from the group consisting of 0 and 1; R$^{70}$ is selected from the group consisting of H, alkyl, aryl and aryl substituted with one or more substituent selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles;

t is an integer 0, 1 or 2;

R is X—R$^3$ wherein X is selected from the group consisting of O, S and NR$^4$, wherein R$^3$ and R$^4$ are independently selected from the group consisting of hydrogen; alkyl; alkenyl; alkynyl; haloalkyl; aryl; arylalkyl; sugars; steroids and in the case of the free acid, all pharmaceutically acceptable salts thereof;

or —XR$^3$ is —O— and Y is CH—Ph wherein the X—R$^3$ group is attached to the Ph of the Y group at the para position to form a lactone;

Y$^3$ and Z$^3$ are independently selected from the group consisting of H, alkyl, aryl, cycloalkyl and aralkyl;

R$^1$ is selected from the group consisting of hydrogen; alkyl; aryl;

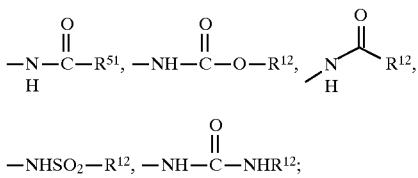

R$^{12}$ is selected from the group consisting of H, alkyl, cycloalkyl, aralkyl and aryl; and R$^{51}$ is selected from the group consisting of N-substituted pyrrolidinyl, piperidinyl and morpholinyl.

It is another object of the invention to provide pharmaceutical compositions comprising compounds of the Formula I. Such compounds and compositions are useful in selectively inhibiting or antagonizing the $\alpha_v\beta_3$ integrin and therefore in another embodiment the present invention relates to a method of selectively inhibiting or antagonizing the $\alpha_v\beta_3$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

DETAILED DESCRIPTION

The present invention relates to a class of compounds represented by the Formula I, described above.

A preferred embodiment of the present invention is a compound of the Formula II

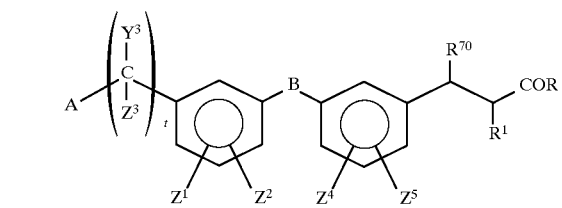

Another preferred embodiment of the present invention is a compound of the Formula III

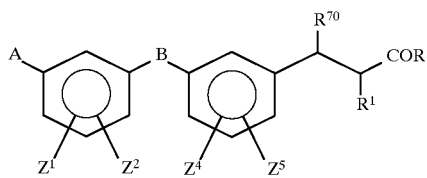

Another preferred embodiment of the present invention is a compound of the Formula III wherein B is selected from the group consisting of —CONR$^{50}$CH$_2$—; —SO$_2$NR$^{50}$; —CO$_2$CH$_2$; —CH$_2$CH$_2$—; alkenylene and alkynylene.

The invention further relates to pharmaceutical compositions containing therapeutically effective amounts of the compounds of Formulas I–III.

The invention also relates to a method of selectively inhibiting or antagonizing the $\alpha_v\beta_3$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, smooth muscle cell migration and restenosis by administering a therapeutically effective amount of a compound of the Formula I–III to achieve such inhibition together with a pharmaceutically acceptable carrier.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon—carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula

The terms "hydroxy" and "hydroxyl" as used herein are synonymous and are represented by a radical of the formula

The term "lower alkylene" or "alkylene" as used herein refers to divalent linear or branched saturated hydrocarbon radicals of 1 to about 6 carbon atoms.

As used herein the term "alkynylene" or "lower alkynylene" refers to an alkylene radical wherein at least one bond between the carbon atoms is unsaturated and such unsaturation forms a triple bond.

As used herein the term "alkenylene" or "lower alkenylene" refers to an alkylene radical wherein at least one bond between the carbon atoms is unsaturated and such unsaturation produces a double bond in cis or transconformation.

As used herein the term "alkoxy" refers to straight or branched chain oxy containing radicals of the formula —OR$^{20}$, wherein R$^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula

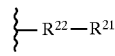

wherein
R$^{21}$ is aryl as defined above and R$^{22}$ is an alkylene as defined above. Examples of aralkyl groups include benzyl, pyridylmethyl, naphthylpropyl, phenethyl and the like.

As used herein the term "aralkoxy" or "arylakoxy" refers to a radical of the formula

wherein R$^{53}$ is aralkyl as defined above.

As used herein the term "nitro" is represented by a radical of the formula

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to a radical of the formula —COOH.

As used herein the term "aminoalkyl" refers to a radical of the formula —R$^{54}$—NH$_2$ wherein R$^{54}$ is lower alkylene as defined above.

As used herein the term "carboxyl derivative" refers to a radical of the formula

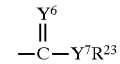

wherein Y$^6$ and Y$^7$ are independently selected from the group consisting of O, N or S and R$^{23}$ is selected from the group consisting of H, alkyl, aralkyl or aryl as defined above.

As used herein the term "amino" is represented by a radical of the formula —NH$_2$.

As used herein the term "alkylsulfonyl" or "alkylsulfone" refers to a radical of the formula

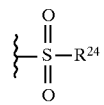

wherein R$^{24}$ is alkyl as defined above.

As used herein the term "alkylthio" refers to a radical of the formula —SR$^{24}$ wherein R$^{24}$ is alkyl as defined above.

As used herein the term "sulfonic acid" refers to a radical of the formula

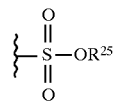

wherein R$^{25}$ is H, alkyl or aryl as defined above.

As used herein the term "sulfonamide" refers to a radical of the formula

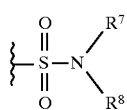

wherein R⁷ and R⁸ are as defined above.

As used herein, the term "N-substituted pyrrolidinyl" refers to a radical of the formula

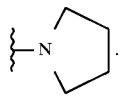

As used herein the term "N-substituted piperidinyl" refers to a radical of the formula

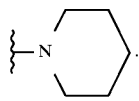

As used herein the term "morpholinyl" refers to a radical of the formula

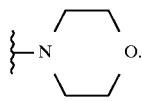

As used herein the term "fused aryl" refers to an aromatic ring such as the aryl groups defined above fused to one or more phenyl rings. Embraced by the term "fused aryl" is the radical naphthyl.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the radical

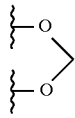

and the term "ethylenedioxy" refers to the radical

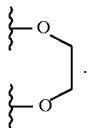

As used herein the term "4–12 membered dinitrogen containing heterocycle refers to a radical of the formula

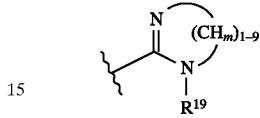

wherein m is 1 or 2 and $R^{19}$ is H, alkyl, aryl, or aralkyl and more preferably refers to 4–9 membered ring and includes rings such as imidazoline.

As used herein the term "5-membered heteroaromatic ring" includes for example a radical of the formula

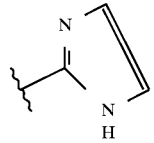

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

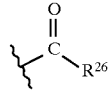

wherein $R^{26}$ is alkyl, alkenyl, alkynyl, aryl or aralkyl as defined above. Encompassed by such radical are the groups acetyl, benzoyl and the like.

As used herein the term "thio" refers to a radical of the formula

As used herein the term "sulfonyl" refers to a radical of the formula

wherein $R^{27}$ is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

wherein $R^{29}$ is aryl as defined above.

As used herein the term "acylamino" refers to a radical of the formula

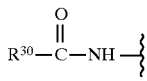

wherein $R^{30}$ is alkyl, aralkyl or aryl as defined above.

As used herein the term "amido" refers to a radical of the formula

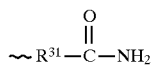

wherein $R^{31}$ is a bond or alkylene as defined above.

As used herein the term "alkylamino" refers to a radical of the formula —$NHR^{32}$ wherein $R^{32}$ is alkyl as defined above.

As used herein the term "dialkylamino" refers to a radical of the formula —$NR^{33}R^{34}$ wherein $R^{33}$ and $R^{34}$ are the same or different alkyl groups as defined above.

As used herein the term "trifluoromethyl" refers to a radical of the formula

As used herein the term "trifluoroalkoxy" refers to a radical of the formula

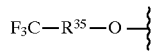

wherein $R^{35}$ is a bond or an alkylene as defined above.

As used herein the term "alkylaminosulfonyl" refers to a radical of the formula

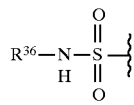

wherein $R^{36}$ is alkyl as defined above.

As used herein the term "alkylsulfonylamino" refers to a radical of the formula

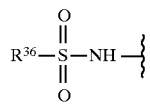

wherein $R^{36}$ is alkyl as defined above.

As used herein the term "trifluoromethylthio" refers to a radical of the formula

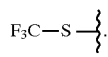

As used herein the term "trifluoromethylsulfonyl" refers to a radical of the formula

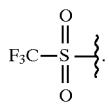

As used herein the term "4–12 membered mono-nitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

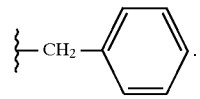

As used herein the term "phenethyl" refers to the radical

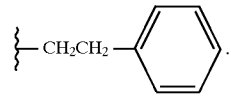

As used herein the term "4–12 membered mono-nitrogen containing sulfur or oxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "arylsulfonyl" or "arylsulfone" refers to a radical of the formula

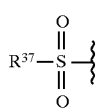

wherein $R^{37}$ is aryl as defined above.

As used herein the terms "alkylsulfoxide" or "arylsulfoxide" refer to radicals of the formula

wherein $R^{38}$ is, respectively, alkyl or aryl as defined above.

As used herein the term "phosphonic acid derivative" refers to a radical of the formula

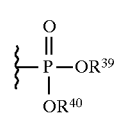

wherein $R^{39}$ and $R^{40}$ are the same or different H, alkyl, aryl or aralkyl.

As used herein the term "phosphinic acid derivatives" refers to a radical of the formula

wherein $R^{41}$ is H, alkyl, aryl or aralkyl as defined above.

As used herein the term "arylthio" refers to a radical of the formula

wherein $R^{42}$ is aryl as defined above.

As used herein the term "monocyclic heterocycle thio" refers to a radical of the formula

wherein $R^{43}$ is a monocyclic heterocycle radical as defined above.

As used herein the terms "monocyclic heterocycle sulfoxide" and "monocyclic heterocycle sulfone" refer, respectively, to radicals of the formula

and

wherein $R^{43}$ is a monocyclic heterocycle radical as defined above.

As used herein the phrase "wherein the X—$R^3$ group is attached to the phenyl of the Y group at the para position to form a lactone" refers to a radical of the formula

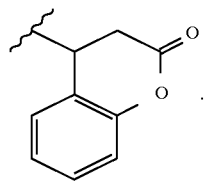

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

| | |
|---|---|
| $^1$H-NMR = | proton nuclear magnetic resonance |
| AcOH = | acetic acid |
| BH$_3$-THF = | borane-tetrahydrofuran complex |
| BOC = | tert-butoxycarbonyl |
| Cat. = | catalytic amount |
| CH$_2$Cl$_2$ = | dichloromethane |
| CH$_3$CN = | acetonitrile |
| CH$_3$I = | iodomethane |
| CHN analysis = | carbon/hydrogen/nitrogen elemental analysis |
| CHNCl analysis = | carbon/hydrogen/nitrogen/chlorine elemental analysis |
| CHNS analysis = | carbon/hydrogen/nitrogen/sulfur elemental analysis |
| DCC = | 1,3-dicyclohexylcarbodiimide |
| DIEA = | diisopropylethylamine |
| DMA = | N,N-dimethylacetamide |
| DMAP = | 4-(N,N-dimethylamino) pyridine |
| DMF = | N,N-dimethylformamide |
| DSC = | disuccinyl carbonate |
| EDCl = | 1-(3-dimethylaminopropyl)-3-ethylcarbodiimide hydrochloride |
| Et$_2$O = | diethyl ether |
| Et$_3$N = | triethylamine |
| EtOAc = | ethyl acetate |
| EtOH = | ethanol |
| FAB MS = | fast atom bombardment mass spectroscopy |
| g = | gram(s) |
| GIHA HCl = | meta-guanidino-hippuric acid hydrochloride |
| GIHA = | meta-guanidino-hippuric acid |
| HPLC | high performance liquid chromatography |
| IBCF = | isobutylchloroformate |
| K$_2$CO$_3$ = | potassium carbonate |
| KOH = | potassium hydroxide |
| LiOH = | lithium hydroxide |
| MCPBA = | m-chloroperoxybenzoic acid or m-chloroperbenzoic acid |
| MeOH = | methanol |
| MesCl = | methanesulfonylchloride |
| mg = | milligram |
| MgSO$_4$ = | magnesium sulfate |
| ml = | milliliter |
| mL = | milliliter |
| MS = | mass spectroscopy |
| N$_2$ = | nitrogen |
| NaCNBH$_3$ = | sodium cyanoborohydride |
| Na$_3$PO$_4$ = | sodium phosphate |
| Na$_2$SO$_4$ = | sodium sulfate |
| NaHCO$_3$ = | sodium bicarbonate |
| NaOH = | sodium hydroxide |
| NH$_4$HCO$_3$ = | ammonium bicarbonate |
| NH$_4$$^+$HCO$_2$$^-$ = | ammonium formate |
| NMM = | N-methyl morpholine |
| NMR = | nuclear magnetic resonance |
| RPHPLC = | reverse phase high performance liquid chromatography |
| RT | room temperature |
| KSCN = | potassium thiocyanate |
| Pd/C = | palladium on carbon |
| Bn = | benzyl |
| Et = | ethyl |
| Me = | methyl |
| Ph = | phenyl |
| NEt$_3$ = | triethylamine |
| t-BOC = | tert-butoxycarbonyl |
| TFA = | trifluoroacetic acid |
| THF = | tetrahydrofuran |
| Δ = | heating the reaction mixture |

As used herein HPLC-Method 1 refers to reverse phase C-18 functionalized silica gel column (50×300 mm) using a linear gradient of 95% 0.6% TFA/water:5% CH$_3$CN to 60% 0.6% TFA/water: 40% CH$_3$CN with a flow rate of 80 ml/minute.

The compounds as shown in Formulas I–III can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of Formula I with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, tartrate salts and the like. All of the pharmacologically acceptable salts may be prepared by conventional means. (See Berge et al., *J Pharm. Sci.*, 66(1), 1–19 (1977) for additional examples of pharmaceutically acceptable salts.)

For the selective inhibition or antagonism of $\alpha_v\beta_3$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ cell surface receptor which method comprises administering a therapeutically effective amount of a compound selected from the class of compounds depicted in Formulas I–III, wherein one or more compounds of the Formulas I–III is administered in association with one or more non-toxic, pharmaceutically acceptable carriers and/or diluents and/or adjuvants (collectively referred to herein as "carrier" materials) and if desired other active ingredients. More specifically, the present invention provides a method for inhibition of the $\alpha_v\beta_3$ cell surface receptor. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 1000 mg per kilogram of body weight per day are useful in the treatment of the above-indicated conditions and more preferably of the order from about 0.01 mg to about 100 mg/kg of body weight.

The active ingredient administered by injection is formulated as a composition wherein, for example, saline, dextrose or water may be used as a suitable carrier. A suitable daily dose would typically be about 0.01 to 100 mg/kg body weight injected per day in multiple doses depending on the factors listed above and more preferably from about 0.01 to about 10 mg/kg body weight.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in Schemes I–III. Both an explanation of, and the actual procedures for, the various aspects of the present invention are described where appropriate. The following Schemes and Examples are intended to be merely illustrative of the present invention, and not limiting thereof in either scope or spirit. Those of skill in the art will readily understand that known variations of the conditions and processes described in the Schemes and Examples can be used to perform the process of the present invention.

Unless otherwise indicated all starting materials and equipment employed were commercially available.

SCHEME I
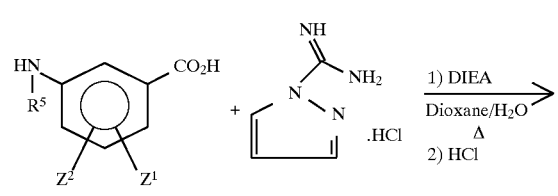
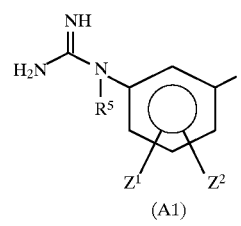
(A1)
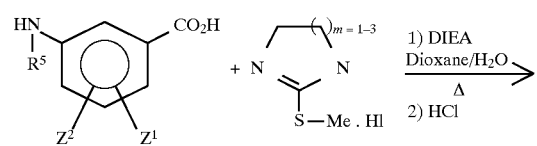
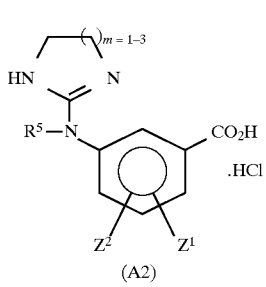
(A2)
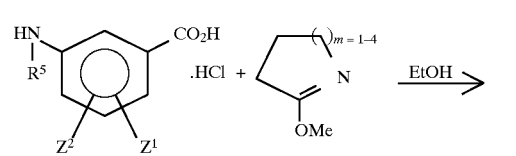
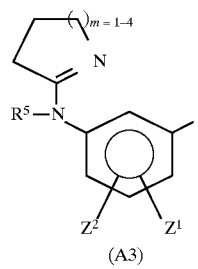
(A3)
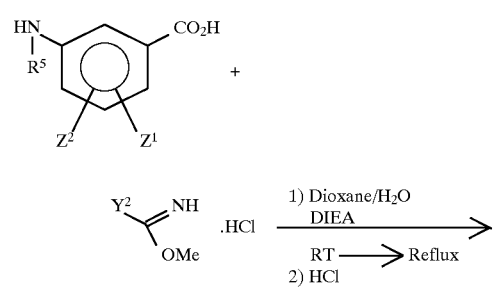
-continued
SCHEME I
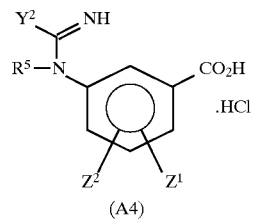
(A4)
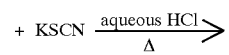
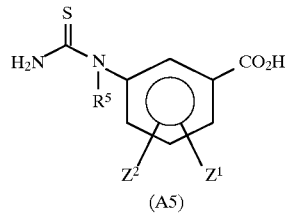
(A5)
(A5) + R⁹—I $\xrightarrow{\text{THF}}{\Delta}$
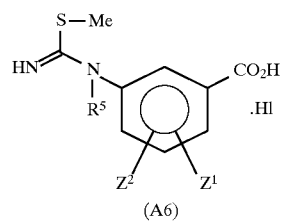
(A6)
(A5) + CH₃I $\xrightarrow{\text{THF}}{\Delta}$
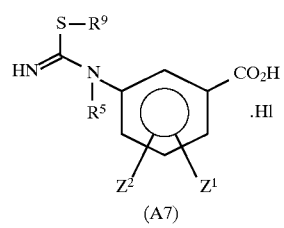
(A7)
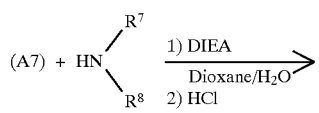
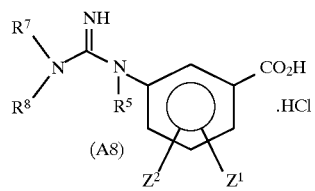
(A8)
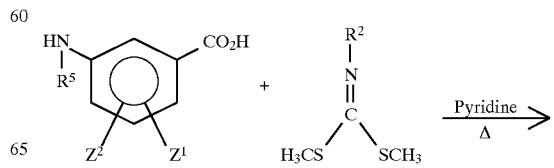

-continued
SCHEME I
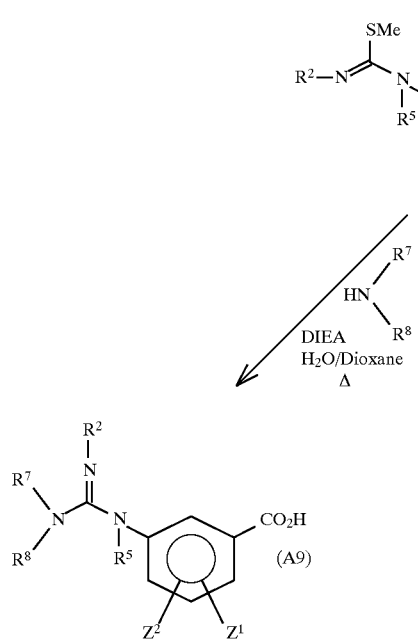
-continued
SCHEME I
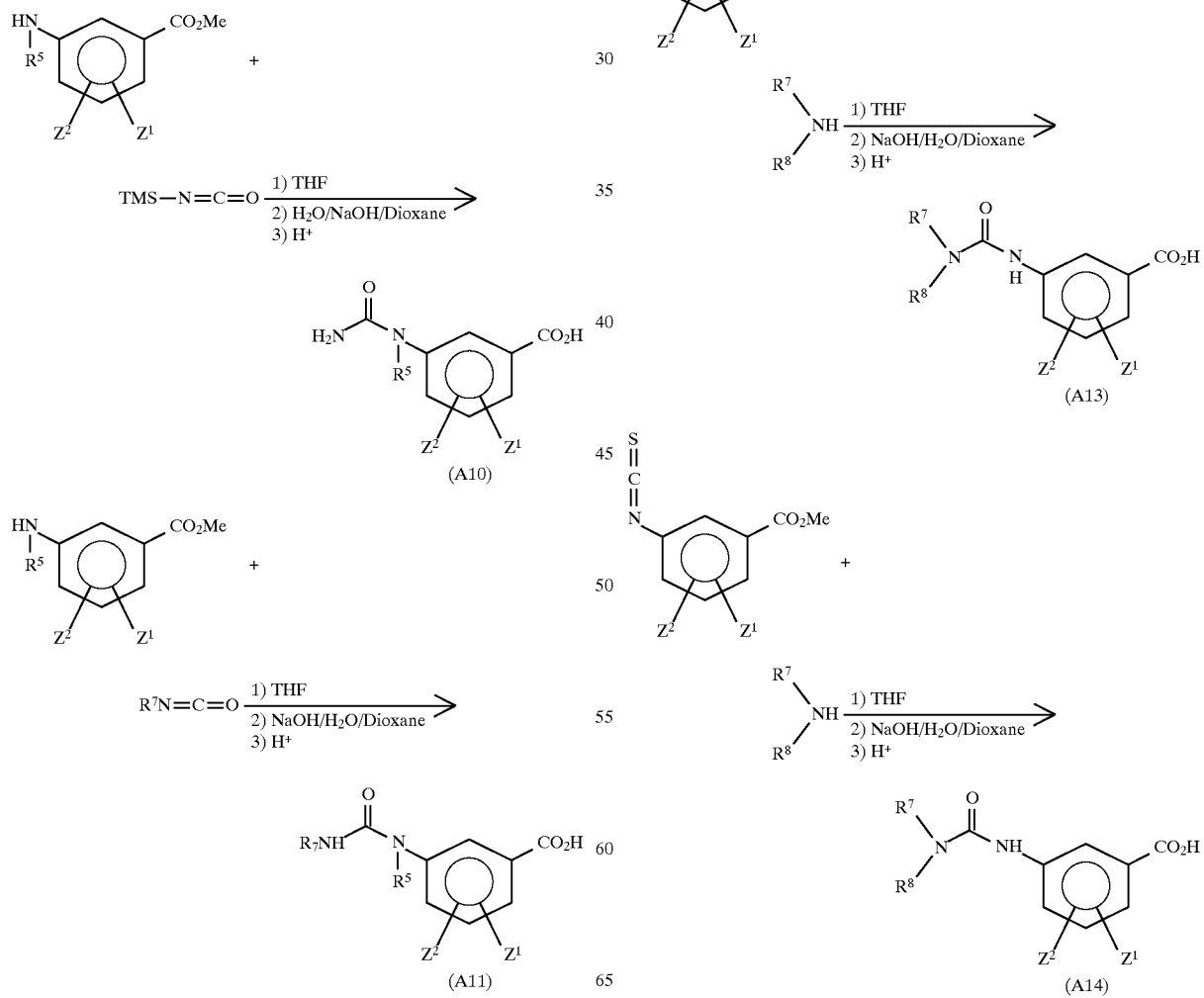

-continued
SCHEME I

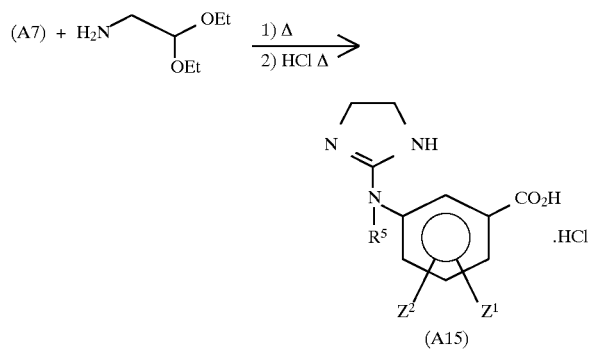

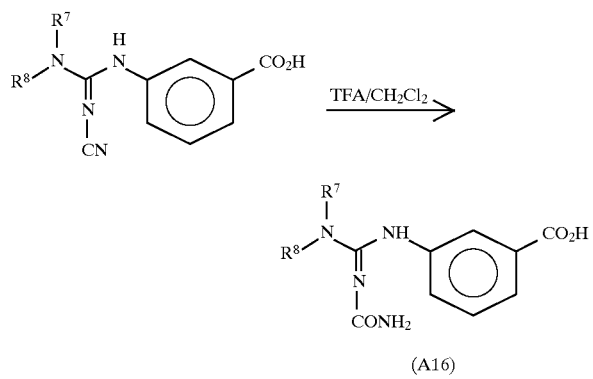

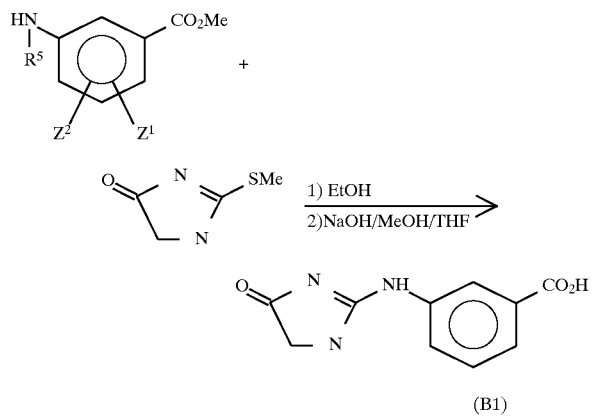

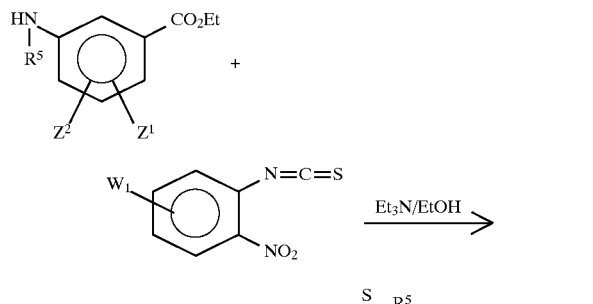

-continued
SCHEME I

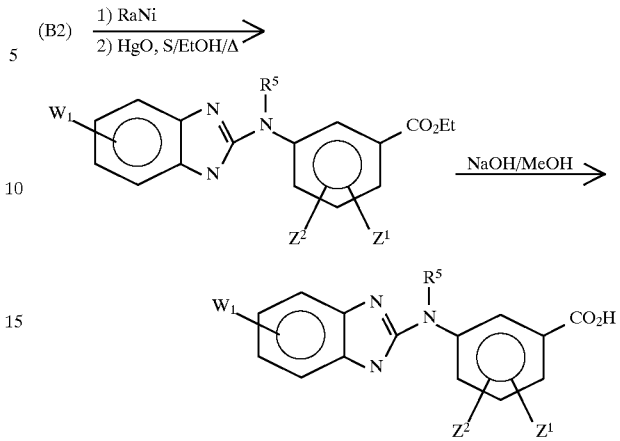

Scheme I is illustrative of methodology useful for preparing various compounds of the present invention. Such methodology is more specifically defined in the examples which follow. Such methodology can be modified by one skilled in the art, substituting known reagents and conditions from conventional methodology to produce the desired compounds.

Specifically, in Scheme I:

In the synthesis of intermediate benzoic acids (A1) through (A16), the starting amino benzoic acids

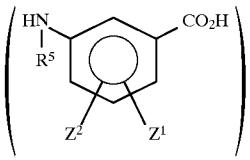

are either commercially available or can be converted to such amino benzoic acids via reduction of the corresponding nitro benzoic acid, which can be obtained commercially or syntheized by nitration of the appropriate benzoic acid, followed by reduction to the desired amino benzoic acid. These are all when $R^5$ is H. If $R^5$ is other than H, alkylation of the amino functionality can be achieved by conventional methodology.

Furthermore, synthesis of intermediate (A2) can also be accomplished as disclosed generally in U.S. Pat. No. 3,202,660, starting with the appropriate amino benzoic acid. Furthermore, intermediate (A2) and (A15) as well as further analogues of (A2) and (A15) such as substitutions on the heterocyclic ring, oxazolidines, thiazolidines, benzimidazoles and the like can also be accomplished as disclosed in 1) Chem. Pharm. Bull. 41(1) 117–125 (1993)
2) Chem. Pharm. Bull. 33(10) 4409–4421 (1985)
3) J. Med. Chem. 18 (1), 90–99 (1975).

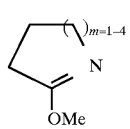

used in the synthesis of intermediates (A3), can be synthesized from

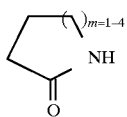

and $(Me)_3OBF_4$ in dichloromethane.

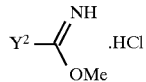

used in the synthesis of intermediate (A4), can be synthesized from $Y^2$—CN and MeOH (1 equivalent) and HCl gas (1 equivalent) in heptane.

Furthermore, the procedures outlined in Scheme I are also applicable to the preparation of the corresponding sulphonic acids described herein.

All other reagents in Scheme I are either commercially available or readily synthesized by methodologies known by those skilled in the art.

SCHEME II
(In all cases $R^{57}$ = alkyl, alkylaryl, t-Bu)

(A)
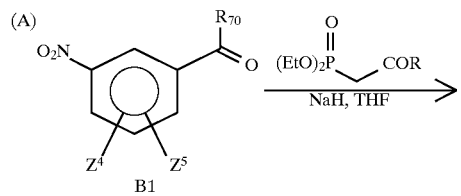

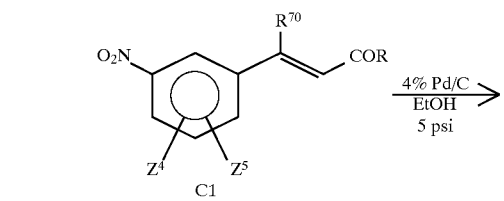

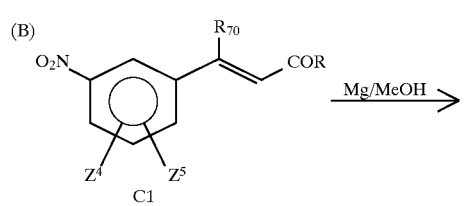

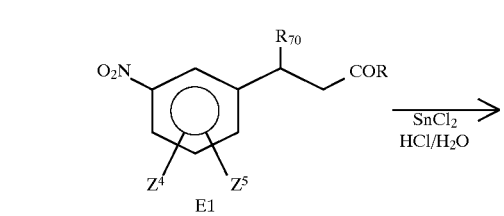

-continued
SCHEME II
(In all cases $R^{57}$ = alkyl, alkylaryl, t-Bu)

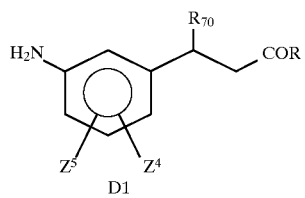

(C)
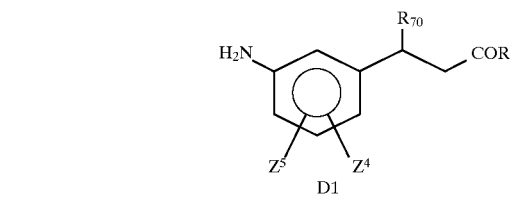

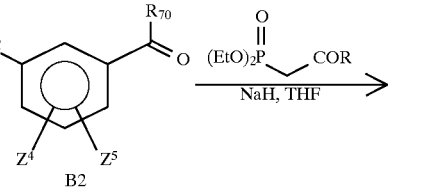

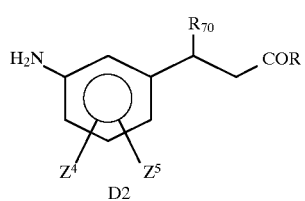

(D) (M = $NO_2$ or CN)
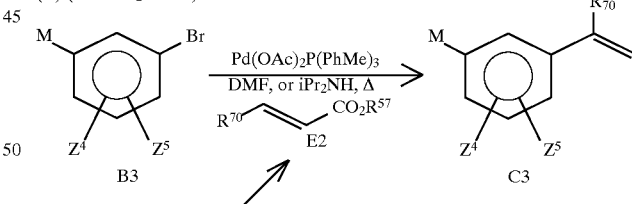

$R^{70}$—CHO
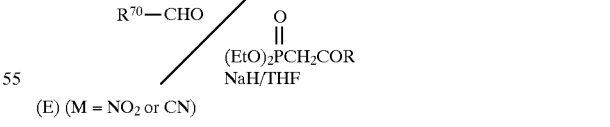

(E) (M = $NO_2$ or CN)
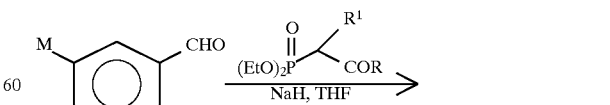

SCHEME II (continued)
(In all cases $R^{57}$ = alkyl, alkylaryl, t-Bu)

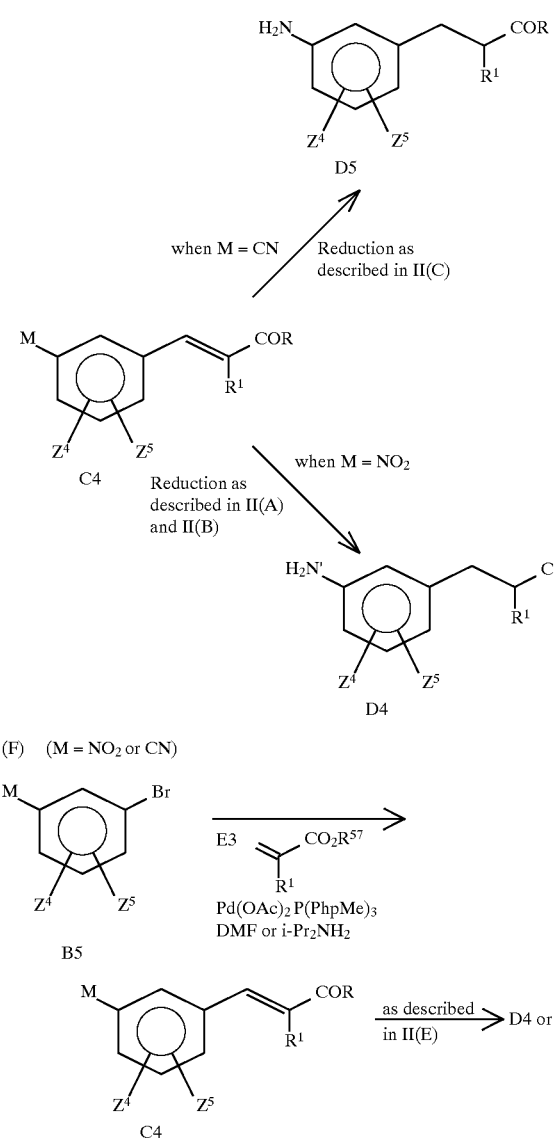

In Scheme II(A) phenylpropionic acid D1 is readily prepared from aldehyde/or ketone B1 in the following manner.

Aldehyde or ketone B1 is condensed with $(EtO)_2P(O)CH_2COR$ under standard conditions (NaH/THF 0° to room temperature). The resulting cinnamic acid derivative C1 is reduced (4% Pd/C, EtOH, 5 psi) to afford the desired phenylpropionic acids D1.

When substituents $Z^4$ and $Z^5$ are sensitive to the catalytic hydrogenation conditions described above, the following synthetic procedure may be utilized.

Nitrophenylcinnamic acid C1 is partially reduced with magnesium in MeOH to afford nitrophenylpropionic acid E1. Further reduction of the nitro moiety ($SnCl_2/H_2O/HCl/EtOH$) affords the desired phenylpropionic acid D1.

In an identical manner to that described in Scheme II(A) aldehyde/or ketone B2 is readily converted into phenylpropionic acid D2.

In Scheme II(D), phenylpropionic acids D1 and D2 may be prepared from bromide B3.

Bromide B3 can be coupled with alkylacrylates E2 using a standard Heck coupling procedure ($Pd(OAc)_2$, $P(PhMe)_3$, DMF, 130°) to afford cinnamic acid C3. Cinnamic acid C3 may be converted into phenylpropionic acid D1 (where $M=NO_2$) and phenylpropionic acid D2 (where M=CN) using the reductions described in Scheme II(A), (B) and (C).

Furthermore, alkylacrylates E2, are readily prepared by condensing the requisite aldehyde ($R^{56}CHO$) with $(EtO)_2P(O)CH_2COR$ using standard and well known reaction conditions such as (NaH, THF, 0°).

In Scheme II(E), phenylpropionic acids D4 and D5 may be prepared from aldehyde B4 as described below.

Aldehyde B4 is condensed with $(EtO)_2P(O)CH_2COR$ using standard conditions (NaH, THF, 0° C.) to afford substituted phenylcinnamic acid C4.

Phenylcinnamic acid C4 may be converted into phenylpropionic acid D4 (where $M=NO_2$) and phenylpropionic acid D5 (where M=CN) using the reductions described in Scheme II(A), (B) and (C).

In Scheme II(F), phenylpropionic acids D4 and D5 may be prepared from bromide B5.

Bromide B5 can be coupled with alkylacrylates E3 using a standard Heck coupling procedure ($Pd(OAc)_2$, $P(PhMe)_3$, DMA, 130°) to afford phenylcinnamic acid C4.

Phenylcinnamic acid C4 may be converted into D4 and D5 as described above in Scheme II(E).

Coupling of the intermediates from Scheme I [(A1) through (A16)] with the intermediate (D1–D5) (from Scheme II Steps (A–F)) can be accomplished using the following coupling methods and other coupling reagents known to those in the art to give the final desired products. All electrophilic intermediates containing $R^1$ from Scheme I, Step (A) are either commercially available or are readily synthesized via methodology known to those skilled in the art.

SCHEME III

Method A

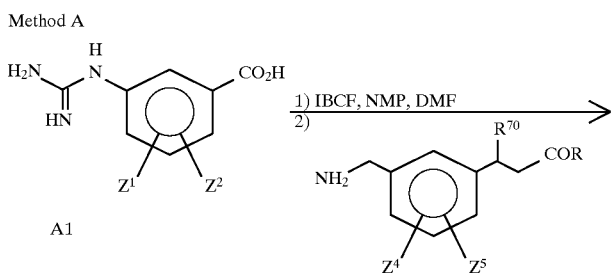

5,773,646
-continued
SCHEME III
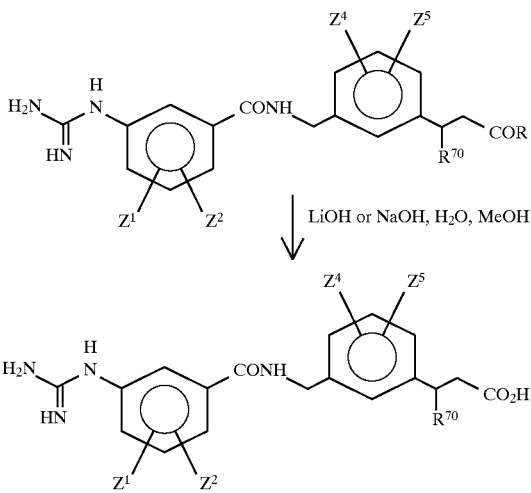
Method B
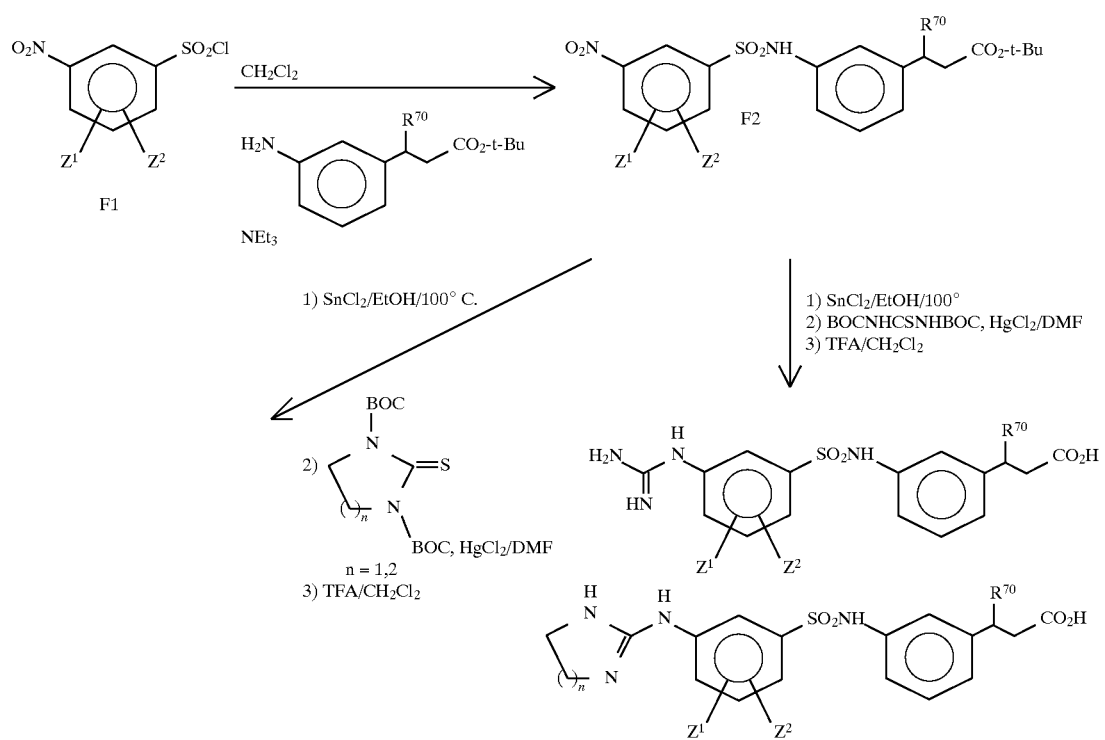
Method C
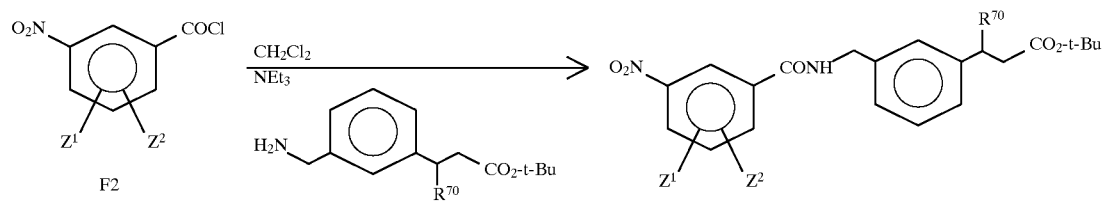

-continued
SCHEME III

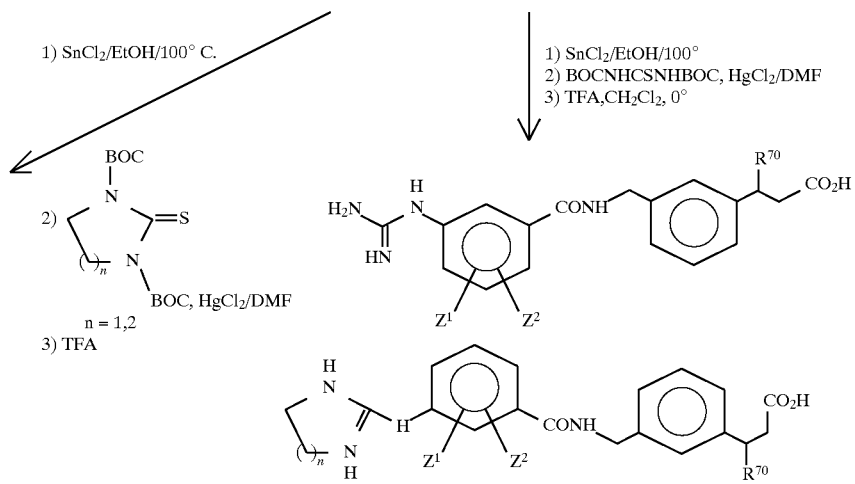

Method B

An alternative method to prepare compounds of the present invention is outlined below.

In this procedure, intermediates D1–D5 (from Scheme II, (A–F)) are coupled to 3-nitro phenylsulphonyl chloride F1 ($CH_2Cl_2$, $NEt_3$ 0°). The resulting coupled product F2 is reduced ($SnCl_2$/EtOH $H_2O$, 100°) to the corresponding aniline. The resulting aniline may be converted into compounds of the present invention using the procedures described in Scheme I (A1–A16) followed by deprotection (TFA/$CH_2Cl_2$/0°).

This procedure is exemplified by converting the above aniline to its corresponding guanidine analog (BOCNHCSNHBOC, $H_2Cl_2$, DMF) followed by deprotection (TFA, $CH_2Cl_2$).

Method C

Method C is identical to that described in Method B except the 3-nitrophenylsulphonyl chloride F1 is replaced with 3-nitrobenzoylchloride F2.

When $R^{11}$ is not H, the appropriate nitrogen can be alkylated in an appropriate step by methodology known to those skilled in the art. Alternate acid derivatives R are synthesized by methodologies known to those skilled in the art.

To synthesize compounds wherein

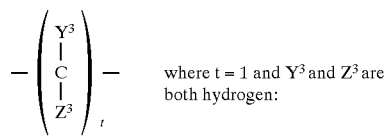 where t = 1 and $Y^3$ and $Z^3$ are both hydrogen:

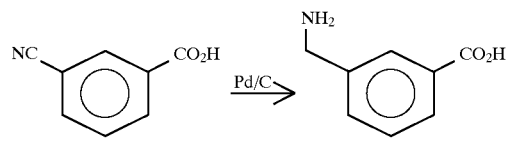

which is then treated in the same manner of further derivatization as exemplified in the previous schemes for:

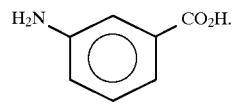

SCHEME IV

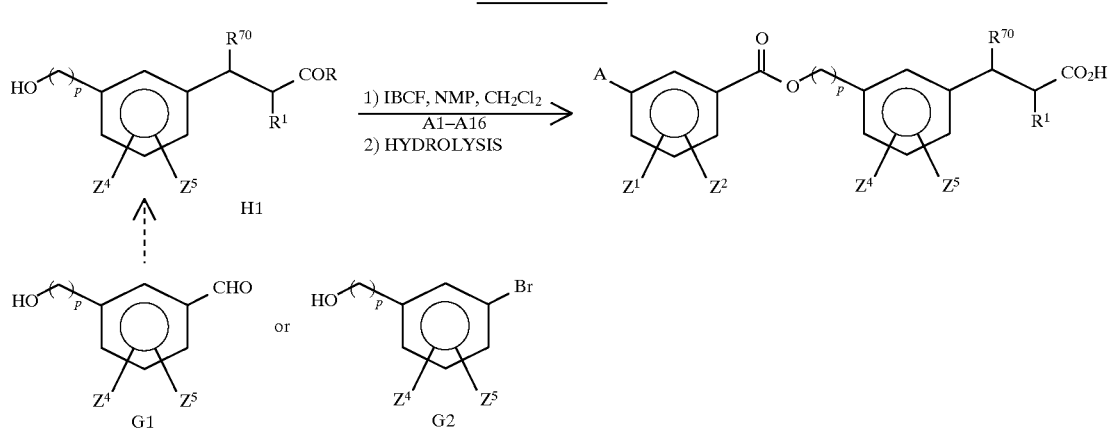

p = 0 and 1

In an analogous fashion to that described in Scheme II(a–h) and as depicted in Scheme IV, aldehyde G1 or bromide G2 can be converted into phenylpropanoic acid H1 (using well established and known chemistry to mask and unmask the hydroxy moiety).

Phenylpropanoic acid H1 is then readily coupled to benzoic acids A1–A15 using procedures previously described to afford the compounds of the present invention.

SCHEME V

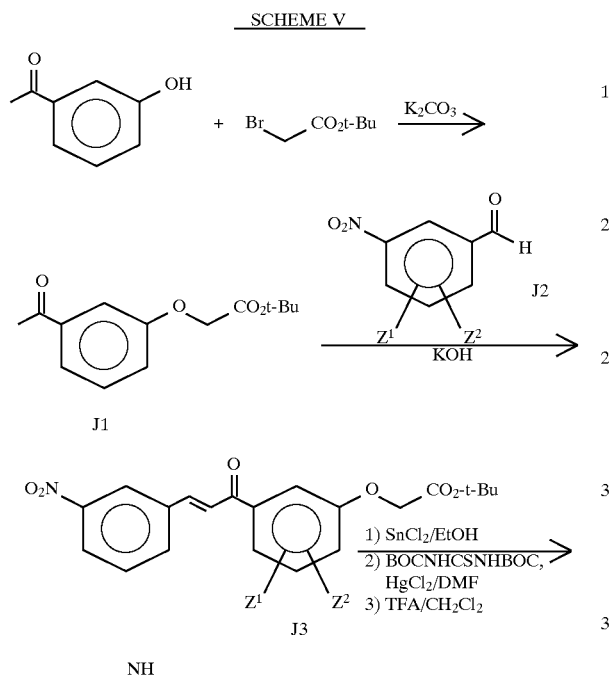

Scheme V outlines methodologies for preparing the chalcone derivatives (J3) of the present invention. 3-Hydroxyacetophenone was reacted with t-butyl bromoacetate ($K_2CO_3$/DMF) to provide J1, which was condensed with 3-nitrobenzaldehyde (J2) (KOH, EtOH). The resulting product J3 was reduced ($SnCl_2$/EtOH) to the corresponding aniline. The resulting aniline was converted to its corresponding guanidine analog (BOCNHCSNHBOC, $Hg_2Cl_2$, DMF), followed by deprotection (TFA, $CH_2Cl_2$), or otherwise functionalized as described in Scheme I.

SCHEME VI

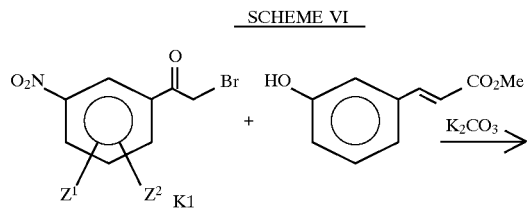

-continued
SCHEME VI

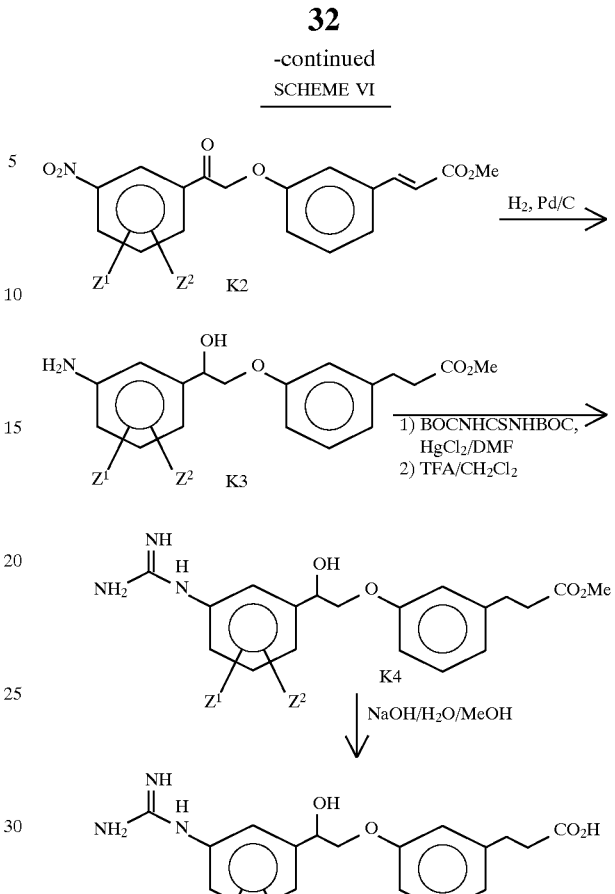

Scheme VI outlines methodologies for preparing the K3 type derivatives of the present invention. 3-Hydroxycinnamate was reacted with 2-bromo-3'-nitroacetophenone (K1) ($K_2CO_3$/acetone) to provide K2. The resulting product was reduced ($H_2$, Pd/C) to the corresponding aniline K3. The resulting aniline was converted to its corresponding guanidine analog (BOCNHCSNHBOC, $Hg_2Cl_2$, DMF), followed by deprotection (TFA, $CH_2Cl_2$), or otherwise functionalized as described in Scheme I, to give K4. Hydrolysis under standard basic conditions (NaOH/$H_2O$/MeOH) provided the carboxylic acid derivative.

SCHEME VII

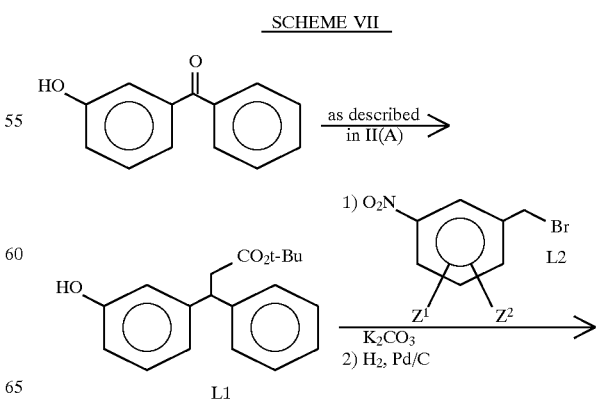

-continued
SCHEME VII

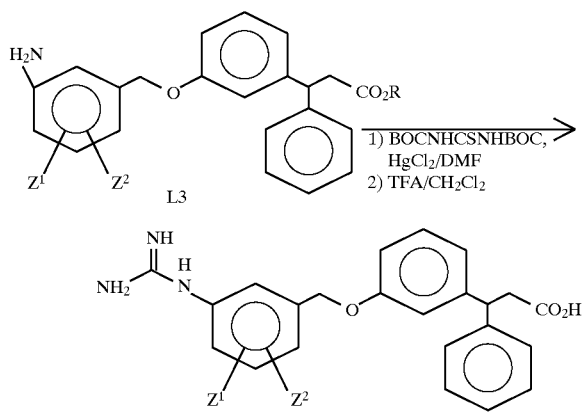

Scheme VII outlines methodologies for preparing the L3 type derivatives of the present invention. 3-Hydroxybenzophenone was converted to L1 using the methods described in Scheme II(A). L1 was coupled with 3-nitrobenzyl bromide (L2) and reduced (H₂, Pd/C). The resulting aniline L3 was converted to its corresponding guanidine analog (BOCNHCSNHBOC, Hg₂Cl₂, DMF), followed by deprotection (TFA, CH₂Cl₂), or otherwise functionalized as described in Scheme I.

SCHEME VIII

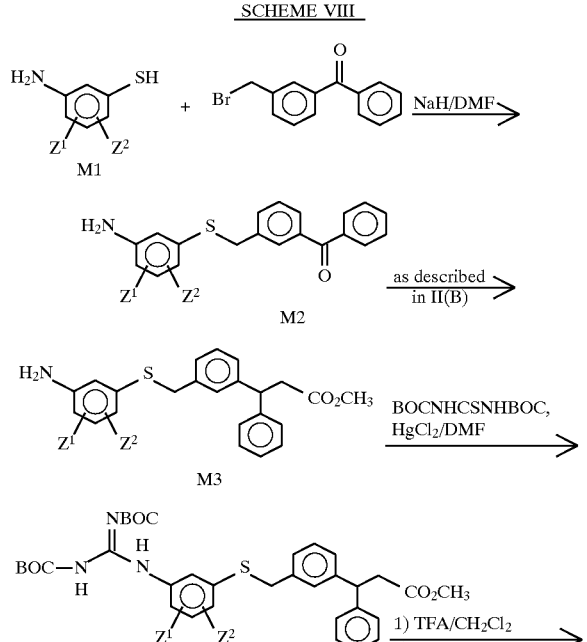

-continued
SCHEME VIII

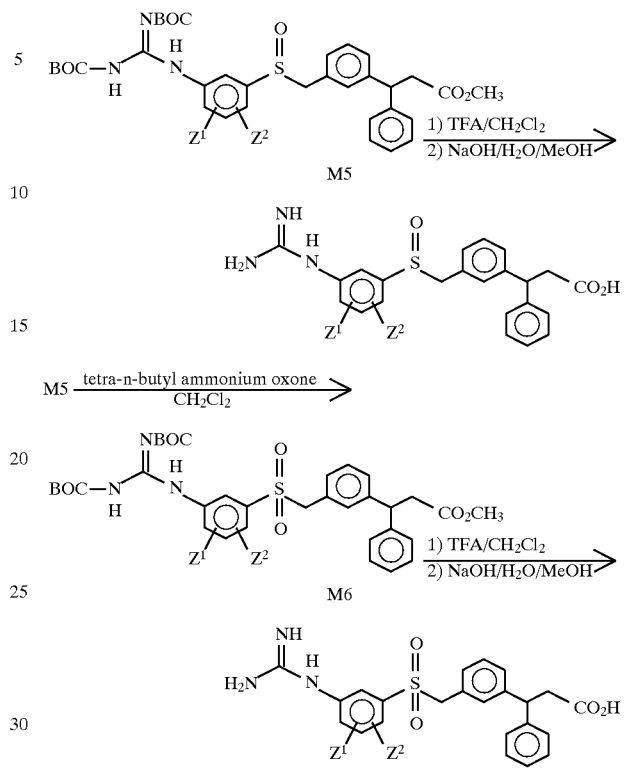

Scheme VIII outlines methodologies for preparing the thio derivatives of the present invention. 3-Thioaniline (M1) was reacted with 3-bromobenzophenone (NaH, DMF) to provide M2. M2 was converted to M3 using the methods described in Scheme II(B). M3 was converted to its corresponding guanidine analog (BOCNHCSNHBOC, Hg₂Cl₂, DMF), or otherwise functionalized as described in Scheme I to give M4. M4 was deprotected (TFA, CH₂Cl₂), followed by hydrolysis under standard basic conditions (NaOH/H₂O/MeOH) to provide the corresponding carboxylic acid derivative.

M4 was oxidized (tetra-n-butyl ammonium oxone/CH₂Cl₂) to give M5, which was deprotected (TFA, CH₂Cl₂), followed by hydrolysis under standard basic conditions (NaOH/H₂O/MeOH) to provide the corresponding carboxylic acid derivative.

M5 was oxidized (tetra-n-butyl ammonium oxone/CH₂Cl₂) to give M6, which was deprotected (TFA, CH₂Cl₂), followed by hydrolysis under standard basic conditions (NaOH/H₂O/MeOH) to provide the corresponding carboxylic acid derivative.

SCHEME IX

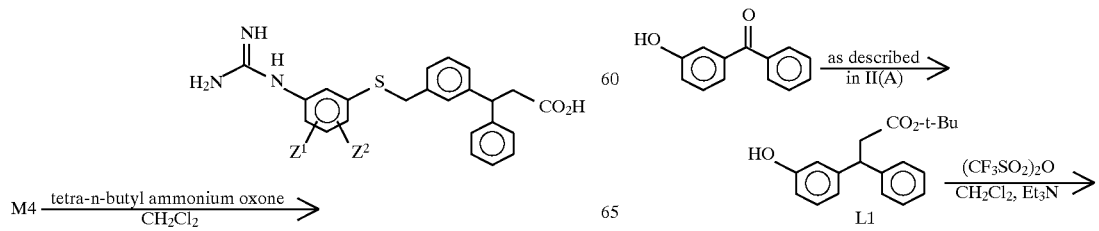

SCHEME IX (continued)

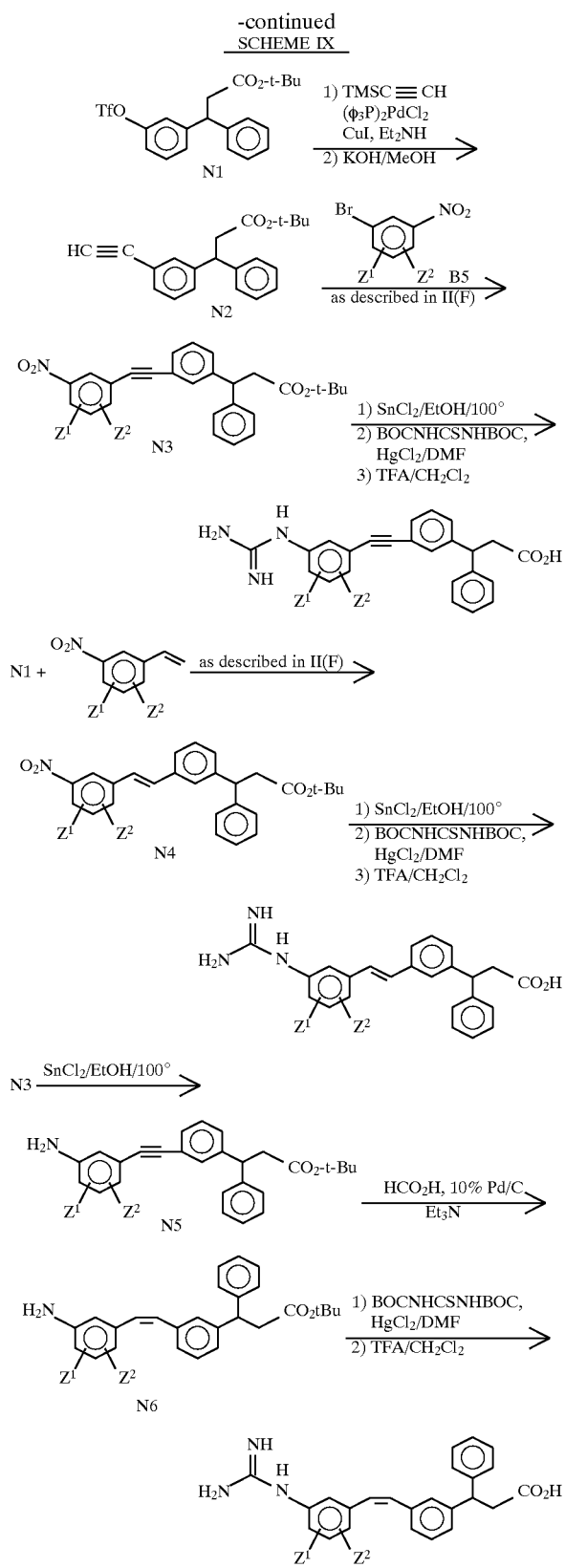

Scheme IX outlines methodologies for preparing the alkene and alkyne derivatives of the present invention. 3-Hydroxybenzophenone was converted to $L_1$ using the methods described in Scheme II(A). $L_1$ was reacted with trifluoromethane sulfonic anhydride ($Et_3N$, $CH_2Cl_2$) to give $N_1$. $N_1$ was reacted with trimethylsilyl acetylene (($Ph_3P$)$_2PdCl_2$, CuI, $Et_2NH$), followed by hydrolysis (KOH/MeOH), to provide N2. N2 was coupled with B5 using the methods described in Scheme II(F). The resulting product N3 was converted to its corresponding guanidine analog (BOCNHCSNHBOC, $Hg_2Cl_2$, DMF), followed by deprotection (TFA, $CH_2Cl_2$), or otherwise functionalized as described in Scheme I.

N1 was coupled with 3-nitro styrene using the methods described in Scheme II(F). The resulting product N4 was reduced ($SnCl_2$/EtOH) to the corresponding aniline. The resulting aniline was converted to its corresponding guanidine analog (BOCNHCSNHBOC, $Hg_2Cl_2$, DMF), followed by deprotection (TFA, $CH_2Cl_2$), or otherwise functionalized as described in Scheme I.

N3 was reduced ($SnCl_2$/EtOH) to the corresponding aniline. The resulting aniline was further reduced ($HCO_2H$, Pd/C, $Et_3N$) to its cis alkene N6. N6 was converted to its corresponding guanidine analog (BOCNHCSNHBOC, $Hg_2Cl_2$, DMF), followed by deprotection (TFA, $CH_2Cl_2$), or otherwise functionalized as described in Scheme I.

N5 can be further reduced to its corresponding alkene ($H_2$, Pd/C) which can be converted to its corresponding guanidine analog (BOCNHCSNHBOC, $Hg_2Cl_2$, DMF), followed by deprotection (TFA, $CH_2Cl_2$), or otherwise functionalized as described in Scheme I.

EXAMPLE A (3-Guanidinobenzoic acid hydrochloride)

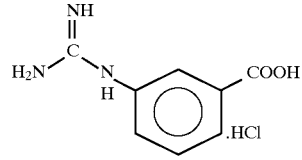

To 3,5-dimethylpyrazole-1-carboxamidine nitrate (6 g, 0.03 mole) (Aldrich) and diisopropylamine (3.8 g, 0.03 mole) in dioxane (20 ml) and $H_2O$ (10 ml) was added 3-aminobenzoic acid (2.7 g, 0.02 mole). The reaction was stirred at reflux for 2.5 hours then overnight at room temperature. The resulting precipitate was filtered, washed with dioxane/$H_2O$ and dried. The precipitate was then slurried in $H_2O$ and acidified with concentrated HCl until a solution formed. The solvent was removed under vacuum and the residue was slurried twice in ether (ether decanted off). The product was dried under vacuum to yield 3-guanidinobenzoic acid hydrochloride (1.77 g) as a white solid. MS and NMR were consistent with the desired structure.

EXAMPLE B 3-(1-Aza-2-amino-1-cycloheptyl)benzoic acid hydrochloride

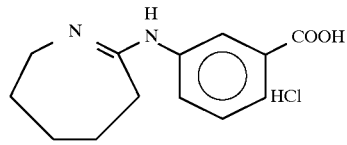

To 1-aza-2-methoxy-1-cycloheptene (3.67 g, 0.0288 mole)(Aldrich) in absolute ethanol (20 ml) was added 3-aminobenzoic acid hydrochloride (5 g, 0.0288 mole). A solution quickly formed. The reaction mixture was stirred overnight at room temperature. The resulting precipitate was filtered, washed with ether and dried under vacuum to yield 3-(1-aza-2-amino-1-cycloheptene)benzoic acid (4.9 g).

EXAMPLE C 3-(1-aza-2-amino-1-cycloheptene)-5-trifluoromethylbenzoic acid hydrochloride

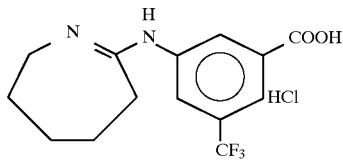

The title compound was synthesized according to the methodology of Example B, substituting an equivalent amount of 3-amino-5-trifluoromethyl benzoic acid [which was synthesized by reduction of 3-nitro-5-trifluoromethyl benzoic acid (Lancaster) in ethanol with 10% Pd/C under 50 psi $H_2$ for 4 hours] for 3-aminobenzoic acid.

EXAMPLE D 3-guanidino-5-trifluoromethylbenzoic acid, hydrochloride

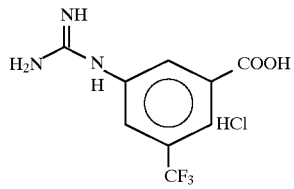

The title compound was synthesized according to the methodology of Example A, substituting an equivalent amount of 3-amino-5-trifluoromethylbenzoic acid (see Example C) for 3-aminobenzoic acid.

EXAMPLE E

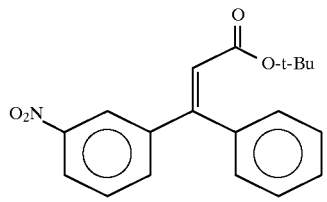

In a flask under nitrogen was placed 1.8 g of sodium hydride (60% mineral oil dispersion; Aldrich) which was washed three times with hexane. The hydride was then suspended in 50 mL of dry tetrahydrofuran (THF) and chilled in an ice bath. A solution of t-butyl P,P-dimethyl phosphonacetate (10.1 g) (Fluka) in THF (25 ml) was added dropwise and the reaction mixture was stirred for 1 hour at 0°. In another flask was dissolved 3-nitrobenzaldehyde (6.8 g) in THF (50 ml). The flask was chilled in an ice bath and the contents of the first flask was added dropwise over 15 minutes at 0°–5° C. The ice bath was then removed and the reaction mixture was stirred for 2 hours at room temperature.

The reaction mixture was then partitioned between ethyl acetate and water. The aqueous portion was extracted several times with ethyl acetate and the combined organic extracts were washed with saturated sodium chloride solution, dried over sodium sulfate and purified on a silica gel column eluting with 10% ethyl acetate –90% hexane to afford 8.9 g of a yellow oil. NMR was consistent with the proposed structure as a mixture of cis and trans isomers.

EXAMPLE F

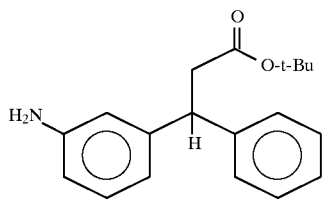

A solution of the product from Example E (8.9 g) in ethanol (80 mL) was hydrogenated under an atmosphere of 5 psi of hydrogen at room temperature for 2 hours using 4% palladium on carbon (1.5 g) as catalyst. The reaction mixture was concentrated and the crude product was purified on a silica gel column eluting with 1:1 ethyl acetate-hexane to afford 6.4 g of white solid. NMR was consistent with the proposed structure.

EXAMPLE G

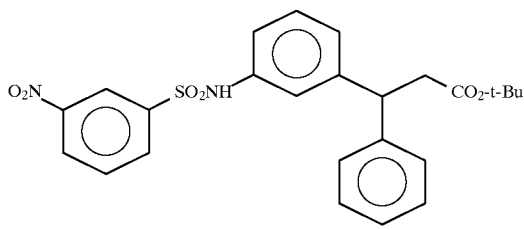

A solution of the product from Example F (1.5 g) and 3-nitro-benzenesulfonylchloride (1.2 g) (Aldrich) in methylene chloride (15 mL) ($CH_2Cl_2$) was chilled to 0° under nitrogen. A solution of triethylamine (510 mg) in $CH_2Cl_2$ (2 mL) was added in one portion and the reaction mixture was then allowed to stir while warming to room temperature for 12 hours. The reaction mixture was then partitioned between chloroform and water and the aqueous portion extracted several times with chloroform. The combined organic extracts were washed with saturated sodium chloride solution (2×), dried ($Na_2SO_4$), and purified on a silica gel column eluting with 40% ethylacetate –60% hexane to afford 900 mg of white solid.

NMR was consistent with the proposed structure.

EXAMPLE H

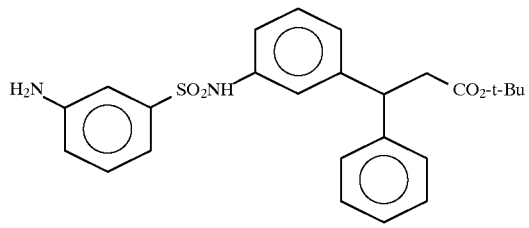

A solution of the product from Example G (3.0 g) in a 1:1 mixture of ethanol and THF (50 ml) was hydrogenated using Raney nickel at warm temperature and 5 psi of hydrogen for 16 hours. The reaction mixture was concentrated and purified on a silica gel column eluting with 70% ethyl acetate –30% hexane to afford 1.8 g of white solid.

NMR was consistent with the proposed structure.

EXAMPLE I

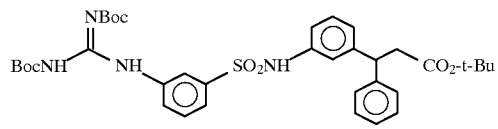

To a solution of the product from Example H (625 mg), bis-t-butoxycarbonyl thiourea, (Ivanowicz et al., Synthetic Communications, 1993, 23, 1443) and triethylamine (461 mg) (Et$_3$N) in DMF (10 ml) at 0° under nitrogen was added mercuric chloride (416 mg) in one portion. The reaction mixture was stirred for 30 minutes at 0° and then 30 minutes at room temperature. The reaction was quenched with ethyl acetate (15 mL), stirred for 30 minutes, and then filtered and concentrated. The crude product was purified on a silica gel column eluting with 25% ethyl acetate –75% hexane to afford 393 mg of white solid.

NMR was consistent with the proposed structure.

EXAMPLE 1

Synthesis of 3-[[[3-[(aminoiminomethyl)amino]phenyl]sulfonyl]amino]-β-phenylbenzenepropanoic acid, trifluoroacetate salt

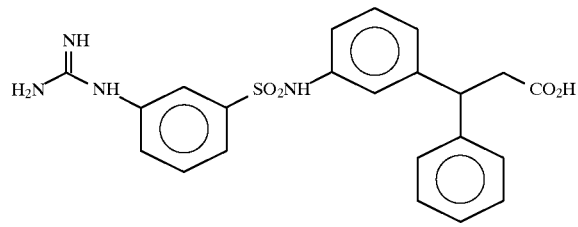

A solution of trifluoroacetate acid (5 ml), methylene chloride (5 ml) and the product from Example I (380 mg) was stirred at room temperature for 1 hour. The reaction mixture was concentrated and the residue was purified via reverse phase HPLC using a water (0.5% TFA) and acetonitrile gradient as eluant to afford 191 mg of white solid. NMR was consistent with the proposed structure.

Analysis Calculated for $C_{22}H_{22}N_4O_4S \cdot 1.4\ CF_3CO_2H$:
C, 49.80; H, 3.94; N, 9.37; S, 5.36

Found: C, 49.81; H, 3.72; N, 9.35; S, 5.17.

EXAMPLE J

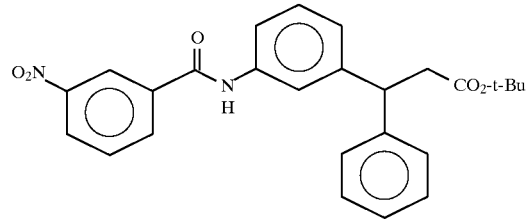

The reaction was run as described in Example G using the product from Example F (1.5 g), 3-nitrobenzoyl chloride (935 mg) (Aldrich), triethylamine (510 mg) and methylene chloride (15 ml). The crude product was purified on a silica gel column eluting with 20% ethyl acetate –80% hexane to afford 1.6 g of white solid. NMR was consistent with the proposed structure.

EXAMPLE K

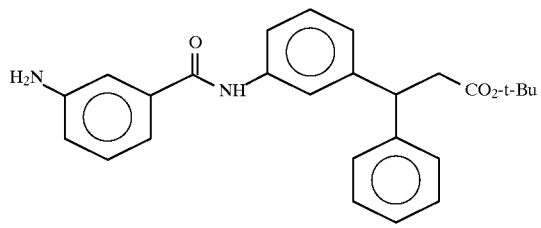

The reaction was run as described in Example F using the product from Example J (1.6 g), ethanol (20 ml) and 4% Pd/C (100 mg). The crude product was purified on a silica gel column eluting with 1:1 ethyl acetate:hexane to afford 1.3 g of white solid.

NMR was consistent with the proposed structure.

EXAMPLE L

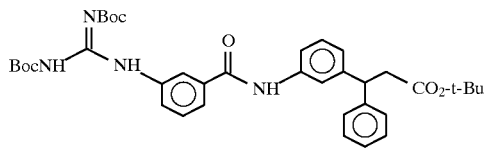

The reaction was run as described in Example I using the product from Example K (1.3 g), bis-t-butoxycarbonyl thiourea (829 mg), triethylamine (1.0 g), mercuric chloride (896 mg) and DMF (10 ml). The crude product was purified on a silica gel column eluting with 25% ethyl acetate –75% hexane to afford 1.1 g of white solid.

NMR was consistent with the proposed structure.

EXAMPLE 2

Synthesis of 3-[[[3-[(aminoiminomethyl)amino]phenyl]carbonyl]amino]-β-phenylbenzenepropanoic acid, trifluoroacetate salt

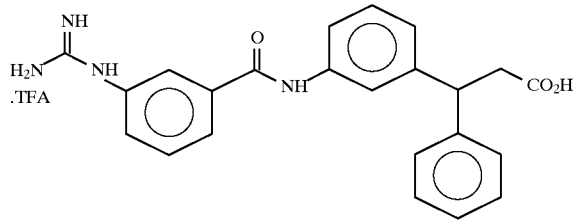

The reaction was run as described in Example 1 using the product from Example L (1.1 g) and a 1:1 TFA:CH$_2$Cl$_2$ solution (10 ml). The crude product was purified as previously described to afford 883 mg of white solid.

NMR was consistent with the proposed structure.

Analysis Calculated for C$_{23}$H$_{22}$N$_4$O$_3$·CF$_3$CO$_2$H·0.75 H$_2$O:

C, 56.66; H, 4.66; N, 10.57.
Found: C, 56.60; H, 4.38; N, 10.57.

EXAMPLE 4

Synthesis of 1,1-dimethylethyl 3-[[[3-[(aminocarbonyl)amino]phenyl]carbonyl]amino]-β-phenylbenzenepropanoate

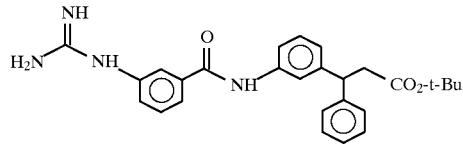

A solution of the product from Example K (750 mg), glacial acetic acid (15 ml) and water (2.5 ml) was heated to 38°. A solution of potassium cyanate (406 mg) (Aldrich) in water (2.5 ml) was added dropwise with stirring. A gummy precipitate resulted. After stirring at room temperature overnight, the solvent was removed in vacuo and the residue was purified on a silica gel column eluting with 1% methanol –99% methylene chloride to afford 452 mg of white solid. NMR was consistent with the proposed structure.

EXAMPLE 5

Synthesis of 3-[[[3-[(aminocarbonyl)amino]phenyl]carbonyl]amino]-β-phenylbenzenepropanoic acid

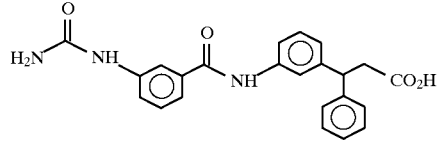

The reaction was run as described in Example 1 using the product from Example 4 (425 mg) to afford 285 mg of white solid. NMR was consistent with the proposed structure.

Analysis Calculated for C$_{23}$H$_{21}$N$_3$O$_4$·1.25 H$_2$O:
C, 64.85; H, 5.56; N, 9.86.

Found: C, 64.69; H, 5.27; N, 9.63.

EXAMPLE P

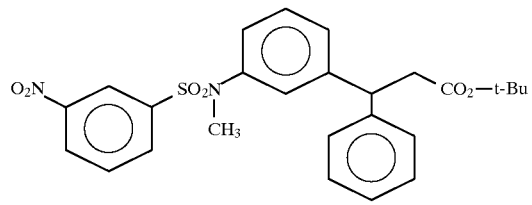

To a solution of potassium carbonate (175 mg) (Aldrich) in DMF (9 ml) at room temperature was added a solution of the product from Example G (500 mg) in DMF (3 ml) dropwise. The reaction mixture was stirred for 30 minutes and then a solution of iodomethane (426 mg) (Aldrich) in DMF (3 ml) was added dropwise. The reaction mixture was stirred for 30 minutes and then partitioned between ethyl acetate and water. The aqueous portion was extracted several times with ethyl acetate and the combined organic extracts were washed with water (2×), saturated sodium chloride solution (1×), and dried (Na$_2$SO$_4$). The solvent was removed in vacuo and the residue was purified on a silica gel column eluting with 25% ethyl acetate –75% hexane to afford 311 mg of a light yellow glass. NMR was consistent with the proposed structure.

EXAMPLE O

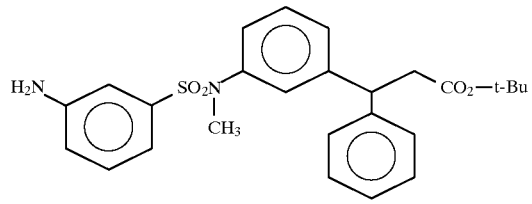

The reaction was run as described in Example N using the product from Example P (450 mg). The crude product was purified in the same fashion to afford 240 mg of a colorless viscous oil. NMR was consistent with the proposed structure.

EXAMPLE R

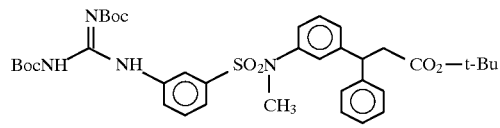

The reaction was run as described in Example I using the product from Example Q (230 mg), bis-t-butoxy-carbonyl thiourea (166 mg), triethylamine (126 mg), and mercuric chloride (163 mg) in DMF (10 ml). The crude product was purified in similar fashion to afford 140 mg of white solid. NMR was consistent with the proposed structures.

EXAMPLE 6

Synthesis of 3-[[[4-[(aminoiminomethyl)amino]phenyl]sulfonyl]methylamino]-β-phenylbenzenepropanoic acid, trifluoroacetate salt

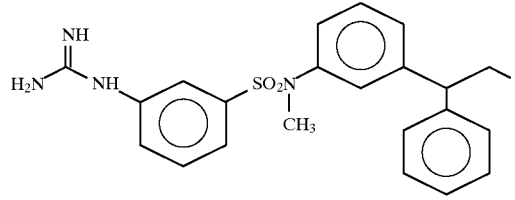

The reaction was run as described in Example 1 using the product from Example R (130 mg) to afford 58 mg of white solid. NMR was consistent with the proposed structure.

Analysis Calculated for $C_{23}H_{24}N_4O_4S \cdot 1.5$ TFA:

C, 50.08; H, 4.12; N, 8.98; S, 5.14.
Found: C, 49.74; H, 4.00; N, 8.87; S, 5.26.

EXAMPLE 7

Synthesis of 1,1-dimethylethyl 3-[[[3-[(aminocarbonyl)amino]phenyl]sulfonyl]amino]-β-phenylbenzenepropanoate

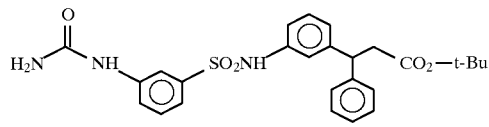

The reaction was run as described in Example 4 using the product (229 mg) from Example H (640 mg), potassium cyanate (229 mg) (Aldrich), glacial acetic acid (3 ml) and water (10 ml). The crude product was purified on a silica gel column eluting with 5% methanol –95% methylene chloride to afford 435 mg of viscous golden oil. NMR was consistent with the proposed structure.

EXAMPLE 8

Synthesis of 3-[[[3-[(aminocarbonyl)amino]phenyl]sulfonyl]amino]-β-phenylbenzenepropanoic acid

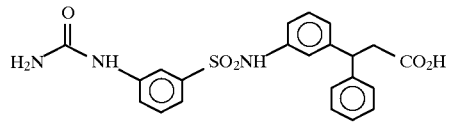

The reaction was run as described in Example 1 using the product from Example 7 (400 mg) to afford 195 mg of white solid. NMR was consistent with the proposed structure.

Analysis Calculated for $C_{22}H_{21}N_3O_5S \cdot 0.4TFA \cdot 0.4\ H_2O$.

C, 55.63; H, 4.55; N, 8.54; S, 6.51.
Found: C, 55.66; H, 4.38; N, 8.46; S, 6.76.

EXAMPLE 9

Synthesis of 1,1-dimethylethyl 3-[[[3-[(aminothioxomethyl)amino]phenyl]sulfonyl]amino]-β-phenylbenzenepropanoate

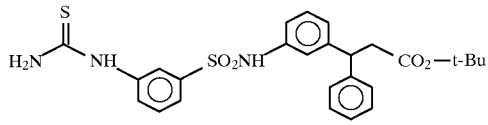

To a solution of thiophosgene (92 mg) (Aldrich) in methylene chloride (1 ml) at 0° was added a solution of the product from Example H (350 mg), triethylamine (162 mg) and methylene chloride (1.5 ml) dropwise. The reaction mixture was stirred for 15 minutes and then concentrated. The residue was dissolved in THF (5 ml) and treated with concentrated ammonium hydroxide solution (5 ml) for 5 minutes at room temperature. The reaction mixture was concentrated and purified on a silica gel column eluting with 3% methanol –97% methylene chloride to afford 236 mg of white solid. NMR was consistent with the proposed structure.

EXAMPLE 10

Synthesis of 3-[[[3-[(aminothioxomethyl)amino]phenyl]sulfonyl]amino]-β-phenylbenzenepropanoic acid

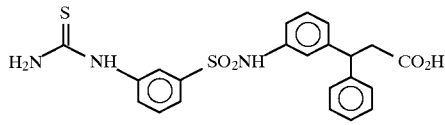

The reaction was run as described in Example 1 using the product from Example 9 (225 mg) to afford 150 mg of white solid. NMR was consistent with the proposed structure.

Analysis Calculated for $C_{22}H_{21}N_3O_4S_2 \cdot 0.5H_2O \cdot 0.25CH_3CN$

C, 56.91; H, 4.83; N, 9.59; S, 13.51.
Found: C, 56.91; H, 4.55; N, 9.48; S, 13.20.

EXAMPLE S

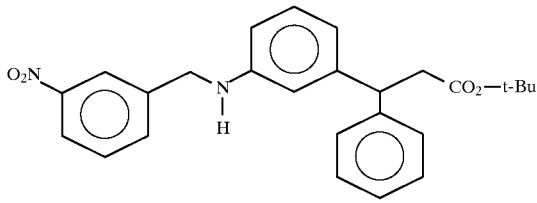

A solution of the product from Example F (1.5 g), 3-nitrobenzyl bromide (1.1 g) (Fluka), potassium carbonate (1.4 g) and DMF (25 ml) was stirred at room temperature under nitrogen for 2 days. The reaction mixture was partitioned between ethyl acetate and water. The aqueous portion was extracted several times with ethyl acetate and then the combined organic extracts were washed with saturated sodium chloride solution (2x), dried ($Na_2SO_4$) and concentrated. The residue was purified on a silica gel column eluting with 25% ethyl acetate –75% hexane to afford 1.5 g

EXAMPLE T

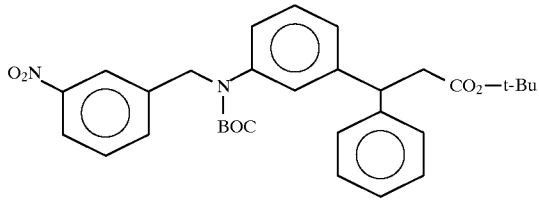

A solution of the product from Example S (1.5 g), triethylamine (7.5 ml), and DMF (20 ml) was treated with di-t-butyldicarbonate (3.0 g) (Aldrich) and 4-dimethylaminopyridine (50 mg) (Aldrich) at 55° for 24 hours. The reaction mixture was cooled to room temperature and partitioned between ethyl acetate and water. The aqueous portion was extracted with additional ethyl acetate and then the combined organic extracts were washed with saturated sodium chloride solution (2×), dried (Na$_2$SO$_4$) and concentrated. The residue was purified on a silica gel column eluting with 20% ethyl acetate –80% hexane to afford 580 mg of viscous golden oil. The NMR structure was consistent with the proposed structure.

EXAMPLE U

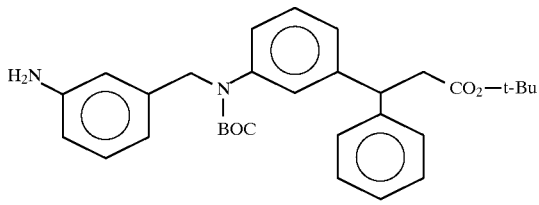

A solution of 560 mg of the product from Example T (560 mg) in ethanol (10 ml) was reduced under an atmosphere of 5 psi hydrogen at room temperature for 4 hours with 5% platinum on carbon catalyst. The reaction mixture was concentrated and purified on a silica gel column eluting with 25% ethyl acetate –75% hexane to afford 340 mg of a viscous colorless oil. NMR was consistent with the proposed structure.

EXAMPLE V

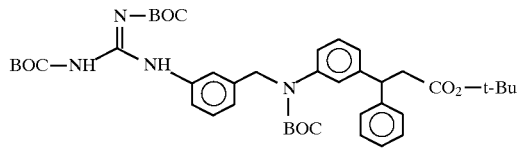

The reaction was run as described in Example I using the product from Example U (320 mg), bis-t-butoxy carbonyl thiourea (193 mg), triethylamine (132 mg), mercuric chloride (217 mg) and DMF (8 ml). The crude product was purified on a silica gel column eluting with 15% ethyl acetate –85% hexane to afford 303 mg of a colorless viscous oil. NMR was consistent with the proposed structure.

EXAMPLE 11

3-[[[3-[(aminoiminomethyl)amino]phenyl]methyl]amino]-β-phenylbenzenepropanoic acid, trifluoroacetate salt

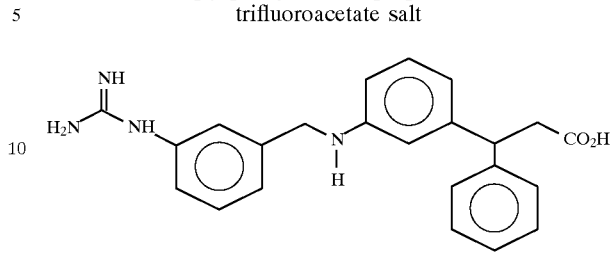

The reaction was run as described in Example 1 using the product from Example V (280 mg) and a 1:1 TFA:methylene chloride solution (15 ml). The crude product was purified as previously described to afford 205 mg of white solid. NMR was consistent with the proposed structure.

Analysis Calculated for $C_{23}H_{24}N_4O_2 \cdot 2.5TFA \cdot 1.2H_2O$

C, 48.38; H, 4.19; N, 8.06.

Found: C, 48.18; H, 4.03; N, 8.06.

EXAMPLE 12

Synthesis of 1,1-dimethylethyl 3-[[[3-[[[(phenylmethyl)amino]carbonyl]amino]phenyl]sulfonyl]amino]-β-phenylbenzenepropanoate, monohydrate

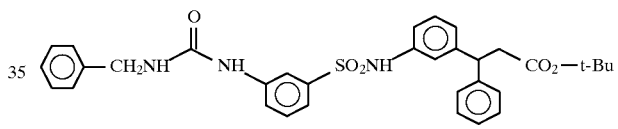

A solution of the product from Example H (400 mg), benzyl isocyanate (600 mg) (Aldrich) and toluene (5 ml) was refluxed for 3 hours. The reaction mixture was cooled to room temperature and the solvent removed in vacuo. The residue was purified on a silica gel column eluting with 40% ethyl acetate –60% hexane to afford 208 mg of white solid. NMR was consistent with the proposed structure.

EXAMPLE 13

Synthesis of 3-[[[3-[[[(phenylmethyl)amino]carbonyl]amino]phenyl]sulfonyl]amino]-β-phenylbenzenepropanoic acid, monohydrate

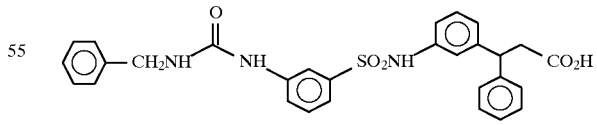

The reaction was run as described in Example 1 using the product from Example 12 (190 mg) to afford 150 mg of white solid. NMR was consistent with the proposed structure.

Analysis Calculated for $C_{29}H_{27}N_3O_5S \cdot 1.0 H_2O$:

C, 63.60; H, 5.34; N, 7.67; S, 5.85.

Found: C, 63.64; H, 5.17; N, 7.48; S, 5.76.

EXAMPLE 14

1,1-Dimethylethyl 3-[[[3-[[(cyanoimino)(methylthio)methyl]amino]phenyl]sulfonyl]amino]-β-phenylbenzenepropanoate

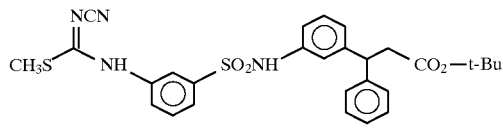

A mixture of the product from Example H (395 mg), N-cyano-S,S dimethyldithio iminocarbonate (266 mg) (Aldrich) and pyridine (2.5 ml) was refluxed for 3.5 hours in a hood. The reaction mixture was cooled to room temperature and the solvent removed under a stream of nitrogen. The residue was purified on a silica gel column eluting with 1:1 ethyl acetate-hexane to afford 336 mg of white solid. NMR was consistent with the proposed structure.

EXAMPLE 15

1,1-dimethylethyl 3-[[[3-[[amino(cyanoimino)methyl]amino]phenyl]sulfonyl]amino]-β-phenylpropanoate

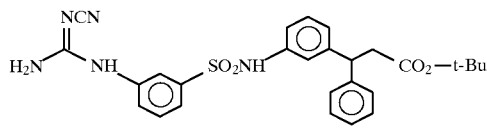

A solution of the product from Example 14 (315 mg), ethanol (8 ml) and concentrated ammonium hydroxide solution (5 ml) was heated at 800 for 16 hours. The reaction mixture was cooled to room temperature and the solvent removed under a stream of nitrogen. The crude product was purified on a silica gel column eluting with 100% ethyl acetate to afford 257 mg of white solid. NMR was consistent with the proposed structure.

EXAMPLE 16

Synthesis of 3-[[[3-[[amino[(aminocarbonyl)imino]methyl]amino]phenyl]sulfonyl]amino]-β-phenylbenzenepropanoic acid, trifluoroacetate salt

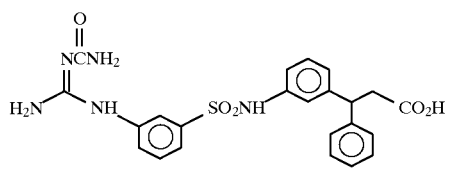

The reaction was run as described in Example 1 using the product from Example 15 (225 mg) to afford 195 mg of white solid. NMR was consistent with the proposed structure.

Analysis Calculated for $C_{23}H_{23}N_5O_5S \cdot 1.25TFA$.

C, 49.08; H, 3.92; N, 11.22; S, 5.14.

Found: C, 49.23; H, 4.23; N, 11.08; S, 5.23.

EXAMPLE AV

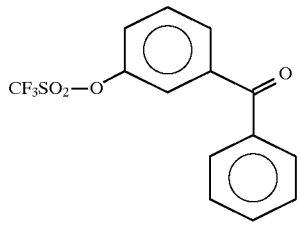

A solution of trifluoromethane sulfonic anhydride (12.1 g) (Aldrich) in methylene chloride (20 ml) was prepared in a dry flask under nitrogen. The reaction mixture was cooled to −70° and a solution of of 3-hydroxy benzophenone (8.5 g) (Aldrich) in methylene chloride (30 ml) was rapidly added, followed by the immediate addition of triethylamine (4.3 g). The reaction mixture was allowed to warm to room temperature and stirred for 16 hours. The reaction mixture was then partitioned between ethyl acetate and saturated sodium chloride solution. The aqueous portion was extracted with additional ethyl acetate and the combined organic extracts were dried ($Na_2SO_4$) and concentrated. The crude product was purified on a silica gel column eluting with 20% ethyl acetate −80% hexane to afford 10.7 g of yellow viscous liquid. NMR was consistent with the proposed structure.

EXAMPLE AL

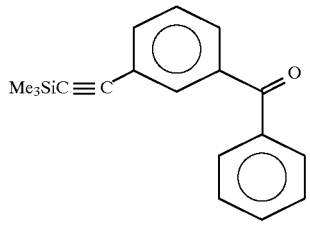

A mixture of the product from Example AV (10.6 g), trimethylsilyl acetylene (3.9 g) (Aldrich), diethylamine (130 ml) (Aldrich), bis(triphenylphosphine)-palladium(II) dichloride (450 mg) (Aldrich) and copper(I)iodide (32 mg) (Aldrich) was placed in a dry flask under argon. The reaction mixture was stirred at room temperature for 16 hours and then the solvent was removed under a stream of nitrogen. The residue was purified on a silica gel column eluting with 5% ethyl acetate −95% hexane to afford 4.6 g of viscous golden oil. NMR was consistent with the proposed structure.

EXAMPLE AM

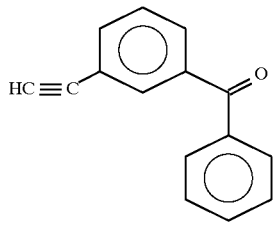

A solution of the product from Example AL (4.6 g) was stirred with 1N methanolic potassium hydroxide solution (17 ml) at room temperature for 1 hour. The reaction mixture was concentrated and the residue was purified on a silica gel column eluting with 5% ethyl acetate −95% hexane to afford 3.4 g of golden liquid. NMR was consistent with the proposed structure.

EXAMPLE AN

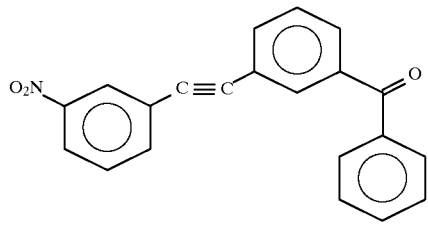

A mixture of the product from Example AM (3.2 g), 3-bromonitrobenzene (2.5 g) (Fluka), bis(triphenylphosphine)-palladium(II)acetate (187 mg) (Aldrich) and triethylamine (15 ml) was placed in a Parr bottle and degassed with argon. The bottle was stoppered and heated in an oil bath at 80° for 16 hours. The reaction mixture was cooled and the solvent removed under a stream of nitrogen. The black residue was partitioned between ethyl acetate and water and the aqueous portion was extracted with additional ethyl acetate. The combined organic extracts were washed with saturated sodium chloride solution (2×), dried ($Na_2SO_4$) and concentrated. The crude product was purified on a silica gel column eluting with 20% ethyl acetate −80% hexane to afford 2.2 g of yellow solid. NMR was consistent with the proposed structure.

EXAMPLE W

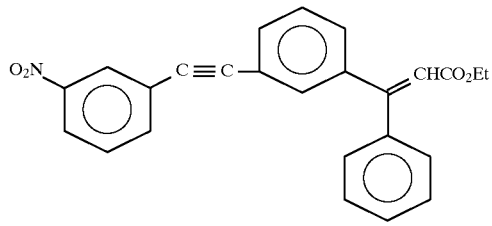

In a dried flask under nitrogen was placed a 60% oil dispersion of sodium hydride (290 mg). The dispersion was washed (3×) with hexane and decanted and then the hydride was suspended in dry THF (10 ml) and chilled to 0°. A solution of triethylphosphonate (1.6 g) (Aldrich) in dry THF (15 ml) was added dropwise and the reaction stirred at 0° for 30 minutes. A solution of the product from Example AN (2.2 g) in dry THF (10 ml) was added dropwise at 0° and then the reaction mixture was allowed to warm to room temperature and stirred for 16 hours. The reaction mixture was partitioned between ethyl acetate and 0.5N hydrochloric acid. The aqueous portion was extracted with additional ethyl acetate and the combined organic extracts were washed with saturated sodium chloride solution, dried ($Na_2SO_4$), and concentrated. The crude product was purified on a silica gel column eluting with 15% ethyl acetate −85% hexane to afford 2.3 g of viscous golden oil. NMR was consistent with the proposed structure.

EXAMPLE X

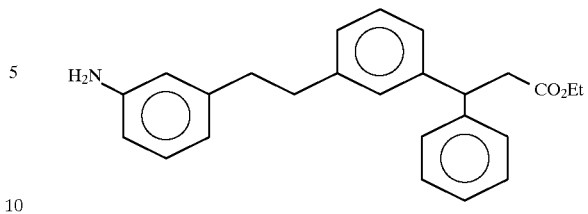

A solution of the product from Example W (810 mg) in ethanol (5 ml) and THF (5 ml) was hydrogenated under a 5 psi atmosphere of hydrogen at room temperature for 23.1 hours using 4% palladium on carbon catalyst. The reaction mixture was concentrated and the residue was purified on a silica gel column eluting with 40% ethyl acetate −60% hexane to afford 615 mg of oil. NMR was consistent with the proposed structure.

EXAMPLE Y

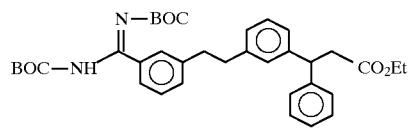

The reaction was run as described in Example I using the product from Example X (450 mg), bis-t-butoxycarbonylthiourea (346 mg), triethylamine (253 mg); mercuric chloride (380 mg) and DMF (15 ml). The crude product was purified on a silica gel column eluting with 10% ethyl acetate −90% hexane to afford 460 mg of a colorless viscous oil. NMR was consistent with the proposed structure.

EXAMPLE 17 ethyl 3-[2-[3-[(aminoiminomethyl)amino]phenyl] ethyl]-β-phenylbenzenepropanoate

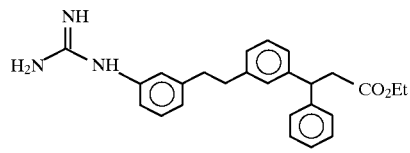

The reaction was run and the crude product purified as described in Example 1 using the product from Example Y (440 mg) to afford 270 mg of colorless glass. NMR was consistent with the proposed structure.

EXAMPLE 18

3-[2-[3-[(aminoiminomethyl)amino]phenyl]ethyl]-β-phenylbenzenepropanoic acid

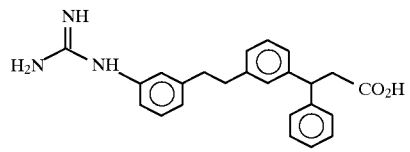

A solution of 250 mg of the product from Example 17 (250 mg), methanol (6 ml) and 1N lithium hydroxide (3 ml)

was stirred at room temperature for 16 hours. The reaction mixture was concentrated and the residue was treated with a solution of methylene chloride (7 ml) and TFA (3 ml) at room temperature for 5 minutes. The solvent was removed in vacuo and the crude product was purified via reverse phase HPLC using a water (0.5% TFA) and acetonitrile gradient as eluant to afford 210 mg of white powder. NMR was consistent with the proposed structure.

Analysis Calculated for $C_{24}H_{25}N_3O_2 \cdot 1.25TFA$.

C, 60.05; H, 4.99; N, 7.93.
Found: C, 59.68; H, 5.07; N, 7.97.

EXAMPLE Z

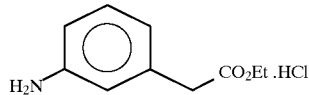

3-Aminophenylacetic acid (3 g, 19.8 mmol) was dissolved in dry ethanol (60 mL) at 0° C. and a stream of hydrogen chloride gas was bubbled into the solution for 15 minutes. The solvent was removed under reduced pressure to give desired product.

EXAMPLE AA

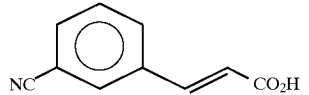

A mixture of 3-cyanobenzaldehyde (1.004 g, 7.6 mmol), malonic acid (0.880 g, 8.4 mmol), and pyridine (0.10 mL, 1.3 mmol) in absolute ethanol (2 mL) was heated to 100° C. (bath) under argon. Upon heating, the mixture became a solution; after 20–30 minutes, a white precipitate formed. The reaction was monitored by TLC (10% $MeOH/CH_2Cl_2$). After 21.5 hours, the reaction mixture was allowed to cool to room temperature and the white precipitate was collected by vacuum filtration. The solid was slurried with hot EtOH and collected by filtration to give the product as a white solid, (0.903 g, 69% yield). NMR was consistent with the proposed structure.

EXAMPLE AB

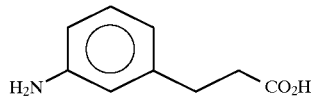

The compound of Example AA was dissolved in a MeOH (15 mL)/$NH_4OH$ (7.5 mL) mixture and hydrogenated with W-2 Raney Ni in a Parr Shaker (60 psi, 25° C.) for 2.5 hours. The catalyst was filtered and the purple filtrate concentrated in vacuo. The green solid residue was dissolved in 1M HCl and concentrated in vacuo to give a white/green solid. The solid was purified by slurrying with 9:1 $CH_3CN$/MeOH mixture. The white undissolved solid was collected by vacuum filtration to give the desired product (0.664 g, 59% yield). NMR was consistent with the proposed structure.

EXAMPLE AC

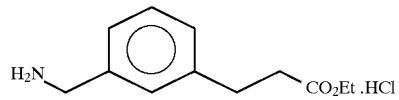

A mixture of the compound of Example AB in absolute EtOH (50 mL) was cooled to 0° C. and HCl gas was bubbled into the mixture for 20 minutes. The resulting green/blue solution was allowed to stir for 2 hours. An aliquot was removed and concentrated in vacuo. $^H$NMR showed the reaction to be complete. The reaction was concentrated in vacuo to give a slightly green-tinted white solid (0.710 g, quantitative.) NMR was consistent with the proposed structure.

EXAMPLE 19

Synthesis of ethyl 3-[[[[3-(cyano)phenyl]carbonyl]amino]methyl]benzenepropanoate, diacetate salt

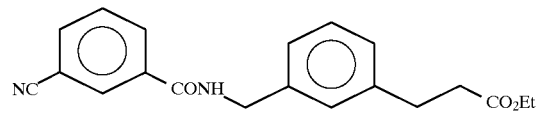

A solution of 3-cyanobenzoic acid (0.447 g, 3.0 mmol) and 1-methyl piperidine (0.37 mL, 3.0 mmol) in $CH_2Cl_2$ (15 mL) was cooled to 9° C. Isobutylchloroformate (0.39 mL, 3.0 mmol) was added slowly under argon and the reaction stirred for another 5 minutes. A solution of the compound of Example AC (0.710 g, 2.9 mmol) and 1-methyl piperidine (0.37 mL, 3.0 mmol) in $CH_2Cl_2$ (3 mL) was then added and the ice bath immediately removed. The reaction was allowed to stir at room temperature for 2 hours. The reaction was concentrated in vacuo to give a green solid residue. The residue was partitioned between EtOAc (25 mL) and water (25 mL). The organic layer was collected, washed with 1M HCl (1×25 mL), saturated $NaHCO_3$ (1×25 mL), and brine (1×25 mL), and then dried over $MgSO_4$. Concentration in vacuo gave the crude product as a pale yellow oil (1.17 g). The product was purified by column chromatography (75 g silica gel, 3% $MeOH/CH_2Cl_2$) to give a yellow/white solid (0.491 g, 43% yield). NMR was consistent with the proposed structure.

EXAMPLE AD

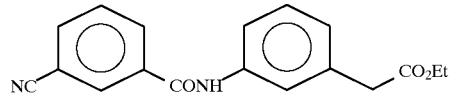

The above compound was synthesized under conditions similar to Example 19, replacing the compound of Example AC with the compound of Example Z.

Analysis Calculated for $C_{18}H_{16}N_2O_3$:

C, 69.31; H, 5.30; N, 8.98.
Found: C, 69.15; H, 5.36; N, 8.86.

EXAMPLE 19A ethyl 3-[[[3-[amino(hydroxyimino)methyl]phenyl]carbonyl]amino]methyl]benzenepropanoate

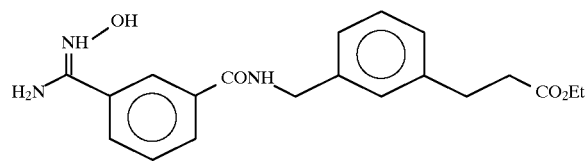

A solution of the compound of Example 19 (0.491 g, 1.3 mmol), hydroxylamine hydrochloride (0.092 g, 1.3 mmol), and triethylamine (0.18 mL, 1.3 mmol) in absolute EtOH (10 mL) was heated to reflux (86°–90° C.). After 5 hours, TLC [1:1 EtOAc/hexane (10 mL) and 5 drops of AcOH] showed that starting material was still present. Additional hydroxylamine hydrochloride (0.038 g, 0.5 eq) and triethylamine (0.09 mL) was added. After 40 minutes, the TLC showed no difference. The reaction was concentrated in vacuo to give a pale yellow oil (0.53 g). The oil was purified by column chromatography [50 g silica gel, 3% MeOH/CH$_2$Cl$_2$ (500 mL) followed by 10% MeOH/CH$_2$Cl$_2$ (150 mL)] and the desired product was collected in 85% yield (0.42 g). NMR was consistent with proposed structure.

EXAMPLE 20 ethyl 3-[[[3-[amino(hydroxyimino)methyl]phenyl]carbonyl]amino]benzeneacetate

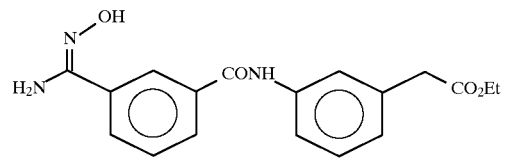

The above compound was synthesized under conditions similar to Example 19A, replacing the compound of Example 19 with the compound of Example AD.

Analysis Calculated for C$_{18}$H$_{19}$N$_3$O$_4$:
C, 63.33; H, 5.61; N, 12.31.
Found: C, 63.08; H, 5.90; N, 12.02.

EXAMPLE 21 ethyl 3-[[[[(3-(aminoiminomethyl)phenyl]carbonyl]amino]methyl]benzenepropanoate

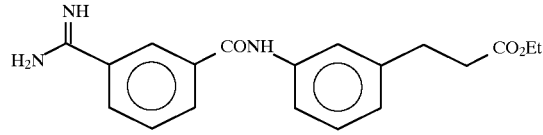

The compound of Example 19A (0.42 g, 1.1 mmol) was dissolved in ACOH and hydrogenated with 4% Pd/C (53% wet, 0.050 g) in a Parr Shaker (60 psi, 60C). The catalyst was filtered off and the filtrate concentrated in vacuo to give a white solid (pink tint). The solid was slurried with acetonitrile and the resulting white solid was collected by vacuum filtration (0.347 g, 89% yield).

Analysis Calculated for C$_{20}$H$_{23}$N$_3$O$_3$.2.0 ACOH: C, 60.80; H, 6.60; N, 8.87. Found: C, 60.17; H, 6.47; N, 8.89. M+=353.

EXAMPLE 22 ethyl 3-[[[3-[aminoiminomethyl]phenyl]carbonyl]amino]benzeneacetate

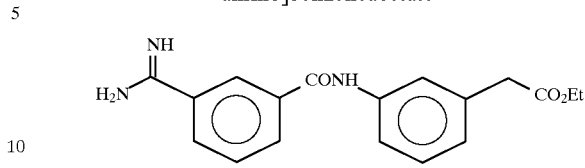

The compound of Example 20 was reduced under conditions similar to conditions for Example 21, replacing the compound of Example 19A with the compound of Example 20.

Analysis Calculated for C$_{18}$H$_{19}$N$_3$O$_3$.1.3 AcOH: C, 61.33; H, 6.05; N, 10.42. Found: C, 61.09; H, 6.23; N, 10.29.

EXAMPLE 23

Synthesis of 3-[[[[3-(aminoiminomethyl)phenyl]carbonyl]amino]methyl]benzenepropanoic acid, trifluoroacetate salt

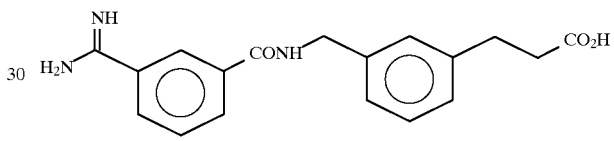

To a mixture of the compound of Example 21 (0.200 g, 0.57 mmol) in 1M phosphate buffer was added esterase from porcine liver (Sigma, 0.5 mL) at room temperature. The reaction was stirred for 18 hours and then concentrated in vacuo. A solution of 1M HCl (2–4 mL)/CH$_3$CN (4 mL) was added to the resulting residue and the undissolved solid filtered. The filtrate was collected, concentrated in vacuo, and purified by HPLC—Method 1 to give the desired product as a white solid (0.09 g, 36% yield).

Analysis Calculated for C$_{18}$H$_{19}$N$_3$O$_3$.1.0 TFA+0.2 H$_2$O: C, 54.23; H, 4.64; N, 9.49. Found: C, 54.06; H, 4.60; N, 9.46. MH+=326.

EXAMPLE 24

3-[[[3-(aminoiminomethyl)phenyl]carbonyl]amino]benzeneacetic acid

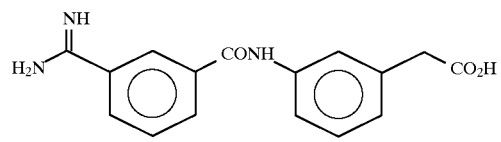

The above compound was synthesized under conditions similar to the conditions described in Example 23, replacing the compound of Example 21 with the compound of Example 22.

Analysis Calculated for C$_{16}$H$_{15}$N$_3$O$_3$.1TFA.1H$_2$O: C, 50.34; H, 4.23; N, 9.79. Found: C, 50.21; H, 4.07; N, 9.50.

EXAMPLE AE

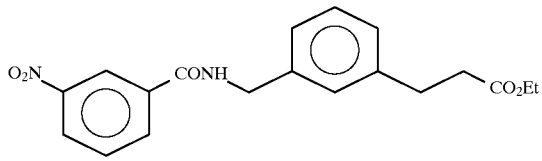

A solution of 3-nitrobenzoic acid (2.42 g, 9.95 mmol) and 1-methyl piperidine (1.2 mL, 9.95 mmol) in $CH_2Cl_2$ (55 mL) was cooled to 0° C. and isobutyl chloroformate (1.3 mL, 9.95 mmol) was added under argon. The reaction was allowed to stir for 5 minutes before adding a solution of the compound of Example AC (2.42 g, 9.95 mmol) and 1-methyl piperidine (1.2 mL, 9.95 mmol) in $CH_2Cl_2$ (10 mL). The flask containing the compound of Example AC was rinsed with $CH_2Cl_2$ (1 mL) and the rinse added to the reaction. The ice bath was removed after addition and the reaction was allowed to stir at room temperature over 24 hours. The reaction was concentrated in vacuo and the residue partitioned between EtOAc and water. The organic layer was washed with 1M HCl, followed by $NaHCO_3$ and brine. The organic layer was collected, dried over $MgSO_4$, and concentrated in vacuo to give a pale yellow oil. The crude reaction mixture was purified by column chromatography [300 g silica gel, 2:1 hexane/EtOAc (1:1)] to give the desired product as a white solid (2.87 g, 81% yield). NMR was consistent with the proposed structure.

EXAMPLE AF

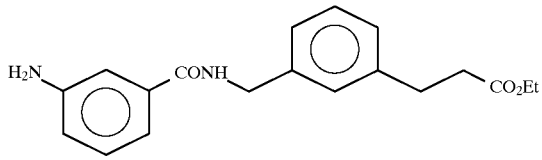

The compound of Example AE was hydrogenated (4% Pd/C, EtOH, 5 psi, room temperature, 1.5 hours) and the filtrate concentrated in vacuo to give a yellow oil (2.095 g, 82% yield). NMR was consistent with the proposed structure.

EXAMPLE 25

Synthesis of 3-[[[[3-[(aminothioxomethyl)amino] phenyl]carbonyl]amino]methyl]benzenepropanoic acid

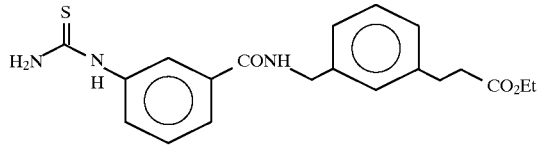

A solution of the compound of Example AF (0.49 g, 1.5 mmol) in $CH_3CN$ (10 mL) was cooled to 0° C. and DMAP (0.021 g, 0.15 mmol) was added under argon followed by benzoyl isothiocyanate (0.25 g, 1.5 mmol). After 30 minutes, the reaction solidified and stirring became difficult. The reaction was allowed to warm to room temperature After 2 hours, additional benzoyl isothiocyanate (0.05 mL) was added. Within 15 minutes, the reaction appeared complete as monitored by TLC (5% $MeOH/CH_2Cl_2$). The reaction was concentrated in vacuo and the residue was diluted with MeOH (7 mL)/water (7 mL). Potassium carbonate (0.21, 1.5 mmol) was added at room temperature and the reaction stirred over 17 hours. The reaction mixture was worked-up with water and extracted with EtOAc. The reaction appeared by TLC to be incomplete. The residue was submitted to heating (84° C.) with potassium carbonate (2 equivalents) for 1.5 hours. The reaction was cooled to room temperature and concentrated in vacuo. The residue was suspended in water and extracted with EtOAc (2×50 mL). The organic layers were washed with brine and dried over $MgSO_4$. Concentration in vacuo gave the desired product as a yellow oil. The oil was purified by column chromatography [50–75 g silica gel, 2% $MeOH/CH_2Cl_2$ (1.5 1)] to give the desired product as a white solid (0.131 g, 23% yield). The $^HNMR$ showed the solid to be a mixture of the ethyl ester and the methyl ester.

EXAMPLE 26

3-[[[[3-[(aminothioxomethyl)amino]phenyl] carbonyl]amino]methyl]benzenepropanoic acid

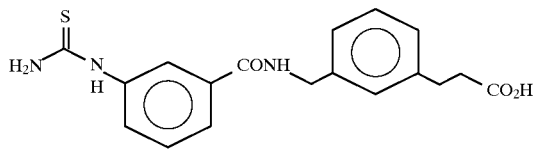

The compound of Example 25 (0.131 g, 0.34 mmol) was dissolved in MeOH (2 mL) and 1M LiOH (0.68 mL) was added. The reaction was stirred at room temperature over 16 hours. The reaction was concentrated in vacuo to give a white solid. The solid was dissolved in a small amount of H20 and acidified with 1 drop of TFA. The mixture was concentrated in vacuo and the residue was purified by HPLC—Method 1 to give a white solid (0.055 g, 45% yield).

Analysis Calculated for $C_{18}H_{19}N_3O_3 \cdot 0.45\ H_2O$: C, 59.15; H, 5.49; N, 11.50. Found: C, 58.85; H, 5.10; N, 11.75. M+=357.

EXAMPLE 28

Synthesis of ethyl 3-[[[[3-[(aminocarbonyl)amino] phenyl]carbonyl]amino]methyl]benzenepropanoate

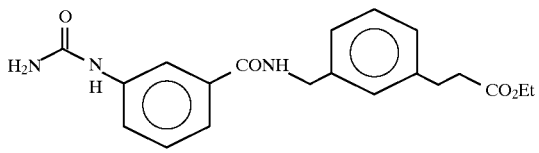

A mixture of the compound of Example AF (0.447 g, 2.2 mmol) and acetic acid (1 mL) in water (2 mL) was heated to 38° C. (bath). A solution of potassium cyanate (0.343 g, 4.4 mmol) in water (2 mL) was then added slowly. The reaction became cloudy and a white precipitate resulted. The reaction was allowed to cool to room temperature and stirred for 1.5 hours. The reaction was monitored by TLC (10% $MeOH/CH_2Cl_2$). The white solid was collected by vacuum filtration and washed with water (0.469 g, 58% yield).

Analysis Calculated for $C_{20}H_{23}N_3O_3 \cdot 0.1\ H_2O$ TFA: C, 64.71; H, 6.30; N, 11.32. Found: C, 64.52; H, 6.37; N, 11.11. M+=369.

EXAMPLE 29

Synthesis of 3-[[[[3-[(aminocarbonyl)amino]phenyl]carbonyl]amino]methyl]benzenepropanoic acid

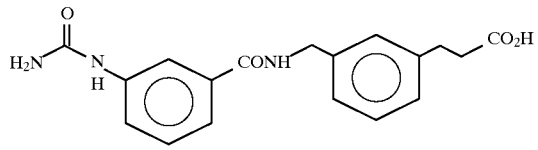

The compound from Example 28 was hydrolyzed using the method described in Example 26. After acidifying with TFA, the resulting white precipitate was filtered off and washed with water (3X) and ether (1X). (0.261 g, 89% yield).

Analysis Calculated for $C_{18}H_{19}N_3O_4 \cdot 0.3\ H_2O$: C, 62.35; H, 5.70; N, 12.12. Found: C, 62.32; H, 5.45; N, 12.23. M+=341.

EXAMPLE 30

Synthesis of ethyl 3-[[[[3-[[[(phenylmethyl)amino]carbonyl]amino]phenyl]carbonyl]amino]methyl]benzenepropanoate

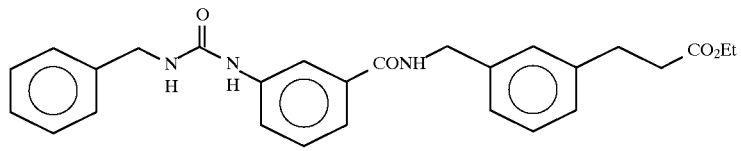

To a solution of benzyl isocyanate (0.12 g, 0.88 mmol) in $CH_2Cl_2$ (6 mL) was added a solution of the compound of Example AF (0.30 g, 0.92 mmol) in $CH_2Cl_2$ (2 mL) under argon. The flask containing the compound of Example AF was rinsed with $CH_2Cl_2$ (1 mL) and added to the reaction. The reaction was stirred at room temperature for 17 hours. The reaction was concentrated in vacuo and ether added to the yellow oil. Upon addition, the oil solidified. The resulting white solid was collected by vacuum filtration and washed with a small amount of ether (0.303 g, 75% yield).

Analysis Calculated for $C_{27}H_{29}N_3O_4$: C, 70.57; H, 6.36; N, 9.14. Found: C, 70.59; H, 6.74; N, 9.13. M+=459.

EXAMPLE 31

Synthesis of 3-[[[[3-[[[(phenylmethyl)amino]carbonyl]amino]phenyl]carbonyl]amino]methyl]benzenepropanoic acid

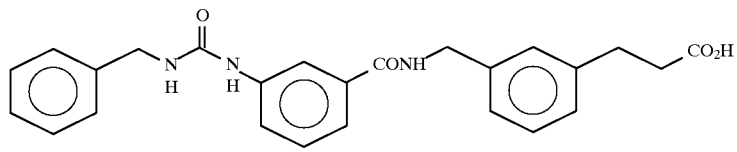

The compound of Example 30 was hydrolyzed using the method described in Example 26. After acidifying with TFA, the resulting white precipitate was filtered off and washed with water (3X) and ether (1X). The desired product was collected as a cream-colored solid (0.115 g, 89% yield).

Analysis Calculated for $C_{25}H_{25}N_3O_4 \cdot 0.1\ H_2O$: C, 69.30; H, 5.86; N, 9.70. Found: C, 69.17; H, 5.81; N, 9.63. MH+=432.

EXAMPLE AG

Synthesis of

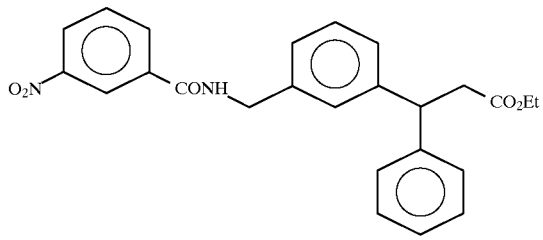

The compound from Example 37, Step D, (0.8 g, 2.8 mmol) was coupled with 3-nitrobenzoic acid under similar conditions to the conditions described in Example AE using $CH_2Cl_2$ as the solvent. The crude material was purified by column chromatography (100 g silica, 40% EtOAc/hexane) to give the desired product as a pale yellow oil (0.969 g). NMR was consistent with the proposed structure.

EXAMPLE AH

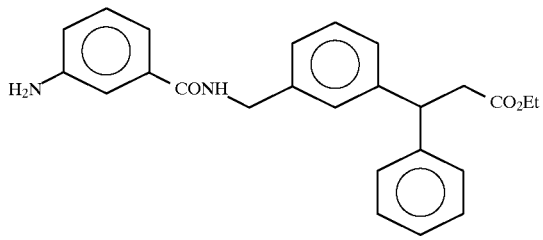

The compound of Example AG (0.969 g, 2.2 mmol) was dissolved in EtOH and hydrogenated with 4% Pd/C in a Parr Shaker (5 psi) at room temperature for 16 hours. The catalyst was filtered off and the filtrate concentrated in vacuo to give the product as a brown oil (0.577 g). NMR was consistent with the proposed structure.

EXAMPLE 32 ethyl 3-[[[[3-[[[(phenylmethyl)amino]carbonyl]
amino]phenyl]carbonyl]amino]methyl]-β-
phenylbenzenepropanoate

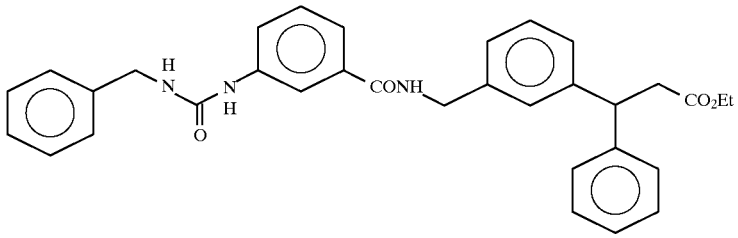

The compound of Example AH (0.25 g, 0.62 mmol) was treated with benzyl isocyanate under conditions described similar to the conditions described in Example 30. The desired product was collected as an off-white solid (0.314 g).

Analysis Calculated for $C_{33}H_{33}N_3O_4 \cdot 0.5\ H_2O$: C, 72.77; H, 6.29; N, 7.71. Found: C, 72.66; H, 6.26; N, 7.68. MH+=536.

EXAMPLE 33

3-[[[[3-[[[(phenylmethyl)amino]carbonyl]amino]
phenyl]carbonyl]amino]methyl]-β-
phenylbenzenepropanoic acid

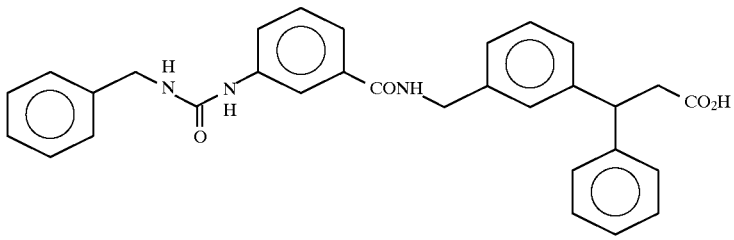

The compound of Example 32 (0.226 g, 0.4 mmol) was hydrolyzed under the same conditions as described in Example 26 to give the desired product as a white solid (0.118 g).

Analysis Calculated for $C_{31}H_{29}N_3O_4 \cdot 0.4\ H_2O$: C, 72.33; H, 5.83; N, 8.16. Found: C, 72.23; H, 5.59; N, 7.96. MH+=508.

EXAMPLE AI

A solution of 3-aminobenzoic acid (40.47 g, 0.29 mol), 3,5-dimethylpyrazole carboxamidine nitrate (88.24 g, 0.44 mol), and diisopropylethylamine (76 mL, 0.44 mol) in dioxane (300 mL)/water (150 mL) was heated to reflux for 1 hour, 15 minutes. A brown precipitate resulted. The reaction was stirred at room temperature for over 48 hours. The reaction mixture was filtered and the resulting lavender solid rinsed with dioxane (150 mL) followed by 1:1 dioxane/water (100 mL). The solid was dried in vacuo and then treated with a mixture of ether (400 mL)/acetonitrile(100 mL)/4N HCl/Dioxane (100 mL). To this slurry was added 20% HCl (1 mL). The mixture was stirred at room temperature over 18 hours. The undissolved solid was filtered off and washed with ether (2X). The desired product was collected as a pale purple solid (28.15 g, 45% yield). NMR was consistent with the proposed structure.

EXAMPLE 34

Synthesis of ethyl 3-[[[[3-[(aminoiminomethyl)
amino]phenyl]carbonyl]amino]methyl]
benzenepropanoate, trifluoroacetate salt

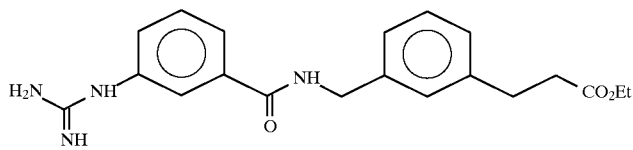

A solution of the compound of Example AI (0.494 g, 2.3 mmol) and 1-methyl piperidine (0.28 mL, 2.3 mmol) in DMF (5 mL) was cooled to 0° C. and isobutyl chloroformate (0.30 mL, 2.3 mmol) was added under argon. The reaction was allowed to stir for 5 minutes before adding a mixture of the compound of Example AC (0.499 g, 2.3 mmol) and 1-methyl piperidine (0.28 mL, 2.3 mmol) in DMF (2 mL). The flask containing the compound of Example AC was rinsed with DMF (2 mL) and the rinse added to the reaction. The ice bath was removed and the reaction was allowed to stir at room temperature over 24 hours. The reaction time varied from 16–24 hours. The reaction was concentrated in vacuo and the residue purified by HPLC-Method 1 to give the desired product as a colorless oil. Upon azeotroping with $CH_3CN$, the oil solidified and the white solid was collected by vacuum filtration (0.149 g, 14% yield).

Analysis Calculated for $C_2OH_{24}N_4O_3 \cdot 1.4$ TFA: C, 51.86; H, 4.85; N, 10.61. Found: C, 51.57; H, 4.99; N, 11.01. MH+=368.

EXAMPLE 35

Synthesis of 3-[[[[3-[(aminoiminomethyl)amino]phenyl]carbonyl]amino]methyl]benzenepropanoic acid, trifluoroacetate salt

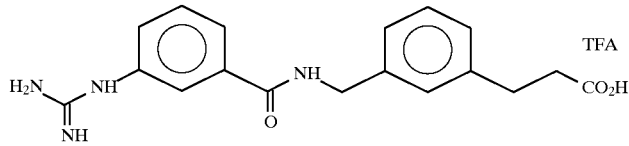

The compound of Example AB (0.54 g, 2.2 mmol) was coupled with the compound of Example AI according to the procedure described in Example 34. The crude material was purified by HPLC-Method 1 to give a yellow oil (0.212 g).

Analysis Calculated for $C_{18}H_{20}N_4O_3 \cdot 1.0$ TFA: C, 52.86; H, 4.66; N, 12.33. Found: C, 52.61; H, 4.44; N, 12.35. M+=340.

EXAMPLE AW

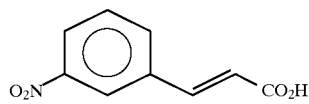

3-Nitrobenzaldehyde (2.98 g, 20 mmol) was treated with malonic acid (2.376 g, 22 mmol) under the same reaction conditions described in Example AA. Recrystallization from EtOH (10 mL) gave the product as tan needles (0.873 g). NMR was consistent with the proposed structure.

EXAMPLE AX

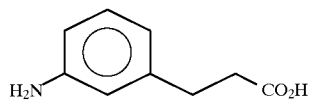

The compound of Example AW (0.860 g, 4.45 mmol) was reduced under conditions similar to conditions for Example AF. The product was isolated as a yellow oil (0.76 g). NMR was consistent with the proposed structure.

EXAMPLE 36

3-[[[3-[(aminoiminomethyl)amino]phenyl]carbonyl]amino]benzenepropanoic acid, trifluoroacetate salt

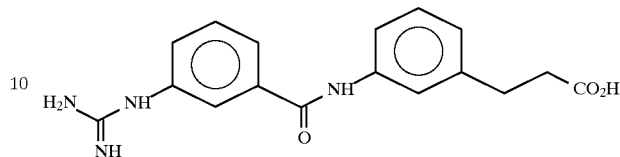

The above compound was synthesized following the same synthetic method as described in Example 34 replacing the compound of Example AC with the compound of Example AX.

Analysis Calculated for $C_{17}H_{18}N_4O_3 \cdot 1.0$ TFA: C, 51.82; H, 4.35; H, 12.72. Found: C, 51.52; H, 4.37; N, 12.83. M+=326.

EXAMPLE 37

Synthesis of ethyl 3-[[[[3-[(aminoiminomethyl)amino]phenyl]carbonyl]amino]methyl]-β-phenylbenzenepropanoate, trifluoroacetate salt

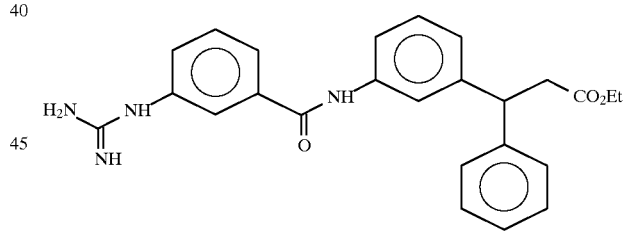

Step A

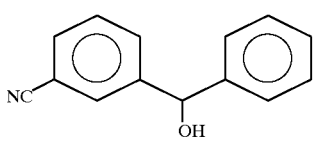

A solution of 3-cyanobenzaldehyde (3.00 g, 22.9 mmol) in distilled THF (30 mL) was cooled to −78° C. and a 1M solution of phenylmagnesium bromide in THF (45 mL) was added slowly over 10 minutes under argon. The resulting light brown reaction mixture was allowed to warm slowly to room temperature in the dry ice bath over 2 hours. The purple reaction was stirred at room temperature for an additional 2 hours, then quenched with saturated $NH_4Cl$ (40 mL). The mixture was extracted with ether (50 mL) and dried over MgSO$_4$. Concentration in vacuo gave an orange oil (5.52 g, quantitative yield). NMR was consistent with the proposed structure.

Step B

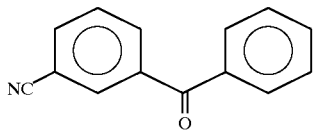

To a mixture of the compound of Step A (3.250 g, 15.5 mmol) and activated 4A molecular sieves in CH$_2$Cl$_2$ (60 mL) was added pyridinium dichromate (6.007 g, 15.5 mmol) at room temperature The mixture was stirred under argon for 21.5 hours. The reaction was diluted with ether and filtered (2X) through florisil (60–100 mesh). The filtrate was collected and concentrated in vacuo to give a white/yellow solid. The solid was purified by column chromatography [150 g silica gel, 20% EtOAc/hexane (1 L)] to give the desired product as a white solid (2.40 g, 77% yield). NMR was consistent with the proposed structure.

Step C

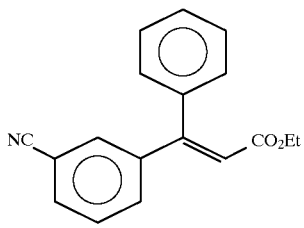

A suspension of 60% NaH in mineral oil (washed with hexane before use, 0.535 g, 12 mmol) in distilled THF (25 mL) was cooled to 0° C. and ethyl dimethylphosphonoacetate (1.9 mL, 12 mmol) was added very slowly under argon. Vigorous bubbling was observed and the reaction eventually became a white slurry. The reaction was allowed to stir at 0° C. for 1.5 hours before adding a solution of the compound of Step B (2.40 g, 12 mmol) in THF (10 mL). The flask containing the compound of Step B was rinsed with THF (5 mL) and added to the reaction. The reaction was allowed to warm to room temperature. After 4 hours, the reaction was quenched with water (50 mL) and extracted with EtOAc (2×60 mL). The organic layers were collected, dried over MgSO$_4$, and concentrated under a stream of N$_2$ to give the crude product (2.843 g, 83% yield). NMR was consistent with the proposed structure.

Step D

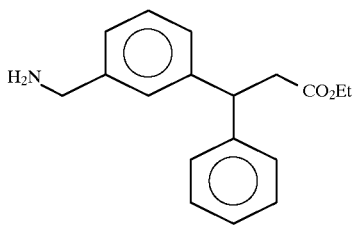

The compound of Step C (1.931 g, 6.8 mmol) was dissolved in i-PrOH/HCl and hydrogenated with 10% Pd/C in a Parr Shaker (60 psi) for 6 hours at room temperature. The catalyst was removed and the filtrate was concentrated in vacuo. The residue was partitioned between saturated NaHCO$_3$ and ether. The aqueous layer was back-extracted with ether. The organic layers were combined, dried over MgSO$_4$, and concentrated in vacuo to give a light brown oil (1.65 g, 86% yield). NMR was consistent with the proposed structure.

Step E

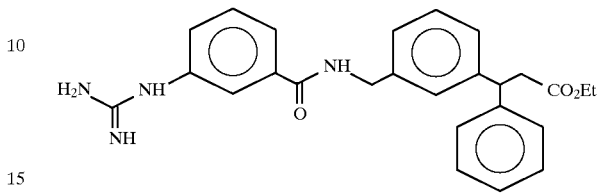

The compound of Step D (0.45 g, 1.6 mmol) was coupled with the compound of Example AI according to similar procedures described in Example 34 and purified by HPLC-Method 1 to give white sticky solid (0.400 g).

Analysis Calculated for C$_{26}$H$_{28}$N$_4$O$_3$·1.3 TFA+0.3 H$_2$O: C, 57.43; H, 5.04; N, 9.37. Found: C, 57.33; H, 4.74; N, 9.37. MH+=445.

EXAMPLE 38

Synthesis of 3-[[[[3-[(aminoiminomethyl)amino]phenyl]carbonyl]amino]methyl]-β-phenylbenzenepropanoic acid, trifluoroacetate salt

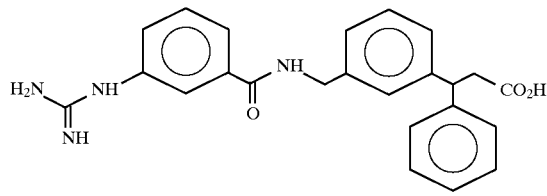

The compound of Example 37 (0.32 g, 0.72 mmol) was hydrolyzed under the conditions described in Example 26 and purified by HPLC-Method 1 to give the desired product as a white sticky solid (0.327 g).

Analysis Calculated for C$_{24}$H$_{24}$N$_4$O$_3$·1.6 TFA+0.6 H$_2$O: C, 53.58; H, 4.43; N, 9.19. Found: C, 53.41; H, 4.15; N, 9.22. MH+=417.

EXAMPLE AJ

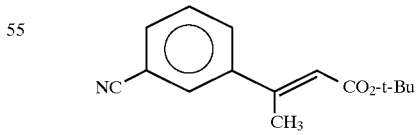

3-acetylbenzonitrile was treated with t-butyl P,P-dimethylphosphonoacetate under the same conditions as described in Example 37, Step C. The crude material was purified by column chromatography to give one pure isomer as a yellow oil (1.401 g, 42% yield). NMR was consistent with the proposed structure.

EXAMPLE AK

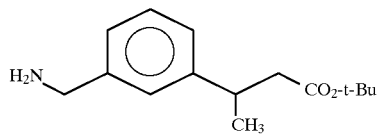

The compound of Example AJ was hydrogenated (i-PrOH+1N HCl, 10% Pd/C, 60 psi, room temperature, 1.5 hours) and the filtrate concentrated in vacuo. The solid residue was partitioned between saturated $NaHCO_3$ (25 mL) and ether (25 mL). The aqueous layer was back-extracted with ether (2×25 mL). The organic layers were combined, washed with brine, dried over $K_2CO_3$, and filtered through celite. Concentration of the filtrate in vacuo gave the desired product (free amine) as a yellow oil (0.401 g, 35% yield). NMR was consistent with the proposed structure.

EXAMPLE 39

Synthesis of 1,1-dimethylethyl 3-[[[[3-[(aminoiminomethyl)amino]phenyl]carbonyl]amino]methyl]-β-methyl)benzenepropanoate, trifluoroacetate salt

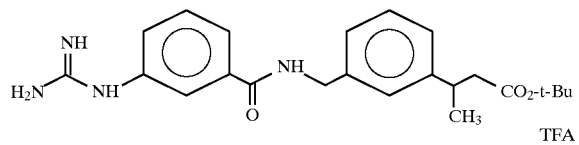

The compound of Example AK was coupled with the compound of Example AI under similar reaction conditions as described in Example 34. The crude material was purified by HPLC-Method 1 to give the desired product (0.29 g, 62% yield).

Analysis Calculated for $C_{23}H_{30}N_4O_3 \cdot 1.0$ TFA+0.7 $H_2O$: C, 55.90; H, 6.08; N, 10.43. Found: C, 55.73; H, 5.68; N, 10.27. M+=410.

EXAMPLE 40

Synthesis of 3-[[[[3-[(aminoiminomethyl)amino]phenyl]carbonyl]amino]methyl]-β-methylbenzenepropanoic acid, trifluoroacetate salt

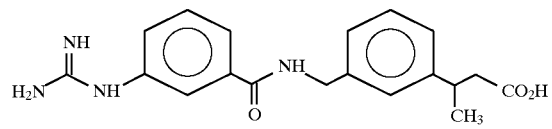

To a solution of the compound of Example 39 (0.163 g) in $CH_2Cl_2$ (4 mL) was added TFA (2 mL) at room temperature. The reaction was stirred for 8 hours, then concentrated in vacuo to give an orange oil. The crude product was purified by HPLC-Method 1 to give a white sticky solid (0.112 g).

Analysis Calculated for $C_{19}H_{22}N_4O_3 \cdot 1.4$ TFA+0.1 $H_2O$: C, 50.76; H, 4.61; N, 10.86. Found: C, 50.49; H, 4.52; N, 10.93.

EXAMPLE 41

Synthesis of ethyl 3-[[[[3-[(aminoiminomethyl)amino]phenyl]carbonyl]amino]methyl)-β-ethylbenzenepropanoate, trifluoroacetate salt

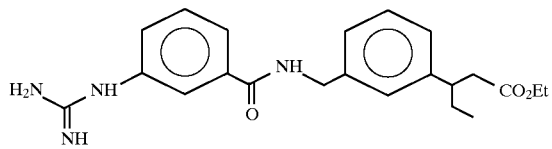

Step A

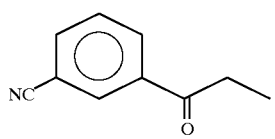

A solution of 3-acetylbenzonitrile (1.018 g, 7.0 mmol) in distilled THF (15 mL) was cooled to 0° C. A 1M LiHMDS solution in THF (7.6 mL) was added slowly under argon to give a red/brown solution. The ice bath was removed and the reaction allowed to stir at room temperature for 30 minutes. The solution was then transferred into a flask containing iodomethane (15 mL, 241 mmol) under an argon atmosphere. The reaction was monitored by TLC (20% EtOAc/hexane) and quenched with water after 1 hour at room temperature. The reaction was concentrated in vacuo and the residue partitioned between EtOAc (40 mL) and water (40 mL). The organic layer was collected, dried over $MgSO_4$, and concentrated in vacuo to give an orange/red oil (1.02 g). The crude mixture was purified by column chromatography [50 g silica gel, 10% EtOAc/hexane (700 mL)] to give the desired product as a yellow/white solid (0.372 g). The impure fractions were collected and repurified by plate chromatography to give the pure product as a pale yellow solid (0.585 g). [yield=86%.] NMR was consistent with the proposed structure.

Step B

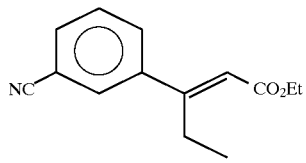

The ketone formed in Step A (0.959 g, 6.0 mmol) was treated with ethyl dimethylphosphonoacetate under conditions as described in Example 37, Step C. The product was isolated as a mixture of E and Z isomers in a 1:1 ratio (1.417 g). NMR was consistent with the proposed structure.

Step C

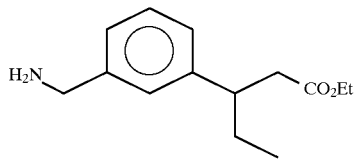

The compound from Step B (1.42 g, 6.2 mmol) was hydrogenated under conditions similar to those described in Example AK to give the desired product as a pale yellow oil (1.087 g, 75% yield). NMR was consistent with the proposed structure.

Step D

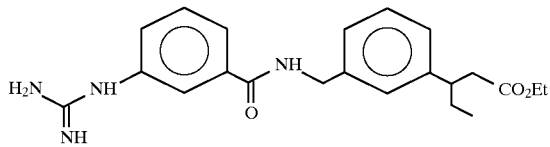

The product of Step C (1.087 g, 4.6 mmol) was coupled to the compound of Example AI according to conditions as described in Example 34. The residue was purified by HPLC-Method 1 to give the desired product as a yellow oil (1.571 g).

Analysis Calculated for $C_{22}H_{28}N_4O_3 \cdot 1.1$ TFA: C, 55.69; H, 5.62; N, 10.73. Found: C, 55.43; H, 5.33; N, 10.60. MH+=397.

EXAMPLE 42

Synthesis of 3-([[[3-[(aminoiminomethyl)amino]phenyl]carbonyl]amino]methyl]-β-ethylbenzenepropanoic acid, trifluoroacetate salt

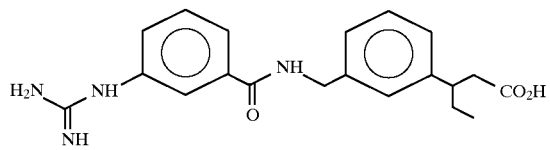

The product of Example 41 (1.4 g, 3.5 mmol) was hydrolyzed using the method described in Example 26. The crude material was purified by HPLC-Method 1 to give the desired product as a colorless oil (1.10 g).

Analysis Calculated for $C_{20}H_{24}N_4O_3 \cdot 1.1$ TFA+0.7 $H_2O$: C, 52.65; H, 5.27; N, 11.06. Found: C, 52.41; H, 4.93; N, 11.27. M+=368.

EXAMPLE 43

Synthesis of 3-[[[[3-[(aminoiminomethyl)amino]phenyl]carbonyl]amino]methyl]-β-(1-methylethyl)benzenepropanoic acid, trifluoroacetate salt

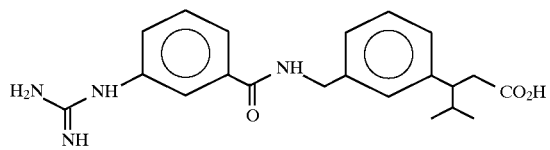

Step A

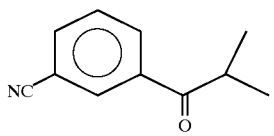

A solution of 3-acetylbenzonitrile (1.0 g, 6.9 mmol) in distilled THF (15 mL) was cooled to 0° C. A 1M solution of LiHMDS in THF (7.6 mL) was added slowly under argon. The resulting brown/red solution was allowed to warm to room temperature over 30 minutes. This solution was then added to a flask containing iodomethane (15 mL, 241 mmol) at room temperature The reaction was monitored by TLC (20% EtOAc/hexane). At the end of 1 hour, the TLC showed mostly the ethyl product and a minor amount of both the starting benzonitrile and the desired isopropyl product. The reaction was cooled to −30° C. (bath) and 1.1 equivalents of 1M LiHMDS were added. The reaction was allowed to warm slowly to 10° C. Within 5 minutes, the TLC showed the isopropyl product to be the predominant product. After stirring for 40 minutes, the reaction was quenched with water (50 mL) and extracted with EtOAc (2×50 mL). The organic layer was collected, dried over $MgSO_4$, and dried under a stream of $N_2$. The resulting orange residue was diluted with $CH_2Cl_2$ and the undissolved white solid filtered off. The filtrate was collected and concentrated in vacuo to give an orange oil (1.229 g). The oil was purified by column chromatography [50 g silica gel, 20% EtOAc/hexane (500 mL)] to give the desired product as a yellow oil (0.45 g). The impure fractions from the chromatography were combined and repurified by plate TLC (10% EtOAc/hexane) to give the product as a yellow oil (0.37 g). The pure samples from the column and plate chromatographies were combined to give the clean product (0.82 g, 69% yield). NMR was consistent with the proposed structure.

Step B

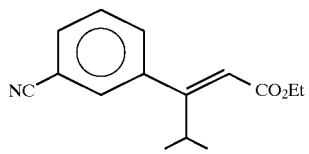

A solution of potassium tert-butoxide (0.37 g, 3.0 mmol) in distilled THF (20 mL) was cooled to 0° C. and ethyl dimethylphosphonoacetate (0.49 mL, 3.0 mmol) was added slowly under argon. The solution eventually became a white slurry. The reaction was stirred at 0° C. for 30 minutes before adding a solution of the compound of Step A (0.510 g, 2.9 mmol) in THF (3 mL). The reaction was heated to 50° C. (bath) for 7.5 hours, then stirred at room temperature over 15 hours. The reaction was quenched with water and extracted with EtOAc (2X). The organic layers were collected and dried over $MgSO_4$. Concentration in vacuo gave the crude product as a yellow oil (0.594 g). The crude product was combined with crude products from two other runs and purified by column chromatography to give two major fractions containing the desired compound as a yellow oil (0.256 g) contaminated with starting material (0.85 g). NMR was consistent with the proposed structure.

Step C

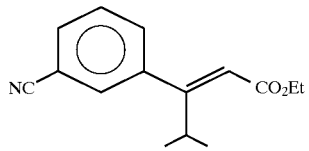

The mixture from Step B (0.85 g, 1.2 mmol) was dissolved in absolute ethanol (10 mL) and $NaBH_4$ (0.053 g, 1.4 mmol) was added at 0° C. under argon. The reaction was allowed to warm to room temperature and stirred for 18 hours. The reaction was quenched with $H_2O$ (30 mL) and extracted with EtOAc (2X). The organic layers were collected, dried over MgSO₄, and concentrated in vacuo to give a yellow oil (1.15 g). The crude product was purified by column chromatography [100 g silica gel, 10% EtOAc/hexane (500 mL)] to afford the desired compound as an impure mixture (0.47 g). NMR was consistent with the proposed structure.

Step D

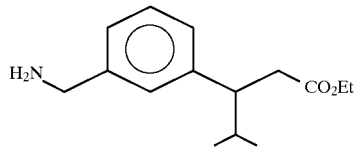

The mixture from Step C (0.521 g, 2.0 mmol) was hydrogenated under conditions similar to those described in Example AK to give a light tan oil (0.333 g). NMR was consistent with the proposed structure.

Step E

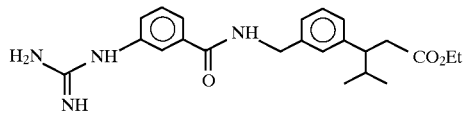

The product of Step D (0.28 g, 1.1 mmol) was coupled with the compound of Example AI using a method similar to that described in Example 34. The crude material was purified by HPLC-Method 1 to give the desired product as a colorless oil (0.070 g). NMR was consistent with the proposed structure.

Step F

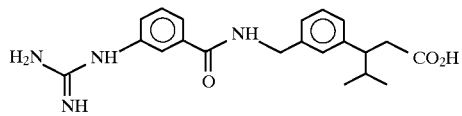

The product of Step E (0.057, 0.14 mmol) was hydrolyzed under conditions similar to those described in Example 26. The residue was purified by HPLC-Method 1 to give a colorless oil (0.045 g).

Analysis Calculated for C21H26N4O3.1.5 TFA+0.7 H₂O: C, 50.92; H, 5.15; N, 9.90. Found: C, 50.82; H, 4.99; H, 10.23. MH+=383.

EXAMPLE 44

3-[2-[[[3-[(aminoiminomethyl)amino]phenyl]carbonyl]amino]ethyl]benzeneacetic acid, monohydrate trifluoroacetate salt

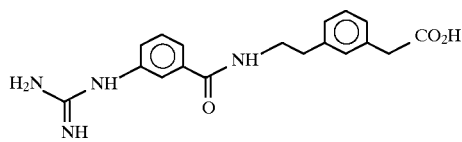

Step A

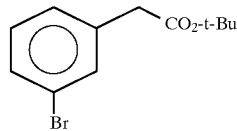

To a solution of 3-bromophenylacetic acid (2.980 g, 13.9 mmol) and condensed isobutylene (15 mL) in CH₂Cl₂ was added a catalytic amount of H₂SO₄. The mixture was sealed in a Parr Shaker and allowed to shake at room temperature for 18 hours. The bilayered reaction mixture was quenched with saturated NaHCO₃ (20 mL) and extracted with CH₂Cl₂ (2×30 mL). The organic layers were combined, washed with brine, dried over MgSO₄, and concentrated in vacuo to give a pale yellow oil (2.78 g, 74% yield)). NMR was consistent with the proposed structure.

Step B

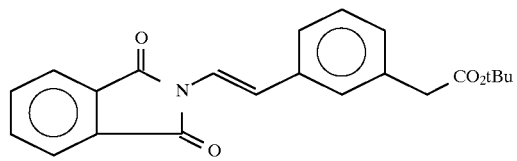

To a solution of the product of Step A (2.032 g, 7.4 mmol) in CH₃CN (4 mL) was added diisopropylamine (2 mL, 14.8 mmol), N-vinylphthalamide (1.285 g, 7.4 mmol), palladium acetate (0.059 g, 0.22 mmol), and tri-o-tolylphosphine (0.226 g, 0.7 mmol). The resulting yellow solution was heated to reflux for 18.5 hours. The reaction was allowed to cool to room temperature, at which point the reaction mixture solidified into a yellow/brown mass. The solid was dissolved in CH₂Cl₂ (50 mL) and the undissolved grey solid filtered off. The filtrate was treated with activated charcoal and filtered through celite. Concentration of the filtrate gave a yellow/brown solid. The material was recrystallized from CH₃CN₂ (5 mL)/MeOH (50 mL). A yellow needle-like solid was collected (1.435 g, 41% yield). NMR was consistent with the proposed structure.

Analysis Calculated for C₂₂H₂₁NO₄.0.4 H₂O: C, 71.30; H, 5.93; N, 3.78. Found: C, 71.08; H, 5.63; H, 3.46.

Step C

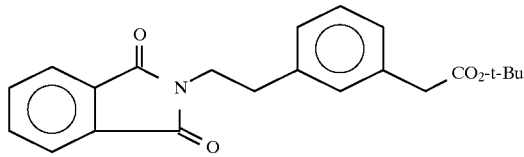

The compound of Step B (1.04 g, 2.9 mmol) was hydrogenated (10% Pd/C, EtOH+THF, 60 psi, room temperature, 10 hours). The reaction was concentrated in vacuo to give a white solid (1.21 g). The solid was purified by column chromatography [50 g silica gel, 20% EtOAc/hexane (500 mL)] to give the desired product as a white solid (0.54 g, 52% yield). NMR was consistent with the proposed structure.

Step D

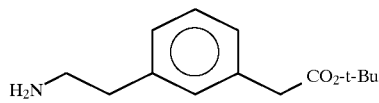

A mixture of the compound of Step C (0.54 g, 1.5 mmol) and hydrazine hydrate (0.33 g, 10.4 mmol) in absolute EtOH (6 mL) was heated to 75°–80° C. (bath). The solution solidified into a white mass after 20 minutes 10 of heating. The reaction was stirred at 80° C. for 2 hours. The reaction was allowed to cool to room temperature and then slurried with EtOH. A white solid was collected by vacuum filtration and then slurried with $CH_2Cl_2$ (2X). The undissolved solid was filtered 15 and the filtrate concentrated in vacuo to give a white sticky solid. Column chromatography [50 g silica gel, 84:15:1 $CHCL_3/EtOH/NH_4OH$ (700 mL)] gave the desired product as a pale yellow oil (0.25 g, 7% yield). NMR was consistent with the proposed structure.

Step E

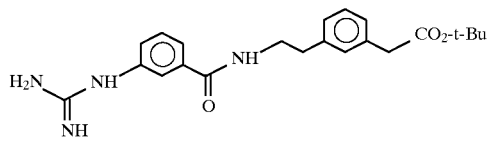

The compound of Step D (0.25 g, 1.1 mmol) was coupled with the compound of Example AI following the 30 procedures described in Example 34. The crude reaction mixture was purified by HPLC-Method 1 to give a sticky white/yellow solid (0.289 g). NMR was consistent with the proposed structure.

M+=396.

Step F

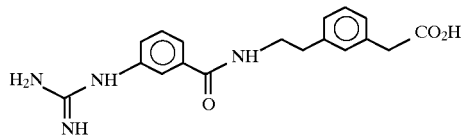

The compound of Step E (0.289 g) was hydrolyzed under conditions similar to those described in Example 40. The crude material was purified by HPLC-Method 1 to give a colorless oil (0.144 g).

Analysis Calculated for $C_{18}H_{20}N_4O_1 \cdot 1.2$ TFA+1.0 $H_2O$: C, 49.48; H, 4.72; N, 11.31. Found: C, 49.32; H, 4.47; N, 11.68. MH+=341.

EXAMPLE AO

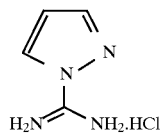

The above compound was prepared according to (Bernatowicz, JOC, Vol. 57, No. 8, (1992), p. 2497–2502. NMR was consistent with the proposed structure.

EXAMPLE 45

Synthesis of N-acetyl-3-[[[3-[(aminoiminomethyl)amino]phenyl]carbonyl]amino]methyl)phenylalanine, bis(trifluoroacetate) salt

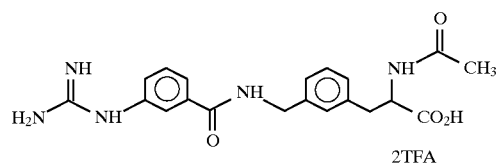

Step A

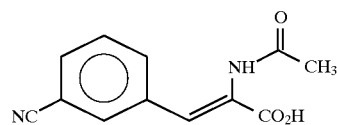

A mixture of N-acetylglycine (0.608 g, 5.1 mmol), sodium acetate (0.318 g, 3.8 mniol), 3-cyanobenzaldehyde (1.005 g, 7.6 mmol), and acetic anhydride (1.2 mL, 12.9 mmol) was heated to 88°–90° C. (bath) under argon for 7 hours. The reaction was allowed to cool to room temperature and stored in the refrigerator over the weekend. The resulting yellow solid was slurried in an ice bath and collected by vacuum filtration. The solid was dissolved in an acetone (36 mL)/water (14 mL) mixture and heated to reflux for 6–7 hours. The reaction was allowed to cool to room temperature and the acetone removed in vacuo. Additional water (40 mL) was added to the residue and the reaction mixture heated to reflux for 1 hour. The hot solution was filtered and the filter paper washed with hot water. The filtrate was collected and allowed to cool slowly to room temperature. Yellow crystals precipitated out of solution and the mixture was cooled for 5 hours. The crystals were collected by vacuum filtration, washed with cold water, and then rinsed with hexane to remove excess water. The desired product was collected as a yellow solid (0.427 g, 49% yield). NMR was consistent with the proposed structure.

Step B

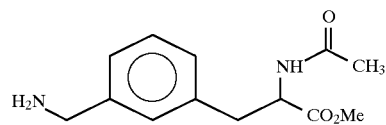

The product from Step A (0.201 g, 0.87 mmol) was hydrogenated at room temperature with Raney Nickel in $MeOH/NH_4OH$ over 16 hours at 60 psi. The catalyst was filtered and the filtrate concentrated in vacuo to give a green-tinted solid. 1M HCl (10 mL) was added slowly until the solid dissolved. The solution was concentrated in vacuo to give the desired product as a yellow oil (0.314 g, quantitative yield). NMR was consistent with the proposed structure.

Step C

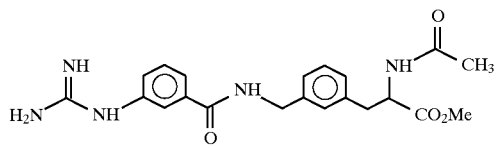

The product of Step B (0.307 g, 1.1 mmol) was coupled with the compound of Example AI under conditions similar to those described in Example 34. The crude material was purified by HPLC-Method 1 to give the methyl ester of the desired product as a pale yellow oil (0.231 g). NMR was consistent with the proposed structure.

Step D

The compound of Step C (0.125 g, 0.30 mmol) was hydrolyzed with LiOH according to the procedures described in Example 26. The residue was purified by HPLC-Method 1 (2X) to give the desired product as a colorless oil (0.052 g).

Analysis calculated for $C_{20}H_{23}N_5O_4 \cdot 2.0$ TFA+0.6 $H_2O$: C, 45.30; H, 4.15; N, 11.01. Found: C, 45.47; H, 4.19; N, 10.73. MH+=398.

EXAMPLE AP

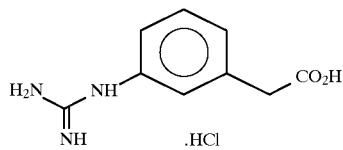

A solution of 3-aminophenylacetic acid (2.712 g, 17.9 mmol), the compound of Example AO (3.023 g, 20.6 mmol), and Hunig's base (3.6 mL, 20.6 mmol) in dioxane (30 mL)/water (15 mL) was refluxed for 16 hours under argon. Upon heating, a white precipitate formed. The reaction was cooled to room temperature and the white solid filtered. The solid was washed with 1:1 dioxane/water (3×5 mL). The solid was suspended in 15 mL of water and acidified with concentrated HCl until the solid dissolved. The solution was concentrated in vacuo and the resulting yellow residue slurried with ether. The yellow solid was collected by vacuum filtration (3.025 g, 74% yield). NMR was consistent with the proposed structure.

EXAMPLE 46

Synthesis of 3-[[[3-[(aminoiminomethyl)amino]phenyl]acetyl]amino]benzenepropanoic acid, trifluoroacetate salt

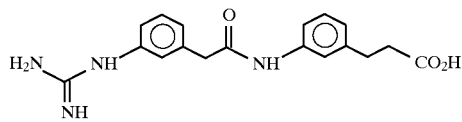

The compound of Example AX (0.3 g, 1.8 mmol) was coupled with the compound of Example AP under similar reaction conditions as described in Example 34. The crude mixture was purified by HPLC-Method 1 (2X) to give the desired product as a sticky light yellow oil (0.057 g).

Analysis Calculated for $C_{18}H_{20}N_4O_3 \cdot 1.9$ TFA: C, 47.01; H, 3.96; N, 10.06. Found: C, 47.21; H, 4.14; N, 9.86. MH+=341.

EXAMPLE AQ

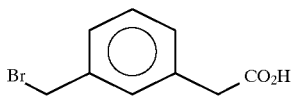

To a stirred solution of m-tolylacetic acid (3 g, 20 mmol) in carbon tetrachloride (60 mL) was added N-bromosuccinamide (3.6 g, 20 mmol). The mixture was refluxed for 3 hours then cooled to room temperature and filtered. The filtrate was concentrated under reduced pressure to yield 3.1 g of the desired compound.

EXAMPLE AR

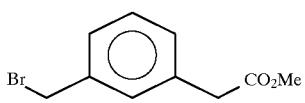

The compound of Example AQ (3.1 g, 13.5 mmol) was dissolved in methanol (150 mL) at 0° C. and a stream of hydrogen chloride gas was bubbled into the solution for 10 minutes. The mixture was then stirred for 2 hours at 0° C. The solvent was removed under reduced pressure and the residue was chromatographed on silica gel using EtOAc/Hexane (1:8) as eluant to give 1.3 g of the pure desired compound.

EXAMPLE AS

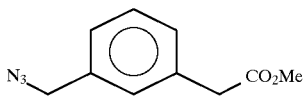

To a stirred solution of the compound of Example AR (1.3 g, 5.5 mmol) in dimethyl formamide (15 mL) was added sodium azide (377 mg, 5.8 mmol), and the mixture was stirred for 18 hours. The reaction mixture was poured into water and extracted with ethyl acetate. The combined organic phases were washed with water and brine, dried over $MgSO_4$ and evaporated. The residue was chromatographed on silica gel using EtOAc/Hexane (1:8) as eluant to give 0.8 g of the pure desired compound as a colorless oil.

EXAMPLE AT

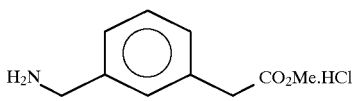

The compound of Example AS (749 mg, 3.65 mmol) was dissolved in EtOH (30 mL) and transferred to a Parr Shaker with 4% Pd/C (200 mg). The reaction was shaken for 24 hours at room temperature under 5 psi pressure of $H_2$. The reaction mixture was filtered and concentrated and the residue was dissolved in 4N HCl dioxane solution (4 mL). The solvent was removed and the residue was recrystallized from ether to give 0.5 g of the pure desired compound as white solid.

EXAMPLE 47

Synthesis of methyl 3-[[[[3-[(aminoiminomethyl)amino]phenyl]carbonyl]amino]methyl]benzeneacetate, trifluoroacetate salt

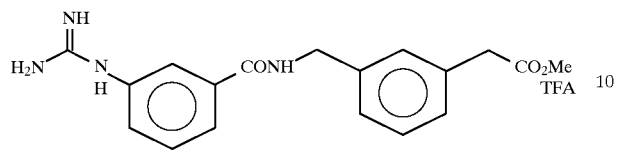

The title compound was prepared in the same manner as described in Example 34, replacing the compound of Example AC with the compound of Example AT.

Analysis Calculated for $C_{18}H_{20}N_4O_3 \cdot 1$ TFA $\cdot 0.8$ $H_2O$: C, 51.24; H, 4.86; N, 11.95. Found: C, 51.32; H, 4.66; N, 11.91.

EXAMPLE 48

Synthesis of ethyl 3-[[[3-(aminoiminomethyl)phenyl]carbonyl]amino]benzeneacetate, trifluoroacetate salt monohydrate

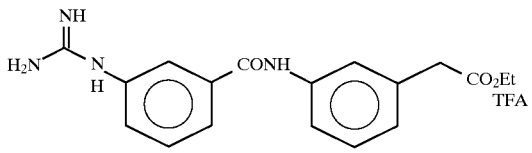

The above compound was prepared in the same manner as described in Example 34, replacing the compound of Example AC with the compound of Example Z.

Analysis Calculated for $C_{18}H_{20}N_4O_3 \cdot 1$ TFA $\cdot 1$ $H_2O$: C, 50.85; H, 4.91; N, 11.86. Found: C, 50.69; H, 4.54; N, 11.81.

EXAMPLE 49

Synthesis of 3-[[[[3-[(aminoiminomethyl)amino]phenyl]carbonyl]amino]methyl]benzeneacetic acid, trifluoroacetate salt

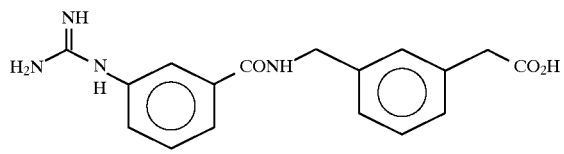

The compound of Example 47 was hydrolyzed in the same manner as described in Example 26.

Analysis Calculated for $C_{17}H_{18}N_4O_3 \cdot 1.3$ TFA $\cdot 0.4$ $H_2O$: C, 48.86; H, 4.20; N, 11.63. Found: C, 48.95; H, 3.90; N, 11.49.

EXAMPLE 50

Synthesis of 3-[[[3-[(aminoiminomethyl)amino]phenyl]carbonyl]amino]benzeneacetic acid, trifluoroacetate salt

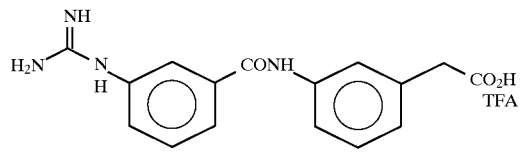

The compound of Example 48 was hydrolyzed in the same manner as described in Example 26.

Analysis Calculated for $C_{16}H_{16}N_4O_3 \cdot 1$ TFA $\cdot 0.5$ $H_2O$: C, 49.66; H, 4.17; N, 12.87. Found: C, 49.34; H, 4.03; N, 13.50.

EXAMPLE 51

Synthesis of 3-[[[[3-[(aminoiminomethyl)amino]phenyl]amino]carbonyl]amino]benzenepropanoic acid, trifluoroacetate salt

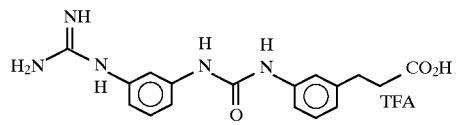

Step A

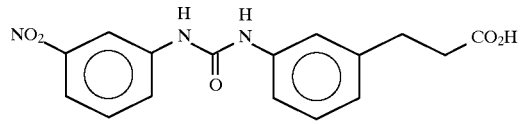

To a stirred solution of 3-nitrophenylisocyanate (0.5 g, 3.1 mmol, Aldrich) in methylene chloride (20 mL) was added 3-aminohydrocinnamic acid (0.45 g, 2.7 mmol, Example AX) in small portions over 5 minutes. The mixture was stirred 18 hours at room temperature. The mixture was then poured into 10% aqueous sodium hydroxide (50 mL) and washed with ethyl acetate (2×25 mL). The basic solution was acidified with 10% HCl and the resulting precipitate was filtered and dried. This produced 0.63 g (70%) of the title compound.

HRMS (M+) for $C_{16}H_{15}N_3O_5$ calculated: 329.1012, found: 329.1003.

Step B

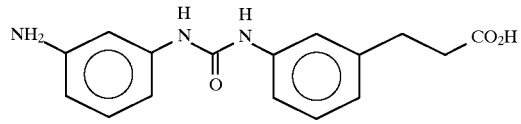

A stirred solution of the product of Example 51A (0.3 g, 0.91 mmol) in ethyl alcohol (25 mL) and THF (50 mL) was hydrogenated over 4% palladium on carbon under an atmosphere of hydrogen at 5 psi. The solvent was removed at reduced pressure to produce 0.29 g (100%) of the title compound.

APCI MS (M+) for $C_{16}H_{17}N_3O_3$ Calculated: 299, Found: 299.

Step C

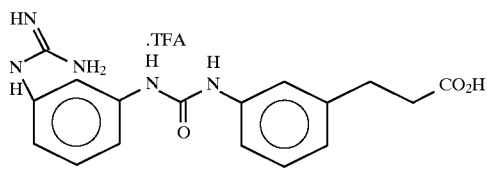

A stirred solution of the product of Example 51B (0.29 g, 0.97 mmol), diisopropylethylamine (0.27 mL) and pyrazole-1-carboxamidine hydrochloride (219 mg, 1.5 mmol) in dioxane (9 mL) and water (1.5 mL) was heated at reflux for 3 hours. After cooling to room temperature, the solvents were removed at reduced pressure and the residue was chromatographed (reverse phase HPLC, gradient elution with water/acetonitrile/trifluoroacetic acid). This produced 0.02 g (4.5%) of the title compound.

ESI MS (free base MH+) for $C_{17}H_{20}N_5O_3$ Calculated: 342, Found: 342.

EXAMPLE 52

Synthesis of [3-[[[[3-[(aminoiminomethyl)amino]phenyl]amino]carbonyl]amino]phenoxy]acetic acid, trifluoroacetate salt

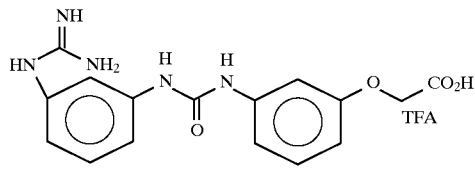

Step A

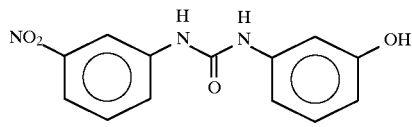

3-Aminophenol (1.0 g, 9.2 mmol, Aldrich) was subjected to the reaction conditions described for the preparation of Example 51A. This produced 0.5 g (20%) of the title compound.

HRMS (M+) for $C_{13}H_{11}N_3O_4$ Calculated: 273.0749, Found: 273.0732.

Step B

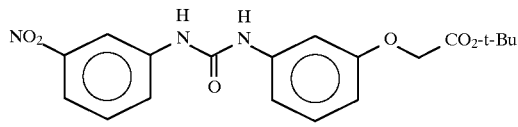

The product of Step A (0.5 g, 1.8 mmol) in THF (20 mL) was cooled (−30° C.) and treated with sodium hydride (50% dispersion in mineral oil, 0.1 g, 2 mmol) in small portions over 15 minutes. The solution was then warmed (0° C.) and stirred 30 minutes and then cooled to −30° C. To this solution was added neat t-butyl bromoacetate (0.49 g, 2.5 mmol, Aldrich) and the mixture was stirred 1 hour at −30° C. and then warmed to room temperature and stirred 1 hour. The volatile components were removed at reduced pressure on a rotary evaporator and the residue was taken up in ether (50 mL). The ether was washed with water (25 mL), 10% NaOH (25 mL) and brine (25 mL). This produced 0.6 g (86%) of the above compound.

HRMS (M+) for $C_{19}H_{21}N_3O_6$ Calculated: 387.1430, Found: 387.1427.

Step C

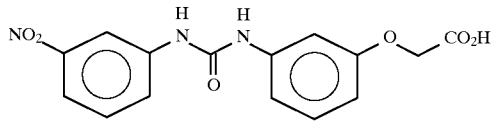

The product of Step B (0.6 g, 1.6 mmol) in methylene chloride (25 mL) was cooled (0° C.) and treated with trifluoroacetic acid (5 mL). The solution was warmed to room temperature and stirred for 3 hours. The volatile components were removed at reduced pressure on a rotary evaporator. The residue was chromatographed on silica gel eluting with 1% acetic acid/ethyl acetate. This produced 0.39 g (76%) of the above compound.

HRMS (M+) for $C_{15}H_{13}N_3O_6$ Calculated: 331.0804, Found: 331.0790.

Step D

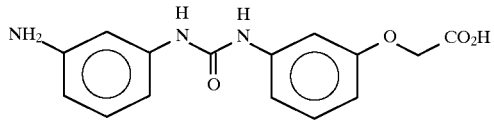

The product of Example 52C (0.3 g, 0.91 mmol) was subjected to the reaction conditions described for the preparation of Example 51B. This produced 0.08 g (90%) of the title compound.

ESI MS (MH+) for $C_{16}H_{17}N_3O_3$ Calculated: 302, Found: 302.

Step E

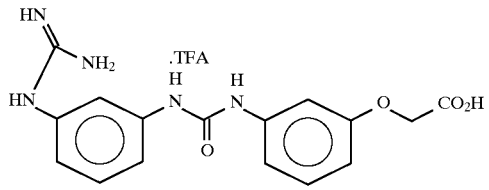

The product of Example 52D (0.08 g, 0.27 mmol) was subjected to the reaction conditions described for the preparation of Example 51C. This produced 0.04 g (32%) of the title compound.

ESI MS (free base MH+) for $C_{16}H_{18}N_5O_4$ Calculated: 344, Found: 344.

EXAMPLE 53

Synthesis of 3-[[[[3-[(aminoiminomethyl)amino]phenyl]amino]carbonyl]amino]methyl] benzenepropanoic acid, trifluoroacetate salt

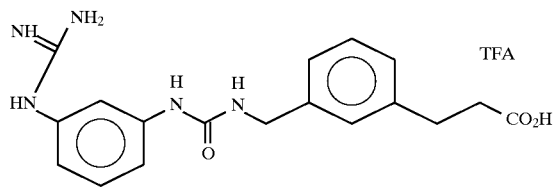

Step A

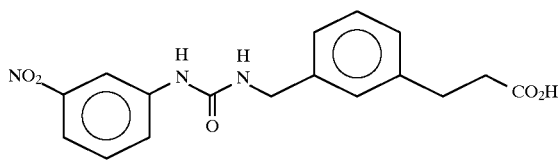

The product from Example AB (0.09 g, 0.4 mmol) was subjected to the reaction conditions described for the preparation of Example 51A. The crude product was chromatographed on silica gel gradient eluting with ethyl acetate (containing 1% acetic acid) and produced 0.06 g (42%) of the above compound.

HRMS (M+) for $C_{17}H_{17}N_3O_5$ Calculated: 343.1168, Found: 343.1158.

Step B

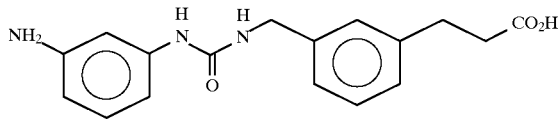

The product from Example 53A (0.06 g, 0.17 mmol) was subjected to the reaction conditions described for the preparation of Example 51B. This produced 0.06 g (100%) of the above compound.

APCI MS (MH+) for $C_{17}H_{20}N_3O_3$ Calculated: 314.15. Found: 314.12.

Step C

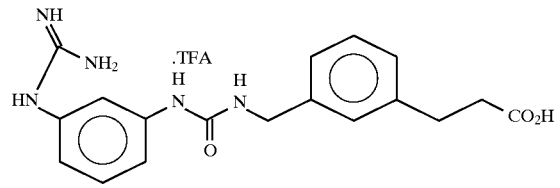

The product from Example 53B (0.06 g, 0.19 mmol) was subjected to the reaction conditions described for the preparation of Example 51C. This produced 0.05 g (56%) of the title compound.

APCI MS (free base MH+) for $C_{18}H_{22}N_5O_3$ Calculated: 356, Found: 356.

EXAMPLE 54

β-[3-[[[[3-(aminoiminomethyl)amino]phenyl]carbonyl]amino]methyl]phenyl]-3,5-dichlorobenzenepropanoic acid

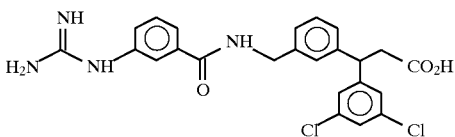

Step A

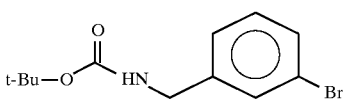

A solution of 3-bromobenzylamine hydrochloride (2.93 g, 13 mmol), di-tert-butyldicarbonate (2.874 g, 13 mmol), and triethylamine (3.7 mL, 26 mmol) in 80:20 dioxane/water (40 mL) was stirred for 23 hours. The reaction was concentrated in vacuo and the residue dissolved in EtOAc. The solution was washed with water and brine. Concentration in vacuo gave a light yellow solid (4.59 g). NMR was consistent with proposed structure.

Step B

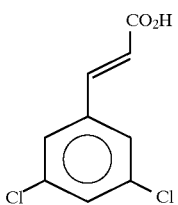

A mixture of 3,5-dichlorobenzaldehyde (2.00 g, 11.4 mmol), malonic acid (1.451 g, 12.6 mmol), and pyridine (0.16 mL, 1.9 mmol) in absolute ethanol (20 mL) was heated to 105° C. (bath) under argon. After 24 hours, the reaction was allowed to cool to room temperature and then concentrated in vacuo to give a white solid slurry. The solid was redissolved in $Et_2O$ (50 mL) and washed with 1M HCl followed by water. The organic layer was collected, dried over $MgSO_4$, and concentrated in vacuo to give a white sticky solid. The solid was purified by slurrying with hexane. The undissolved white solid was collected by vacuum filtration (0.65 g). NMR was consistent with proposed structure.

Step C

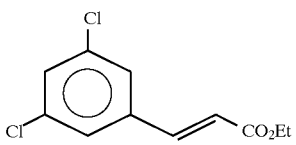

A solution of the compound of Step B (0.65 g, 3.0 mmol) in absolute EtOH (60 mL) was cooled to 0° C. and HCl (g) was bubbled into it for 15 minutes. The solution was allowed to stir for 5 hours. An aliquot was removed and concentrated in vacuo. H NMR showed the reaction to be complete. The reaction was concentrated in vacuo to give a white solid (0.74 g). NMR was consistent with proposed structure.

Step D

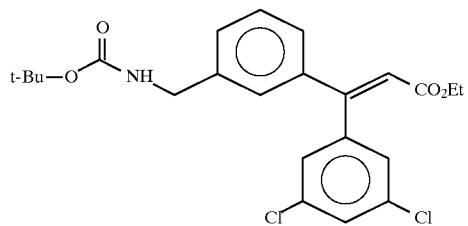

A solution of the compound of Step A (0.44 g, 1.5 mmol) and the compound of Step C (0.36 g, 1.5 mmol) in diisopropylamine (4 mL) was purged for 5 minutes with argon before adding tri-o-tolylphosphine (0.024 g, 0.05 mmol) and palladium acetate (0.010 g, 0.03 mmol). The resulting solution was purged with argon for 2 minutes and sealed. The reaction vessel was heated to 135°–140° C. (bath) for 5 hours. The reaction was diluted with water (50 mL) and extracted with EtOAc (50 mL). The organic layer was collected and washed a second time with water. The organic layer was dried over MgSO$_4$ and filtered through celite. Concentration in vacuo gave the crude product as a yellow solid (0.69 g). The solid was purified by column chromatography [100 g silica gel, 20% EtOAc/hexane (500 mL)] to give a white solid (0.31 g). NMR was consistent with proposed structure.

Step E

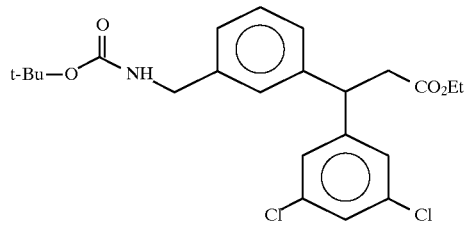

The compound of Step D was dissolved in EtOH and hydrogenated with 5% Pt/C at room temperature under 5 psi for 16 hours. The catalyst was filtered off and the filtrate concentrated in vacuo to give an oil (0.354 g). NMR was consistent with proposed structure.

Step F

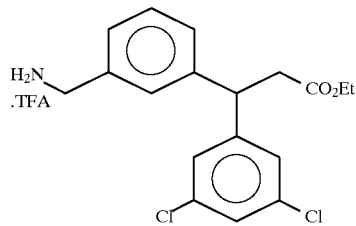

To a solution of the compound of Step E (0.354 g, 0.7 mmol) in CH$_2$Cl$_2$ (5 mL) was added TFA (1 mL) at 0° C. The ice bath was removed after the addition and the reaction was stirred at room temperature for 1.5 hours. The reaction was concentrated in vacuo to give a green/brown oil (0.493 g). NMR was consistent with proposed structure.

Step G

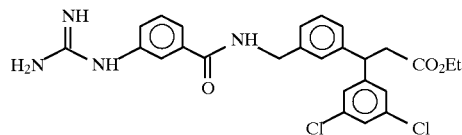

A solution of AI (0.153 g, 0.7 mmol) and 1-methyl piperidine (0.09 mL, 0.7 mmol) in DMF (3 mL) was cooled to 0° C. and isobutyl chloroformate (0.09 mL, 0.7 mmol) was added under argon. The reaction was allowed to stir for 5 minutes before adding a solution of the compound of Step F (0.7 mmol) and 1-methyl piperidine (0.09 mL, 0.7 mmol) in DMF (2 mL). The flask containing the compound of Step F was rinsed with DMF (1 mL) and the rinse was added to the reaction. The reaction was allowed to warm slowly to room temperature over 16 hours. The reaction was concentrated in vacuo and the residue purified by HPLC to give the desired product as a yellow oil (0.101 g). NMR was consistent with proposed structure.

Step H

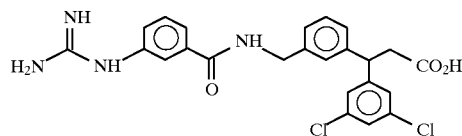

The compound of Step G (0.101 g, 0.25 mmol) was dissolved in MeOH (3 mL) and 1M LiOH (0.5 mL) was added at room temperature. The reaction was stirred for 23 hours. The reaction was concentrated in vacuo and the residue diluted with water (1 mL). The solution was acidified dropwise to pH 1 with TFA. The reaction was reconcentrated and the residue purified by HPLC to give a white solid (0.053 g).

Analysis Calculated for C$_{24}$H$_{22}$N$_4$O$_3$Cl$_2$.1.0 TFA+1.0 H$_2$O: C, 50.58; H, 4.08; N, 9.07. Found: C, 50.41; H, 3.86; N, 9.29. M+=485.

EXAMPLE 55

3-[[[[3-[[(cyanoimino)(methylamino)methyl]amino]phenyl]carbonyl]amino]methyl]-β-phenylbenzenepropanoic acid

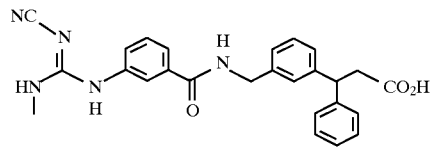

Step A

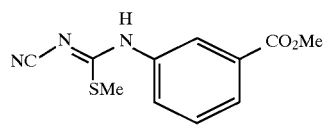

A stirred mixture of 3-amino methyl benzoate (6.04 g, 40 mmol) and dimethyl N-cyanodithioiminocarbonate (11.96 g, 80 mmol) in pyridine (70 mL) was heated at reflux under a nitrogen atmosphere for 2.5 hours. The reaction mixture was cooled to room temperature. On standing overnight at room temperature the above compound crystallized from the reaction mixture affording 6.2 g (two crops). The above compound was used without further purification in the proceeding examples. NMR was consistent with the proposed structure.

Step B

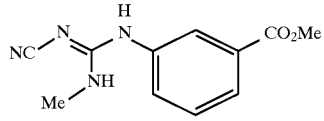

A stirred mixture of the compound produced in Step A (0.56 g, 2.2 mmol) and methylamine (40%, 1.21 g, 15.4 mmol) in ethanol (20 mL) was heated in a sealed pressure vessel to 90° C. for 3.5 hours. The reaction mixture was cooled to room temperature. After standing overnight at room temperature a white solid was obtained, which was isolated by filtration and washed with methanol. This afforded the above compound as a white solid (510 mg). NMR was consistent with the proposed structure.

Step C

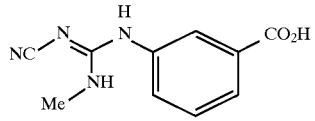

To a stirred solution of the product from Step B (0.51 g, 2.2 mmol) in THF (3 mL) and methanol (3 mL), 1N NaOH (3 mL) was added. The reaction mixture was stirred at room temperature for 2 hours and concentrated in vacuo to afford a white solid. The residue was acidified by suspension in water followed by addition of 1N HCl. The resultant solid was filtered, washed with diethyl ether, and dried to afford the above compound (259 mg). NMR was consistent with the proposed structure.

Step D

The compound of Step C (220 mg, 0.79 mmol) was coupled with the compound of Step D in Example 37 according to similar procedure described in Example 34 and purified by reverse phase HPLC (water/acetonitrile) to give a light yellow oil (194 mg). NMR was consistent with the proposed structure.

Step E

The compound of Step D (111 mg, 0.23 mmol) was hydrolyzed under the conditions described in Example 26 and purified by reverse phase HPLC (water/acetonitrile) to give the title compound as a white solid (100 mg). NMR was consistent with the proposed structure.

Analysis Calculated for $C_{20}H_{24}N_4O_3 \cdot 1.4$ TFA: C, 51.86; H, 4.85; N, 10.61. Found: C, 51.57; H, 4.99; N, 11.01.

EXAMPLE 56

3-[[[[3-[(aminoiminomethyl)amino]phenyl]carbonyl]amino]methyl]-βR-methylbenzenepropanoic acid, trifluoroacetate salt hydrate

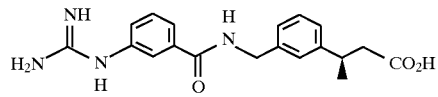

Step A

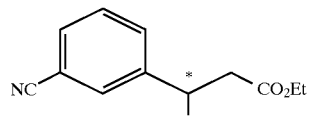

The product of Example AJ was hydrogenated (THF, 5% Pd/C, 5 psi, room temperature, 40 minutes) and the filtrate concentrated in vacuo. The two enantiomers were separated by chrial HPLC.

Step B

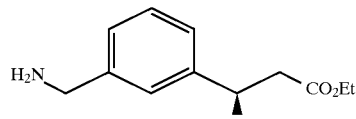

The R isomer from Step A was hydrogenated (EtOH, RaNi, 60 psi, room temperature, 1 hour) and the filtrate concentrated in vacuo.

Step C

The compound of Step B (223 mg, 1 mmol) was coupled with the compound of Example AI (217 mg, 1 mmol) according to a similar procedure as described in Example 34 and purified by reverse phase HPLC (water/acetonitrile) to give a brown oil (134 mg). NMR was consistent with the proposed structure.

Step D

The compound of Step C (134 mg, 0.35 mmol) was hydrolyzed under the conditions described in Example 26 and purified by reverse phase HPLC (water/acetonitrile) to give the title compound (130 mg). NMR was consistent with the proposed structure.

Analysis Calculated for $C_{19}H_{22}N_4O_3 \cdot 1.2$ TFA+1.5 $H_2O$: C, 49.60; H, 5.10; N, 10.81. Found: C, 49.39; H, 4.72; N, 10.45.

EXAMPLE 57

3-[[[[3-[(aminoiminomethyl)amino]phenyl]carbonyl]amino]methyl]-βS-methylbenzenepropanoic acid

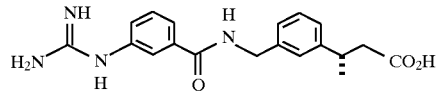

The title compound was prepared in the same manner as described in Example 56, replacing the R isomer with the S isomer. NMR was consistent with the proposed structure.

MH+=355.

EXAMPLE 58

(±) 3-[[[[3-[(aminoiminomethyl)amino]-4-chlorophenyl]carbonyl]amino]methyl]-β-ethylbenzenepropanoic acid, trifluoroacetate salt

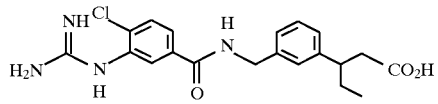

Step A

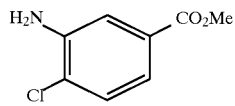

To a stirred suspension of 3-amino-4-chlorobenzoic acid (25.0 g, 157 mmol) in MeOH (300 mL) at 0° C., hydrogen chloride gas was added until the methanolic solution was saturated. The reaction mixture was stirred at 0°–5° C. for 30 minutes, allowed to attain room temperature, and then stirred for a further 4 days. The reaction mixture was concentrated in vacuo and the resulting white solid triturated with diethyl ether to afford the above compound as a white solid (26.2 g).

Step B

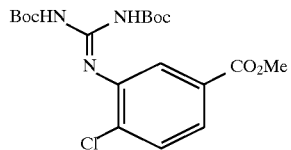

To a solution of N,N'-bis-tert-butoxycarbonyl thiourea (24.8 g, 90 mmol) and methyl-3-amino-4-chlorobenzoate (20 g, 90 mmol) in dimethylformamide (120 mL) and triethylamine (45 ml) at 0° C. mercury II chloride (30.1 g, 111 mmol) was added. The reaction mixture was stirred for 15 minutes at 0° C., allowed to attain room temperature, and then stirred for a further 2 hours. The reaction mixture was diluted with ethyl acetate (600 mL) and the resulting slurry filtered under reduced pressure. The filtrate was concentrated, to afford an oily gum which was purified by chromatography on silica gel (eluent:ethyl acetate/heptane 20:80) to afford the above compound as a white solid (8.6 g).

Step C

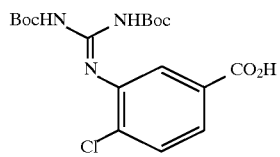

The product of Step B (2 g, 4.7 mmol) was dissolved in MeOH (3 mL) and 1M NaOH (14 mL) was added at room temperature. The reaction was stirred at room temperature for 2 hours. The reaction was concentrated in vacuo and the residue dissolved in water and washed with ether. The aqueous layer was acidified to pH=3 with 1N HCl. A white precipitate formed, was filtered and washed with water and ether and dried to give 1.2 g of a white solid. NMR was consistent with the proposed structure.

Step D

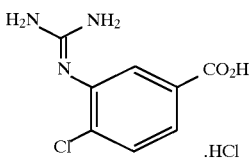

To a solution of the product of Step C (550 mg, 1.33 mmol) in $CH_2Cl_2$ (4 ml) was added TFA (1 mL) at 0° C. The ice bath was removed after the addition and the reaction was stirred at room temperature for 2 hours. The reaction was concentrated in vacuo to give a colorless oil. To this was added 4N HCl solution in dioxane (2 mL) and white precipitate formed. The solution was concentrated in vacuo to afford 280 mg of a white solid. NMR was consistent with the proposed structure.

Step E

The compound of Step D (245 mg, 0.98 mmol) was coupled with the compound of Step C in Example 41 (238 mg, 0.98 mmol) according to a similar procedure as described in Example 34 and purified by reverse phase HPLC (water/acetonitrile) to give a yellow oil (200 mg). NMR was consistent with the proposed structure.

Step F

The compound of Step E (197 mg, 0.4 mmol) was hydrolyzed under the conditions described in Example 26 and purified by reverse phase HPLC (water/acetonitrile) to give a white solid (146 mg). NMR was consistent with the proposed structure.

Analysis Calculated for $C_{20}H_{23}N_4O_3Cl.1.4$ TFA+0.8 $H_2O$: C, 47.47; H, 4.54; N, 9.71. Found: C, 47.38; H, 4.28 N, 9.67.

EXAMPLE 59

(±) 3-[[[[3-[(aminoiminomethyl)amino]-5-(trifluoromethyl)phenyl]carbonyl]amino]methyl]-β-ethylbenzenepropanoic acid, trifluoroacetate salt

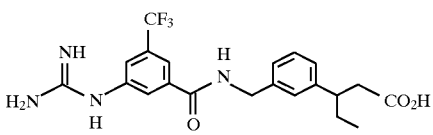

Step A

The compound of Example D (88 mg, 0.31 mmol) was coupled with the compound of Step C in Example 41 (73 mg, 0.31 mmol) according to a similar procedure as described in Example 34 and purified by reverse phase HPLC (water/acetonitrile) to give a colorless oil (48 mg). NMR was consistent with the proposed structure.

Step B

The compound of Step A (48 mg, 0.1 mmol) was hydrolyzed under the conditions described in Example 26 and purified by reverse phase HPLC (water/acetonitrile) to give a colorless oil (38 mg). NMR was consistent with the proposed structure.

Analysis Calculated for $C_{21}H_{23}N_4O_3F_3.1.4$ TFA+0.4 $H_2O$: C, 47.39; H, 4.21; N, 9.29. Found: C, 47.33; H, 3.97; N, 9.29.

EXAMPLE 60

(±) β-[3-[[[[3-[(aminoiminomethyl)amino]phenyl]carbonyl]amino]methyl]phenyl]-3,5-difluorobenzenepropanoic acid, trifluoroacetate salt

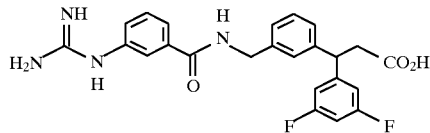

Step A

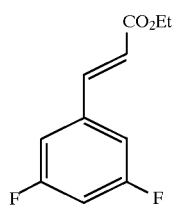

A solution of potassium tert-butoxide (0.9 g, 7.2 mmol) in THF (20 mL) was cooled to 0° C. and ethyl dimethyl phosphonoacetate (1.4 g, 7.2 mmol) was added slowly under argon. The reaction was stirred for 20 minutes. A solution of benzaldehyde in THF (5 mL) was added to the reaction dropwise. The ice bath was taken off immediately and the reaction was stirred at room temperature for 2 hours. The reaction was quenched with water and extracted with ethyl acetate (2X). The organic layers were combined and washed with brine, dried over MgSO$_4$ and concentrated in vacuo. The residue was purified by chromatography on silica gel (eluent:ethyl acetate/Hexane 20%) to afford the above compound as colorless oil (1.5 g). NMR was consistent with the proposed structure.

Step B

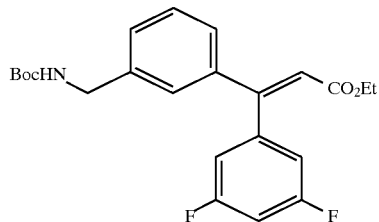

The above compound was prepared in the same manner described in Step D of Example 54, replacing the compound of Step C in Example 54 with the product of Step A. NMR was consistent with the proposed structure.

Step C

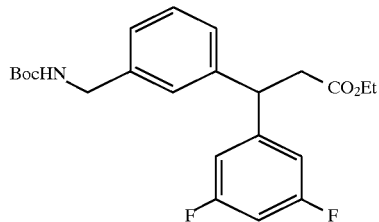

The product from Step B was reduced in the same manner described in Step C, Example 77.

Step D

The title compound was prepared in the same manner as described in Example 54 (Step F to Step H), replacing the compound of Step E in Example 54 with the product of Step C. NMR was consistent with the proposed structure.

Analysis Calculated for $C_{24}H_{22}N_4O_3F_2$.1.6 TFA+0.3 H$_2$O: C, 51.02; H, 3.81; N, 8.75. Found: C, 50.82; H, 3.54; N, 9.02.

EXAMPLE 61

(±) β-[3-[[[[3-[(aminoiminomethyl)amino]-5-(trifluoromethyl)phenyl]carbonyl]amino]methyl]phenyl]-3,5-difluorobenzenepropanoic acid, trifluoroacetate salt hydrate

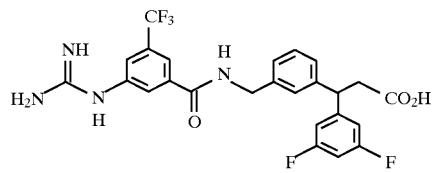

The product from Step C in Example 60 was deprotected as described in Step F, Example 54, and then coupled with the compound of Example D using a method similar to that described in Example 54 (Step G to Step H) to afford the title compound. NMR was consistent with the proposed structure.

Analysis Calculated for $C_{25}H_{21}N_4O_3F_5$.1.8 TFA.1.1 H$_2$O: C, 46.08; H, 3.38; N, 7.52. Found: C, 45.70; H, 3.12; N, 7.64.

EXAMPLE 62

(±) 3,5-difluoro-β-[3-[[[[3-[(1,4,5,6-tetrahydropyrimidin-2-yl)amino]phenyl]carbonyl]amino]methyl]phenyl]benzenepropanoic acid, trifluoroacetate salt monohydrate

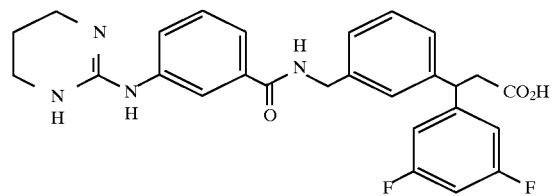

Step A

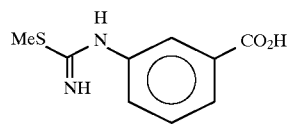

1-(3-Carboxyphenyl)-2-thiourea (5 g, 0.025 mole) (Trans World Chemicals) in THF (75 mL) and iodomethane (3.62 g, 0.025 mole) were stirred at reflux for 2 hours. The solvent was removed under vacuum and the residue was slurried in ether (3X), to yield, after drying under vacuum, N-(3-carboxyphenyl)-S-methylisothiouronium hydriodide (7.8 g) as a yellow solid.

Step B

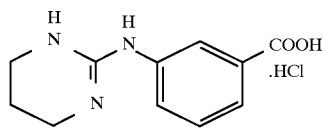

To the product of Step A (10.1 g, 0.03 mole) in DMF (15 mL) was added 1,3-diaminopropane (2.22 g, 0.03 mole), triethylamine (3.9 g, 0.03 mole), and DMAP (420 mg). The reaction mixture was heated at 140°–150° C. for 4.5 hours. After cooling to room temperature, $H_2O$ (30 mL) was added and, after stirring for 15 minutes, the precipitate was filtered and washed with $H_2O$. The precipitate was slurried in $H_2O$ and made acidic with concentrated HCl. A solution formed. After lyophilizing off the solvent, the residue was slurried 2X with isopropyl ether. After drying under vacuum 3-(2-amino-1,4,5,6-tetrahydropyrimidine)-benzoic acid hydrochloride was produced (4.0 g) as a white solid. MS and NMR were consistent with the desired structure.

Step C

The product from Step C in Example 60 was deprotected as described in Step F of Example 54 and then coupled with the product from Step B using a method similar to that described in Example 54 (Step G to Step H) to afford the title compound. NMR was consistent with the proposed structure.

Analysis Calculated for $C_{27}H_{26}N_4O_3F_2 \cdot 1.4$ TFA $\cdot 1.0$ $H_2O$: C, 53.41; H, 4.42; N, 8.36. Found: C, 43.12; H, 4.14; N, 8.25.

EXAMPLE 63

(±) -[3-[[[[3-[(aminoiminomethyl)amino]phenyl] carbonyl]amino]methyl]phenyl]-2-methoxybenzene propanoic acid, trifluoroacetate salt hydrate

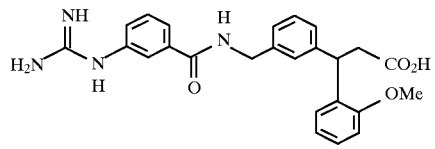

Step A

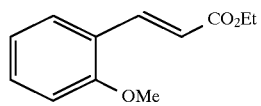

A solution of potassium tert-butoxide (1.06 g, 8.8 mmol) in THF (40 mL) was cooled to 0° C. and ethyl dimethyl phosphonoacetate (1.7 g, 8.8 mmol) was added slowly under argon. The reaction was stirred for 30 minutes. A solution of o-anisaldehyde (1.02 g, 7.3 mmol) in THF (3 mL) was added to the reaction dropwise. The ice bath was taken off immediately and the reaction was stirred at room temperature for 1.5 hours. The reaction was quenched with water and extracted with ethyl acetate (2X). The organic layers were combined and washed with brine, dried over $MgSO_4$ and concentrated in vacuo. The residue was purified by chromatography on silica gel (eluent:ethyl acetate/hexane 30%) to afford the above compound as colorless oil (1.58 g).

Step B

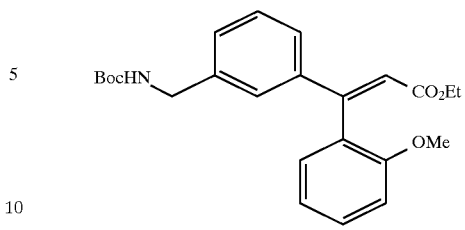

The above compound was prepared in the same manner described in Step D of Example 54, replacing the compound of Step C in Example 54 with the product of Step A. NMR was consistent with the proposed structure.

Step C

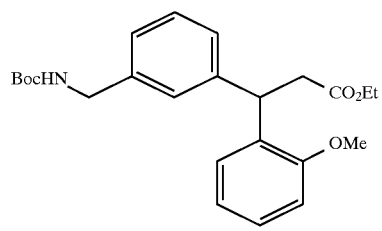

The product of Step B (0.72 g, 1.7 mmol) was dissolved in EtOH and hydrogenated with 5% Pd/C in a Parr Shaker (5 psi) at room temperature for 2 hours. The catalyst was filtered off and the filtrate concentrated in vacuo to give the desired product as a yellow oil (0.485 g). NMR was consistent with the proposed structure.

Step D

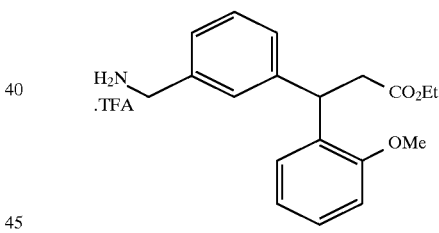

The product of Step C was deprotected in the same manner described in Step F of Example 54. NMR was consistent with the proposed structure.

Step E

The product of Step D (330 mg, 1.05 mmol) was coupled with the compound of Example AI (230 mg, 1.05 mmol) according to a similar procedure as described in Example 34 and purified by reverse phase HPLC (water/acetonitrile) to give a yellow solid (360 mg). NMR was consistent with the proposed structure.

Step F

The compound of Step E (360 mg, 0.76 mmol) was hydrolyzed under the conditions described in Example 26 and purified by reverse phase HPLC (water/acetonitrile) to give a colorless oil (300 mg). NMR was consistent with the proposed structure.

Analysis Calculated for $C_{25}H_{26}N_4O_4 \cdot 1.8$ TFA $+ 1.3$ $H_2O$: C, 50.88; H, 4.54; N, 8.30. Found: C, 50.54; H, 4.26; N, 8.51.

EXAMPLE 64

(±) 3[[[[3-[[amino(cyanoimino)methyl]amino]
phenyl]carbonyl]amino]methyl]-β-
methylbenzenepropanoic acid

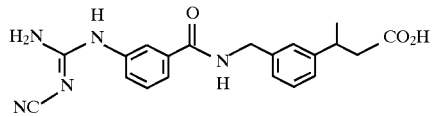

Step A

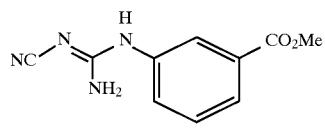

A stirred mixture of the compound from Step A in Example 55 (1 g) and ammonium hydroxide (2 mL) in ethanol (20 mL) was heated at 70° C. in a sealed tube for 3.5 hours. The reaction mixture was cooled to room temperature and reduced to half its volume. After standing overnight at room temperature a white solid was obtained, which was isolated by filtration and washed with methanol. This afforded the above compound as a white solid. NMR was consistent with the proposed structure.

Step B

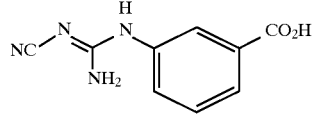

The product of Step A was hydrolysed in the same manner as described in Step C of Example 55. NMR was consistent with the proposed structure.

Step C

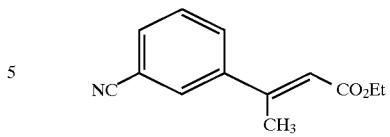

The above compound was prepared under the same conditions as described in Example AJ, replacing t-butyl P,P-dimethylphosphonoacetate with ethyl P,P-dimethylphosphonoacetate.

Step D

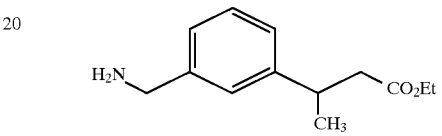

The product of Step C was hydrogenated under the same conditions as described in Example 37, Step D.

Step E

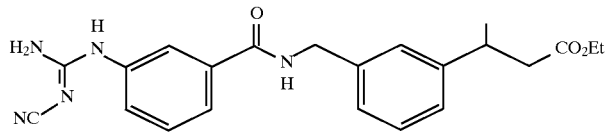

The compound of Step B was coupled with the compound of Step D according to similar procedure described in Example 34. NMR was consistent with the proposed structure.

Step F

The compound of Step E was hydrolyzed under the conditions described in Example 26. NMR was consistent with the proposed structure.

Analysis Calculated for $C_{20}H_{21}N_5O_3+0.5\ H_2O$: C, 61.84; H, 5.71; N, 18.03. Found: C, 61.84; H, 5.63; N, 17.70.

EXAMPLE 65

(±) 3[[[[3-[[amino[(aminocarbonyl)imino]methyl]
amino]phenyl]carbonyl]amino]methyl]-β-
methylbenzenepropanoic acid, trifluoroacetate salt

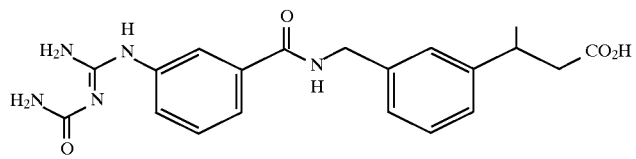

Step A

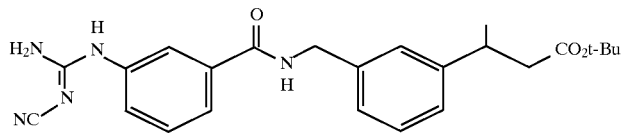

The product from Step B of Example 64 was coupled with the compound of Example AK according to a similar procedure as described in Example 34. NMR was consistent with the proposed structure.

Step B

A solution of the product from Step A (100 mg, 0.23 mmol) in a 1:1 CH$_2$Cl$_2$:TFA solution (1 mL) was kept at room temperature for 2 hours. The reaction solution was evaporated under a stream of N$_2$. The residue was purified by reverse phase HPLC (H$_2$O/TFA:MeCN) to give the title compound, 77 mg. $^1$H NMR and MS were consistent with the proposed structure.

EXAMPLE 67

(±) 3-[[[[3-[(4,5-dihydro-4-oxo-1H-imidazol-2-yl)amino]phenyl]carbonyl]amino]methyl]-β-methylbenzenepropanoic acid

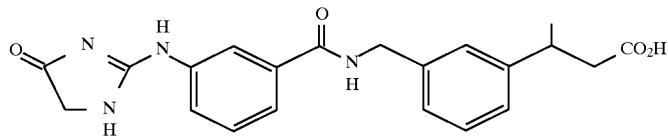

Step A

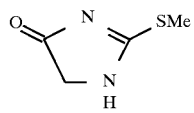

To a mixture of 2-thiohydantoin (5.5 g, 47.4 mmol) in absolute ethanol (60 mL) was added methyl iodide (3.5 mL, 56.6 mmol). The mixture was heated at reflux for 5 hours. The mixture was cooled to room temperature and concentrated in vacuo. $^1$H NMR was consistent with the proposed structure.

Step B

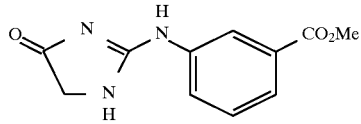

To a mixture of the product from Step A (1.0 g, 3.8 mmol) in absolute ethanol (20 mL) was added ethyl 3-aminobenzoate (2.5 g, 15.3 mmol). The mixture was stirred at room temperature for 16 hours. The mixture was concentrated in vacuo and the residue was purified by chromatography (85:14:1 CH$_2$Cl$_2$:MeOH:NH$_4$OH) to give the desired product, 414 mg. $^1$H NMR was consistent with the proposed structure.

Step C

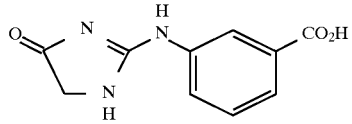

To a mixture of the product from Step B (250 mg, 1.0 mmol) in THF (2 mL) and methanol (2 mL) was added 1N NaOH solution (2 mL). The reaction was stirred at room temperature for 2 hours and concentrated in vacuo. The residue was suspended in water and carefully acidified to pH 4 with 1N HCl. The solid was collected by filtration and washed with water and ether to give the desired product, 190 mg. $^1$H NMR was consistent with the proposed structure.

Step D

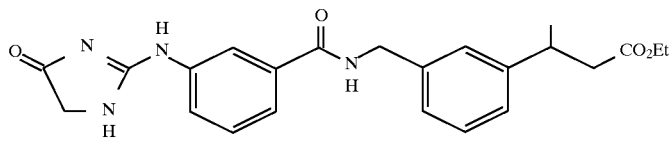

The product of Step C and the product from Step D in Example 64 were coupled according to a similar procedure as described in Example 34. ¹H NMR was consistent with the proposed structure.

Step E

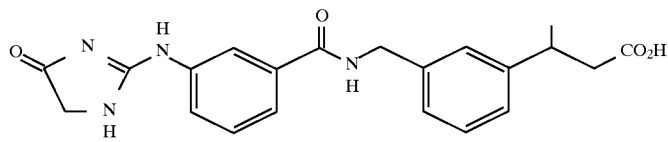

The product of Step D was hydrolyzed using the procedure in Step C. ¹H NMR was consistent with the proposed structure.

Exact mass calculated for $C_{21}H_{22}N_4O_4$: 394.3519, Found: 394.3520.

EXAMPLE 69

(±) 3-[[[[3-[(1H-benzimidazol-2-yl)amino]phenyl]carbonyl]amino]methyl]-β-methyl benzenepropanoic acid

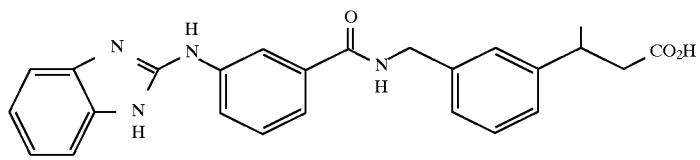

Step A

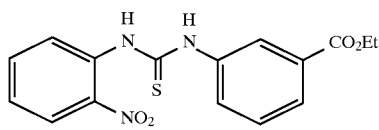

To a solution of 2-nitrophenylisothiocyanate (3.0 g, 16.6 mmol) in ethanol (45 mL) was added ethyl 3-aminobenzoate (2.75 g, 16.6 mmol) and triethylamine (2.6 mL, 18.6 mmol). The reaction solution was kept at room temperature for 17 hours. The reaction solution was concentrated in vacuo. The solid was washed with ether and water to give the desired product (3.3 g). ¹H NMR was consistent with the proposed structure.

Step B

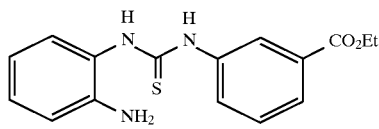

The product from Step A (2.3 g, 6.7 mmol) was hydrogenated with Raney nickel catalyst to yield the desired product (606 mg). ¹H NMR was consistent with the proposed structure.

Step C

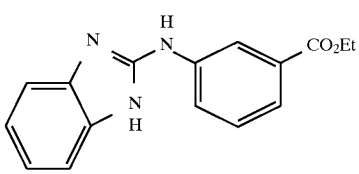

To a solution of the product from Step B (600 mg, 1.9 mmol) in ethanol (15 mL) was added mercury oxide (784 mg, 3.6 mmol) and sulfur (12 mg, 0.36 mmol). The mixture was heated at reflux for 3 hours. The mixture was cooled and filtered. The filtrate was concentrated in vacuo to afford the desired product (410 mg). ¹H NMR was consistent with the proposed structure.

Step D

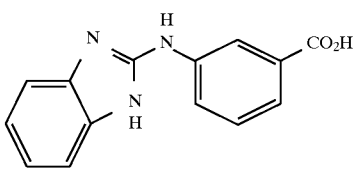

To a solution of the product from Step C (410 mg, 1.5 mmol) in methanol (18 mL) was added 1N NaOH solution (7 mL). The reaction solution was kept at room temperature for 5 hours. Volatiles were removed in vacuo and the residue acidified with 1M KHSO₄ solution. A solid precipitate was collected and dried in vacuo to give the desired product (425 mg). ¹H NMR was consistent with the proposed structure.

Step E

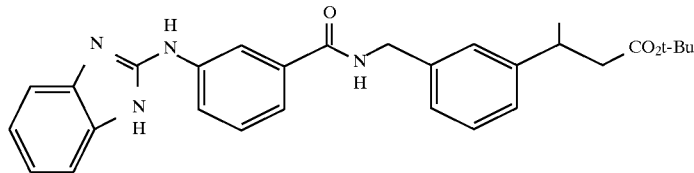

To a solution of the product from Step D (190 mg, 0.75 mmol) in DMF (5 mL) was added 1-(3-dimethylaminopropyl)-3-ethylcarbodiimide hydrochloride (EDC) (158 mg, 0.82 mmol), 1-hydroxybenzotriazole hydrate (HOBT) (112 mg, 0.82 mmol) and N-methylmorpholine (0.25 mL, 2.25 mmol). The compound of Example AK (206 mg, 0.82 mmol) in DMF (1 mL) was added via canula. The reaction mixture was stirred at room temperature for 16 hours. The mixture was concentrated in vacuo and the residue was purified by chromatography on silica gel (94:5:1 $CH_2Cl_2$:MeOH:$NH_4OH$) to afford the desired product (105 mg).

Step F

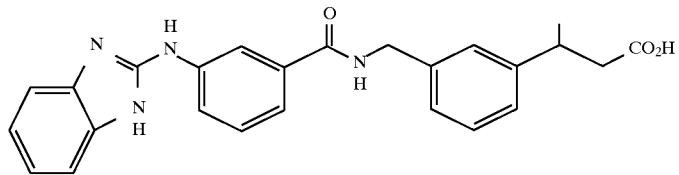

A solution of the product from Step E (105 mg) in a 1:1 $CH_2Cl_2$:TFA solution (4 mL) was kept at room temperature for 1 hour. The solution was concentrated with a stream of $N_2$. The residue was purified by chromatography on silica gel (85:14:1 $CH_2Cl_2$:MeOH:$NH_4OH$) to give the desired product.

Anal. calcd for $C_{25}H_{24}N_4O_3$+1.1 TFA: C, 58.98; H, 4.56; N, 10.11. Found: C, 59.08; H, 4.80; N, 10.04.

EXAMPLE 70

(±) 3-[[[[3-[(5-methoxy-1H-benzimidazol-2-yl)amino]phenyl]carbonyl]amino]methyl]-β-methyl benzenepropanoic acid, trifluoroacetate salt

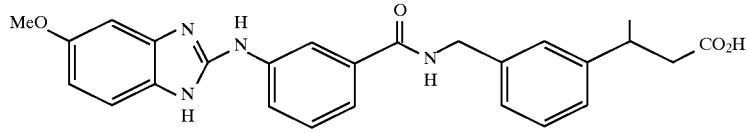

The title compound was prepared as in Example 69, starting from 5-methoxy-2-nitrophenylisothiocyanate.

Anal. calcd for $C_{26}H_{26}N_4O_4$+1.6 TFA: C, 54.71; H, 4.34; N, 8.73. Found: C, 54.71; H, 4.00; N, 8.70.

EXAMPLE 71

3-[2-[3-[(4,5-dihydro-1H-imidazol-2-yl)amino]phenyl]-2-hydroxyethoxy]benzenepropanoic acid, trifluoroacetate salt

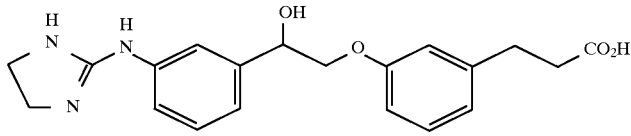

Step A

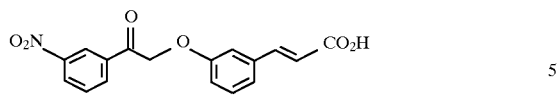

To a solution of methyl 3-hydroxycinnamate (14.3 g, 80 mmol) in acetone (400 mL) was added powdered potassium carbonate (12.16 g, 88 mmol) and 2-bromo-3'-nitroacetophenone. The reaction mixture was heated at reflux for 3.5 hours. The reaction mixture was cooled and filtered. The filtrate was concentrated in vacuo to give a dark brown gum. The solid was triturated with methanol to give a light brown powder, 12.6 g. $^1$H NMR was consistent with the proposed structure.

Step B

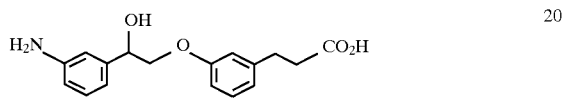

A solution of the product from Step A (3.0 g, 8.8 mmol) in methanol (100 mL) was hydrogenated with 5% Pd/C catalyst for 2 hours. The catalyst was removed by filtration and the filtrate concentrated to give the desired product, 2.9 g. $^1$H NMR was consistent with the proposed structure.

Step C

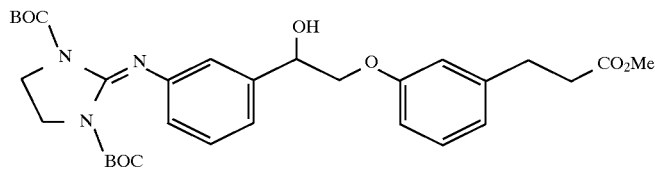

The product from Step B (345 mg, 1.1 mmol) was treated with N,N'-bis-(tert-butoxycarbonyl)-2-imidazolidinethione as described in Example 72, Step D to give the desired product (428 mg). $^1$H NMR was consistent with the proposed structure.

Step D

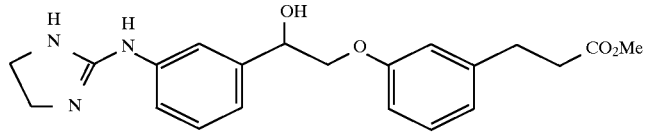

The product from Step C (420 mg) was deprotected in the same manner as described in Example 1 to give the desired product (160 mg). $^1$H NMR was consistent with the proposed structure.

Step E

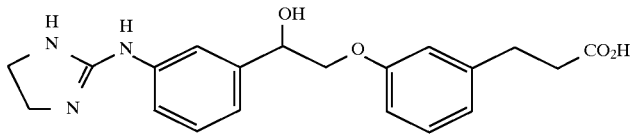

The product from Step D (150 mg, 0.4 mmol) was saponified with NaOH to give the desired product (91 mg).

Anal. calcd for $C_{20}H_{23}N_3O_4$+1.6 TFA: C, 50.52; H, 4.50; N, 7.61. Found: C, 50.91; H, 4.72; N, 7.22.

EXAMPLE 72

2-[3-[3-[3-[(4,5-dihydro-1H-imidazol-2-yl)amino] phenyl]-1-oxo-2-propenyl]phenoxy]acetic acid, trifluoroacetate salt hydrate

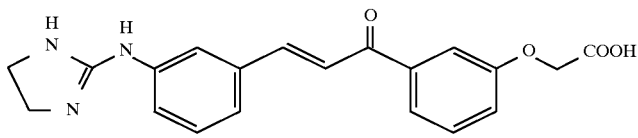

Step A

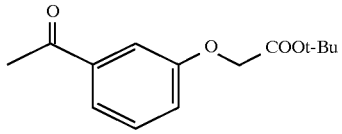

To a solution of 10.0 g (73.5 mmoles) of 3-hydroxyacetophenone and 13.0 ml (15.8 g, 80.9 mmoles) of t-butyl bromoacetate in of dimethylformamide (75 ml) was added 15.2 g (110 mmoles) of anhydrous potassium carbonate. The mixture was stirred in an 95° C. oil bath for 3 hours. After cooling, the mixture was partitioned between ethyl acetate and water, and the aqueous layer was further extracted with ethyl acetate. The combined organic extracts were washed with brine, dried over sodium sulfate, filtered and evaporated to give the above compound (17.0 g) as a water white oil. The structure was confirmed by $^1$H NMR.

Step B

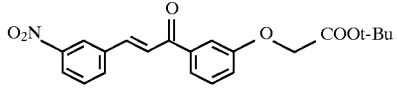

To a solution of 10.0 g (40.0 mmoles) of the product of Step A and 6.04g (4.10 mmoles) of 3-nitrobenzaldehyde in absolute ethanol (40 ml) was added a solution of 513 mg (9.14 mmoles) of potassium hydroxide in ethanol (5 ml), and the mixture stirred overnight at room temperature. The resulting solid was recovered by filtration, washed with ethanol, and air dried to give the above compound (7.92 g), as a nearly white solid.

Anal. Calcd. for $C_{21}H_{21}FNO_6.H_2O$ (MW 401.42): C, 62.84, H, 5.27, N, 3.49. Found: C, 63.13, H, 5.08, N, 3.57.

Step C

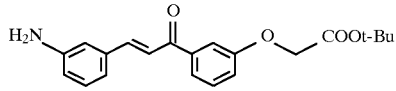

To a warm (60° C.) suspension of 7.57g (19.8 mmoles) of the product of Step B in ethanol (200 ml) was added 17.9 g (79.2 mmoles) of stannous chloride dihydrate as a solid. The mixture was stirred in an oil bath at 75° C. for 2 hours eventually forming a homogeneous solution. After cooling, the solvent was evaporated, and the residue partitioned between ethyl acetate and 1N aqueous sodium hydroxide. Following removal of precipitated salts by filtration, the organic layer was separated, dried over sodium sulfate, filtered, and evaporated. Chromatography of the residue over silica gel using 35% ethyl acetate—hexane as eluent gave the above compound (1.87 g) as a yellow oil. The structure was confirmed by $^1$H NMR.

Step D

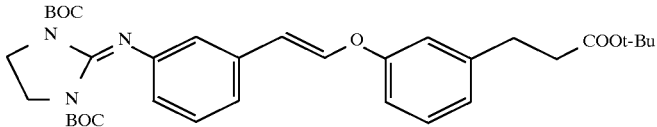

A mixture of 750 mg (2.12 mmoles) of the product of Step C (896 mg, 2.97 mmoles) of N,N'-bis-(tert-butoxycarbonyl)-2-imidazolidinethione (808 mg, 2.97 mmoles) of mercuric chloride, and (832 µl, 604 mg, 5.98 mmoles) triethylamine was stirred in an 85° C. oil bath for 3 hours. After cooling, the mixture was partitioned between ethyl acetate and water, filtered, and the organic layer separated. The organic layer was washed with brine, dried over sodium sulfate, filtered, and evaporated. Chromatography of the residue over silica gel using a gradient of 25–35% ethyl acetate—hexane as eluent gave the above compound (850 mg) as a yellowish foam. The structure was confirmed by $^1$H NMR.

Step E

A solution of 880 mg (1.37 mmoles) of the product of Step D in dichloromethane-trifluoroacetic acid (20 ml, 1:1) was stirred overnight at room temperature, and then concentrated. Reverse phase preparative HPLC of the residue using a gradient of 95:5 to 50:50 dilute aqueous trifluoroacetic acid and acetonitrile gave, after concentration of the appropriate fractions, the title compound (75mg) as a nearly pure white solid.

Anal. Calcd. for $C_{20}H_{19}N_3O_4 \cdot CF_3COOH \cdot 2.5H_2O$ (MW 486.45): C, 54.32, H, 4.14, N, 8.64. Found: C, 54.26, H, 4.39, N, 8.25.

EXAMPLE 73

2-[3-[3-[3-[(aminoiminomethyl)amino]phenyl]-1-oxopropenyl]phenoxy]acetic acid, monohydrochloride

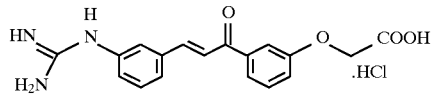

Step A

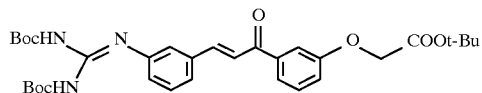

To a solution of 1.61 g (4.56 mmoles) of the product from Step C of Example 72 and (1.57 g, 5.70 mmoles) of bis-Boc thiourea in (48 ml) dimethylformamide was added (1.55 g, 5.70 mmoles) mercuric chloride, and then (1.8 ml, 1.3 g, 13 mmoles) triethylamine. The mixture was stirred overnight at room temperature, and then diluted with ethyl acetate and filtered. The filtrate was washed with water, dried over sodium sulfate, filtered, and evaporated. Chromatography of the residue over silica gel using 15% ethyl acetate—hexane as eluent gave the above compound (1.13 g) as a very pale yellow solid. The structure was confirmed by $^1H$ NMR.

Step B

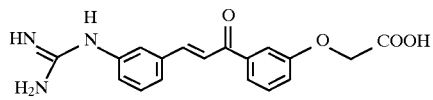

The above product of Step A (1.13 g, 1.99 mmoles) was dissolved in 1:1 dichloromethane-trifluoroacetic acid (30 ml) and after 2 hours was concentrated. Reverse phase preparative HPLC of the residue using a gradient of 80:20 to 50:50 dilute aqueous trifluoroacetic acid and acetonitrile gave, after concentration of the appropriate fractions, the above compound (as the zwitterion) (340 mg) as a nearly pure white solid.

Anal. Calcd. for $C_{18}H_{17}N_3O_4 \cdot 0.5H_2O$ (MW 348.36): C, 62.06, H, 4.92, N, 12.06. Found: C, 62.21, H, 4.99, N, 12.00.

Step C

A suspension of 120mg of the product from Step B in water (20 ml), 3N aqueous hydrochloric acid (2 ml), and methanol (10 ml) was kept at room temperature for 1 hour and then evaporated to give the title compound (130mg) as a nearly white solid.

Anal. Calcd. for $C_{18}H_{18}ClN_3O_4 \cdot 0.375H_2O$ (MW 375.81): C, 56.51, H, 4.74, N, 10.98. Found: C, 57.53, H, 4.83, N, 11.18.

EXAMPLE 74

3-[2-[3-[(aminoiminomethyl)amino]phenyl]ethynyl]-β-phenylbenzenepropanoic acid, trifluoroacetate salt

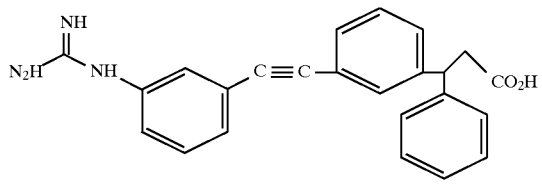

Step A

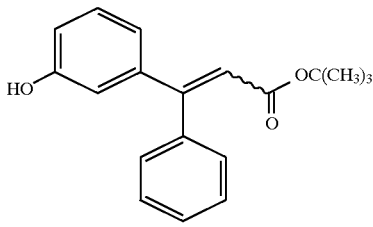

In a flame dried flask under $N_2$ at 0° C. was suspended sodium hydride (2.08 g, 60% dispersion) in dry THF (100 ml). This suspension was treated with a solution of 3-hydroxybenzophenone (10.0 g) in THF (50 ml) dropwise at 0°. After stirring for 30 minutes at 0°, a solution of trimethylsilyl chloride (5.86 g) in THF (25 ml) was added dropwise at 0°.

In another flame dried flask under $N_2$ at 0° was prepared a suspension of sodium hydride (2.40 g, 60% dispersion) in THF (50 ml). A solution of tert-butyl P,P-dimethyl phosphonoacetate (13.50 g) was added dropwise and the reaction allowed to stir and warm to room temperature over 1 hour. The contents of this flask was then added dropwise to the first flask at 0° and the reaction was allowed to stir and warm to room temperature overnight. The reaction mixture was then partitioned between ethyl acetate (500 ml) and 2N HCl (500 ml). The aqueous portion was extracted with additional ethyl acetate and the combined organic extracts were washed with water, saturated sodium chloride solution, dried over $Na_2SO_4$, concentrated, and purified on a flask column eluting with 20% ethyl acetate-80% hexane to afford a white solid (12.5 g). NMR was consistent with the proposed structure.

Step B

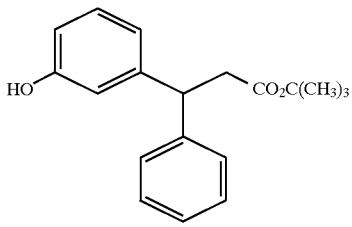

A solution of the product from Step A (12.4 g), ethanol (50 ml), and THF (50 ml) was hydrogenated at 5 psi for 5 hours at room temperature with Raney nickel. The reaction mixture was filtered, concentrated and purified on a flash column eluting with 20% ethyl acetate-80% hexane to afford the product (11.6 g) as a viscous oil. NMR was consistent with the proposed structure.

Step C

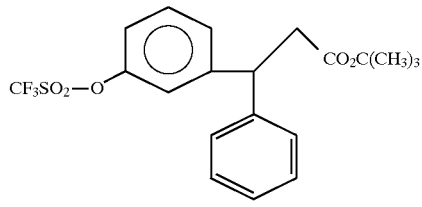

The reaction was run as described in Example AV using the product from Step B (11.6 g). The crude product was purified on a flash column eluting with 20% ethyl acetate—80% hexane to afford the product (15.4 g) as a viscous liquid. NMR was consistent with the proposed structure.

Step D

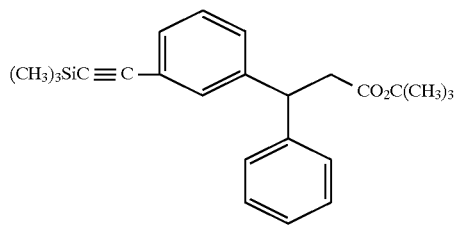

The above compound was prepared as described in Example AL from the compound produced in Step C (15.4 g). The crude product was purified on a flash column eluting with 10% ethyl acetate—90% hexane to afford the product (3.2 g) as a tan solid. NMR was consistent with the proposed structure.

Step E

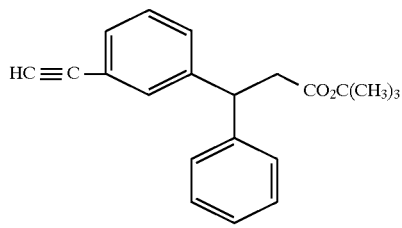

The above compound was prepared as described in Example AM from the product produced in Step D (3.2 g). The crude product was purified on a flash column eluting with 10% ethyl acetate—90% hexane to afford the product (2.0 g) as a viscous brown oil. NMR was consistent with the proposed structure.

Step F

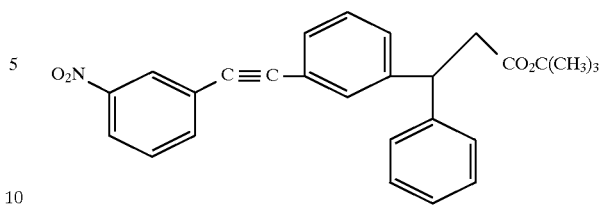

The above compound was prepared as described in Example AN from the compound produced in Step E (1.9 g). The crude product was purified on a flash column eluting with 20% ethyl acetate—80% hexane to afford the product as a brown oil. NMR was consistent with the proposed structure.

Step G

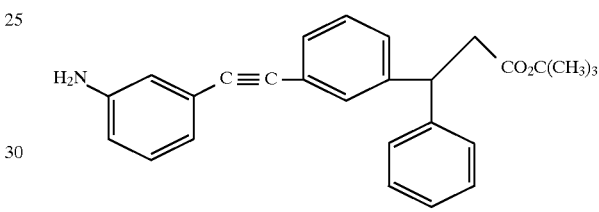

A mixture of the product from Step F (1.0 g), $SnCl_2$ (1.33 g), water (250 ml) and ethanol (25 ml) was refluxed for 90 minutes. The reaction mixture was cooled and partitioned between ethyl acetate and 10% potassium carbonate solution. The aqueous portion was extracted several times with ethyl acetate and the combined organic extracts were washed with saturated sodium chloride solution, dried over $Na_2SO_4$, concentrated, and purified on a flash column eluting with 30% ethyl acetate—70% hexane to afford the product (580 mg) as a viscous orange oil. NMR was consistent with the proposed structure.

Step H

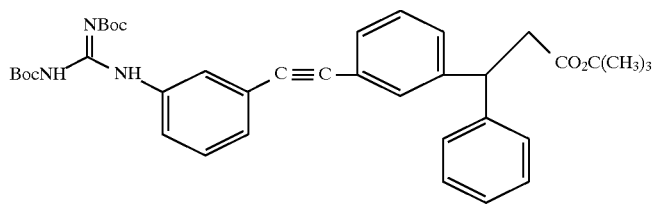

The reaction was run as described in Example Y using the product from Step G (220 mg). The crude product was purified on a flash column eluting with 10% ethyl acetate—90% hexane to afford the product (220 mg) as a light yellow powder. NMR was consistent with the proposed structure.

Step I

A solution of the product from Step H (220 mg) was stirred with methylene chloride (5 ml) and trifluoroacetic acid (5 ml) at room temperature for 1 hour. The solvent was removed in vacuo and the crude product was purified via reverse phase HPLC using a water (0.5% TFA) and acetonitrile gradient as eluant to afford a white powder (175 mg). NMR was consistent with the proposed structure.

Analysis: Calculated for $C_{24}H_{21}N_3O_2 \cdot 1.5$ TFA. C, 58.49; H, 4.09; N, 7.58. Found: C, 58.78; H, 4.20; N, 7.75.

EXAMPLE 75

3-[2E-[3-[(aminoiminomethyl)amino]phenyl]ethenyl]-β-phenylbenzenepropanoic Acid, Bis(trifluoroacetate) Salt

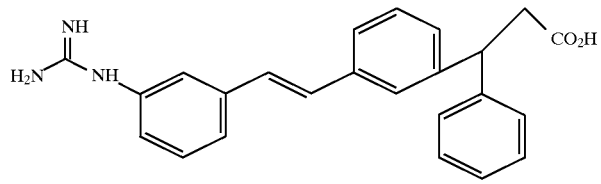

Step A

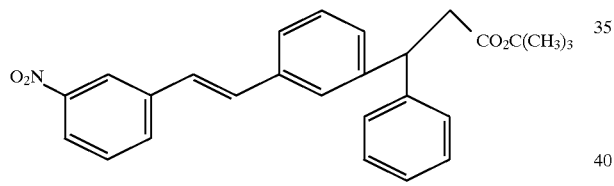

A mixture of the compound described in Step C, Example 74 (3.34 g), 3-nitro styrene (1.56 g), triethylamine (1.06 g), palladium acetate (19 mg) and triphenylphosphine (45 mg) were mixed in a thick walled tube and sealed with a screw cap. The tube was heated at 100° C. for 12 hours and then cooled. The reaction mixture was placed directly on a flash column and eluted with 10% ethyl acetate—90% hexane to afford the product (191 mg) as a light yellow solid. NMR was consistent with the proposed structure.

Step B

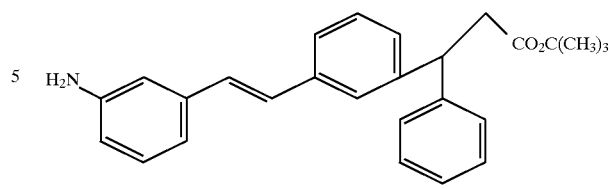

The above compound was prepared as described in Step G, Example 74 from the product produced in Step A (180 mg). The crude product was purified via flash chromatography eluting with 50% ethyl acetate—50% hexane to afford the compound (114 mg) as a golden oil. NMR was consistent with the proposed structure.

Step C

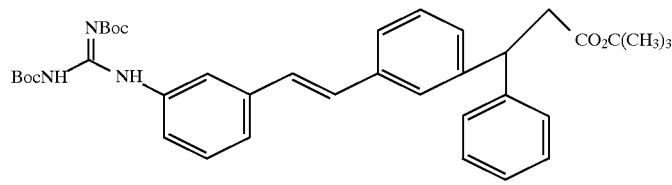

The above compound was prepared as described in Example Y using the compound (104 mg) prepared in Step B. The crude product was purified on a flash column eluting with 10% ethyl acetate—90% hexane to afford the desired product (157 mg) as a light brown solid. NMR was consistent with the proposed structure.

Step D

The title compound was prepared as described in Example 74, Step I from the product (153 mg) produced in Step C. The crude product was purified via reverse phase HPLC using a water (0.5% TFA) and acetonitrile gradient as eluant to afford white powder (92 mg). NMR was consistent with the proposed structure.

Analysis Calculated for $C_{24}H_{23}N_3O_2 \cdot 2.0$ TFA. C, 54.82; H, 4.11; N, 6.85. Found: C, 54.70; H, 4.04; N, 7.08.

EXAMPLE 76

3-[2Z-[3-[(aminoiminomethyl)amino]phenyl] ethenyl]-β-phenylbenzenepropanoic Acid, Bis (trifluoroacetate) Salt

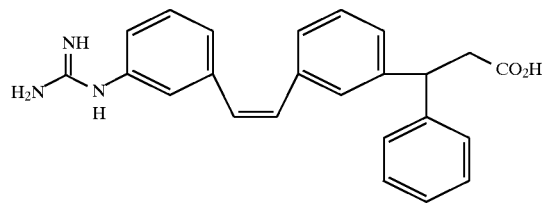

Step A

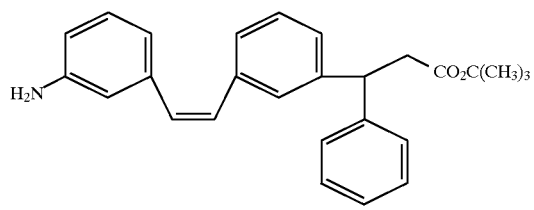

A mixture of the product produced in Step G, Example 74 (316 mg), triethylamine (236 mg), formic acid (40 mg) and 10% palladium on carbon (9 mg) was placed in a tube and sealed with a screw cap. The reaction was heated at 80° C. for 24 hours, cooled, filtered, and concentrated. The crude product was purified on a flash column eluting with 30% ethyl acetate—70% hexane to afford the product as a golden oil (113 mg). NMR was consistent with the proposed structure.

Step B

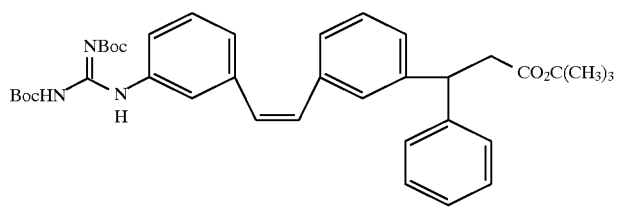

The reaction was run as described in Example Y using the product from Step A (113 mg). The crude product was purified on a flash column eluting with 10% ethyl acetate—90% hexane to afford an off white solid (140 mg). NMR was consistent with the proposed structure.

Step C

The title compound was prepared as described in Step I, Example 74 using the product produced in Step B (132 mg). The product was purified to yield a white solid (94 mg). NMR was consistent with the proposed structure.

Analysis Calculated for $C_{24}H_{23}N_3O_2 \cdot 2.0$ TFA. C, 54.82; H, 4.11; N, 6.85. Found C, 54.26; H, 3.96; N, 7.16.

EXAMPLE 77

β-[3-[[[3-[(aminoiminomethyl)amino]phenyl] sulfonyl]amino]phenyl]-3,5-dichlorobenzene Propanoic Acid, Trifluoroacetate Salt

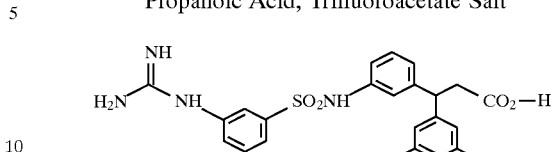

Step A

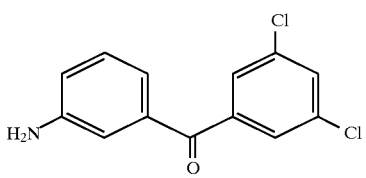

In a flame dried flask under $N_2$ was dissolved 3,5-dichlorobenzoylchloride (10.0 g) in dry THF (100 ml). The stirred reaction mixture was chilled to 50° C. and treated dropwise with a 1.0M solution of 3-[bis(trimethylsilyl)amino]-phenylmagnesium chloride (40 ml) (Aldrich) in THF. After the addition was completed, the reaction was allowed to warm to room temperature and then partitioned between ethyl acetate and 1N HCl. The mixture was adjusted to pH ~10 with 1N KOH and shook well in a separatory funnel. The layers were separated and the aqueous portion was extracted with additional ethyl acetate. The combined organic extracts were washed with saturated sodium chloride solution, dried over sodium sulfate, concentrated and purified on a flash column eluting with 25% ethyl acetate—75% hexane to afford a yellow solid (7.2 g). NMR was consistent with the proposed structure.

Step B

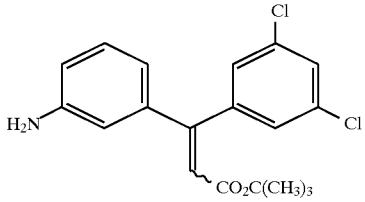

The reaction was run as described in Example E using the product produced in Step A (7.1 g). The crude product was purified on a flash column eluting with 30% ethyl acetate—70% hexane to afford viscous golden oil (5.1 g). NMR was consistent with the proposed structure.

Step C

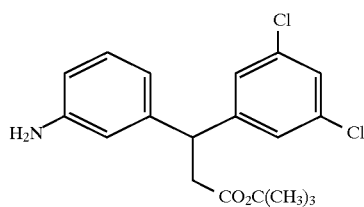

In a flame dried flask under $N_2$ was stirred a mixture of magnesium turnings (3.6 g), dry methanol (150 ml) and the compound produced in Step B (5.1 g). The reaction was stirred at room temperature (mildly exothermal) until all of the metal had dissolved. The reaction was then concentrated and partitioned between ethyl acetate and 2N HCl. The mixture was then adjusted to pH-11 with 2N KOH and shaken well in a separatory funnel. The layers were separated and the aqueous portion was extracted with additional ethyl acetate. The combined organic extracts were washed with saturated sodium chloride solution, dried over $Na_2SO_4$ and concentrated. The crude product was purified on a flash column eluting with 25% ethyl acetate—75% hexane to yield a golden oil (5.3 g). NMR was consistent with the proposed structure.

Step D

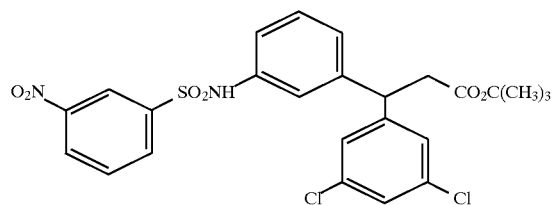

The reaction was run as described in Example G using the product produced in Step C (3.2 g). The crude product was purified on a flash column eluting with 30% ethyl acetate—70% hexane to afford a yellow gum (2.8 g). NMR was consistent with the proposed structure.

Step E

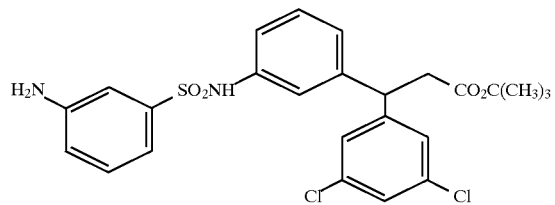

The reaction was run as described in Example 74, Step G, using the compound produced in Step D (2.7 g). The crude product was purified on a flash column eluting with 50% ethyl acetate—50% hexane to afford a white solid (2.1 g). NMR was consistent with the proposed structure.

Step F

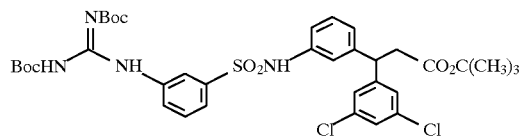

The reaction was run as described in Example Y using the product produced in Step E (340 mg). The crude product was purified on a flash column eluting with 20% ethyl acetate—80% hexane to yield a white solid (200 mg). NMR was consistent with the proposed structure.

Step G

The title compound was prepared as described in Example 74, Step I, using the product from Step F (180 mg). The crude material was purified in a similar fashion to afford a white solid (96 mg). NMR was consistent with the proposed structure.

Analysis Calculated for $C_{22}H_{20}N_4O_4C_2S \cdot 1.5$ TFA. C, 44.26; H, 3.19; N, 8.26; Cl, 10.45; S, 4.73. Found: C, 44.02; H, 3.27; N, 8.28; Cl, 10.29; S, 5.05.

EXAMPLE 78

β-[3-[[[3-[(aminoiminomethyl)amino]phenyl] sulfonyl]amino]phenyl]-3,5-difluorobenzenepropanoic Acid, Trifluoroacetate Salt

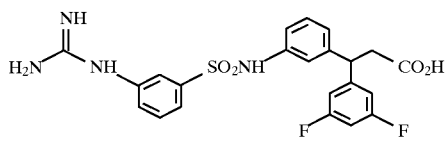

The above compound was prepared from 3,5-difluoro benzoyl chloride in a sequence of reactions as described in Example 77. NMR was consistent with the proposed structure.

Analysis Calculated for $C_{22}H_{20}N_4O_4F_2S \cdot 1.65$ TFA. C, 45.86; H, 3.29; N, 8.46; S, 4.84. Found: C, 45.56; H, 3.07; N, 8.61; S, 5.26.

EXAMPLE 79

β-[3-[[[3-[(aminoiminomethyl)amino]phenyl] sulfonyl]amino]phenyl]-4-fluorobenzenepropanoic Acid, Trifluoroacetate Salt

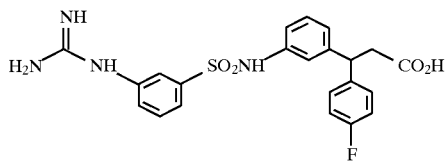

The above compound was prepared from 4-fluoro benzoyl chloride in a sequence of reactions as described in Example 77. NMR was consistent with the proposed structure.

Analysis Calculated for $C_{22}H_{21}N_4O_4FS \cdot 1.5$ TFA. C, 47.85; H, 3.61; N, 8.93; S, 5.11. Found: C, 47.69; H, 3.74; N, 9.14; S, 5.53.

EXAMPLE 80

β-[3-[[[3-[(aminoiminomethyl)amino]phenyl]sulfonyl]amino]phenyl]-3,4,5-trifluorobenzenepropanoic Acid, Trifluoroacetate Salt

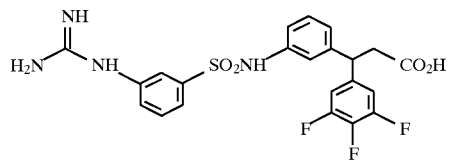

The above compound was prepared from 3,4,5-trifluoro benzoyl chloride in a sequence of reactions as described in Example 77. NMR was consistent with the proposed structure.

Analysis Calculated for $C_{22}H_{19}N_4O_4F_3S \cdot 1.25$ TFA. C, 46.34; H, 3.21; N, 8.82; S, 5.05. Found: C, 46.54; H, 3.15; N, 8.86; S, 5.29.

EXAMPLE 81

β-[3-[[[3-[(aminoiminomethyl)amino]phenyl]sulfonyl]amino]phenyl]perfluorobenzenepropanoic Acid, Trifluoroacetate Salt

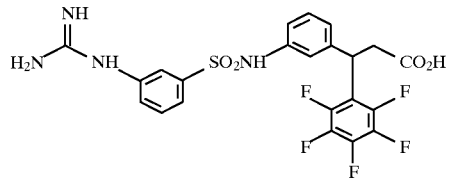

Step A

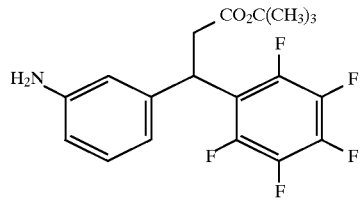

The above compound was prepared by hydrogenation of the precursor, which was prepared similarly as described in Example 77, Step B, with 5% platinum on carbon in ethanol at 60 psi for 16 hours at 50° C. The crude product was purified on a flash column eluting with 30% ethyl acetate—70% hexane. NMR was consistent with the proposed structure.

Step B

The title compound was prepared from the product produced in Step A through a series of similar reactions as described in Example 77, (Steps D through G). NMR was consistent with the proposed structure.

Analysis Calculated for $C_{22}H_{17}N_4O_4F_5S \cdot 1.5$ TFA. C, 42.93; H, 2.67; N, 8.01; S, 4.58. Found: C, 42.98; H, 2.56; N, 8.19; S, 5.02.

EXAMPLE 82

β-[3-[[[3-[(aminoiminomethyl)amino]phenyl]sulfonyl]amino]phenyl]-2,3,5,6-tetrafluorobenzenepropanoic Acid, Trifluoroacetate Salt

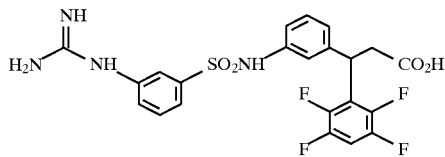

Step A

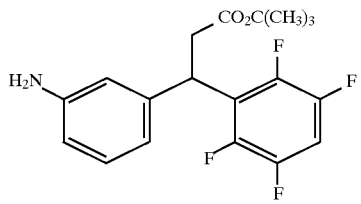

The above compound was prepared from a similar reaction as described in Example 77, Step C using the tetrafluoro analog which was prepared in an analogous fashion as described in Example 77, Step B. NMR was consistent with the proposed structure.

Step B

The title compound was prepared from the product produced in Step A by a series of similar reactions as described in Example 77, (Steps D through G). NMR was consistent with the proposed structure.

Analysis Calculated for $C_{22}H_{18}N_4O_4F_4S \cdot 1.8$ TFA. C, 42.96; H, 2.79; N, 7.83; S, 4.48. Found: C, 42.70; H, 2.84; N, 7.89; S, 4.89.

EXAMPLE 83

3,5-difluoro-β-[3-[[[3-[[[(phenylmethyl)amino]thiocarbonyl]amino]phenyl]sulfonyl]amino]phenyl]benzenepropanoic Acid

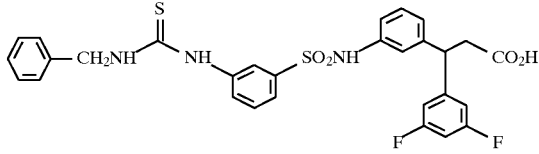

Step A

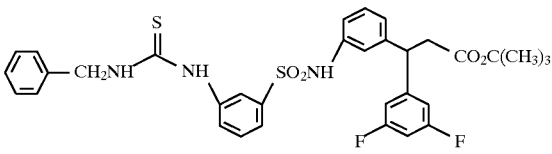

A mixture of the 3,5-difluoro precursor (648 mg), which was prepared in an analogous manner as described in Example 77, Step E, benzyl isothiocyanate (373 mg), and toluene (8 ml) was refluxed for 20 hours. The reaction was cooled and concentrated. The residue was dissolved in acetonitrile at room temperature and treated with several equivalents of benzyl amine for 1 hour. The reaction was concentrated and purified on a flash column eluting with 30% ethyl acetate—70% hexane to afford a white solid (330 mg). NMR was consistent with the proposed structure.

Step B

The title compound was prepared using the product prepared in Step A (115 mg) in a similar procedure as described in Example 74, Step I. The crude product was purified in similar style to yield a white solid (82 mg). NMR was consistent with the proposed structure.

Analysis Calculated for $C_{29}H_{25}N_3O_4F_2S_2 \cdot 0.25\ H_2O$. C, 59.42; H, 4.38; N, 7.17; S, 10.94. Found: C, 59.34; H, 4.34; N, 7.20; S, 11.22.

EXAMPLE 84

3,5-difluoro-β-[3-[[[3-[[[(phenylmethyl)imino]methyl]amino]phenyl]sulfonyl]amino]phenyl]benzenepropanoic Acid, Trifluoroacetate Salt

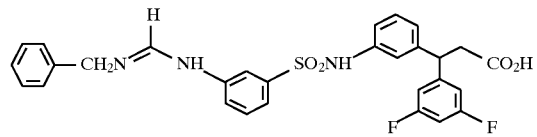

Step A

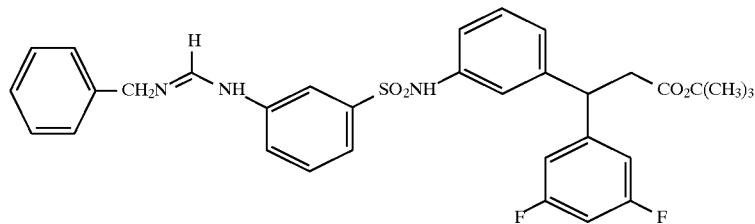

A solution of the product from Example 83, Step A (550 mg) in methanol (15 ml) was treated with several equivalents of Raney nickel and refluxed for 3 hours under $N_2$. The reaction mixture was cooled, filtered, concentrated and purified on a flash column eluting with 60% ethyl acetate—40% hexane to afford a white solid (233 mg). NMR was consistent with the proposed structure.

Step B

The title compound was prepared as described in Example 74, Step I using the product produced in Step A (233 mg). The crude product was purified in a similar fashion to yield a white solid (160 mg). NMR was consistent with the proposed structure.

Analysis Calculated for $C_{29}H_{25}N_3O_4F_2S \cdot 1.25$ TFA. C, 54.66; H, 3.82; N, 6.07; S, 4.63. Found: C, 54.37; H, 3.74; N, 6.00; S, 5.05.

EXAMPLE 87

3-[[3-[(aminoiminomethyl)amino]phenylthio]methyl]-β-phenylbenzenepropanoic Acid, Trifluoroacetate Salt

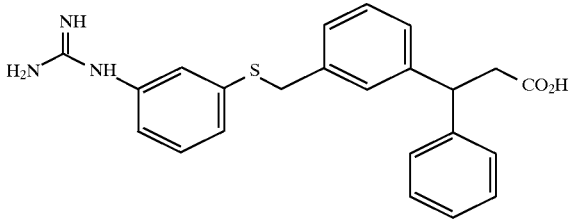

Step A

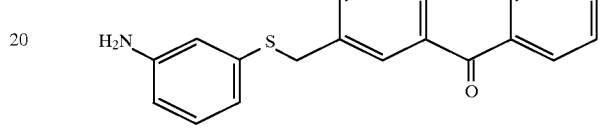

To a suspension of sodium hydride (1.0 g, 60% dispersion) in DMF (30 ml) at room temperature under $N_2$ was added dropwise a solution of 3-thioaniline in DMF (20 ml). After the addition was completed, the reaction mixture was stirred for 30 minutes and then a solution of 3-bromobenzophenone (Lancaster) in DMF (20 ml) was added dropwise at room temperature. After stirring for 1 hour, the solvent was removed and the residue was partitioned between ethyl acetate and water. The aqueous portion was extracted several times with ethyl acetate and the combined organic extracts were washed with water, saturated sodium chloride solution, dried over sodium sulfate, concentrated, and purified on a flash column eluting with 30% ethyl acetate—70% hexane to afford a yellow oil (5.9 g). NMR was consistent with the proposed structure.

Step B

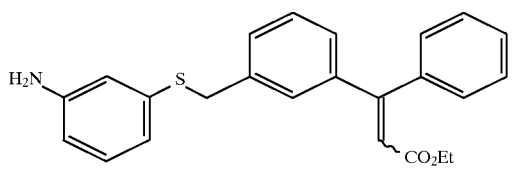

The reaction was run as described in Example E using the product produced in Step A (3.9 g) and triethyl phosphonoacetate (2.7 g). The crude product was purified on a flash column eluting with 25% ethyl acetate—75% hexane to yield viscous golden oil (3.5 g). NMR was consistent with the proposed structure.

Step C

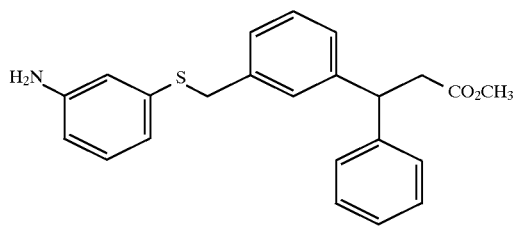

The reaction was run as described in Example 77, Step C using the product produced in Step B (3.4 g). The crude product was purified on a flash column eluting with 30% ethyl acetate—70% hexane to afford a viscous golden oil (3.0 g). NMR was consistent with the proposed structure.

Step D

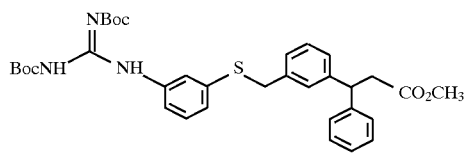

The above compound was prepared as described in Example Y using the compound produced in Step C (2.5 g). The crude product was purified on a flash column eluting with 15% ethyl acetate—85% hexane to afford a viscous oil (3.2 g). NMR was consistent with the proposed structure.

Step E

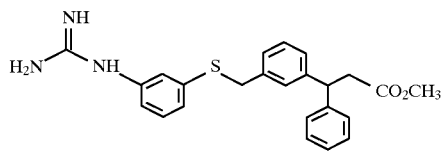

The above compound was prepared in a similar manner as described in Example 74, Step I using the product from Step D (900 mg). The crude product was purified in similar fashion to yield a clear glass (570 mg). NMR was consistent with the proposed structure.

Analysis Calculated for $C_{24}H_{25}N_3O_2S.1.5$ TFA. C, 54.91; H, 4.52; N, 7.12; S, 5.43. Found: C, 54.96; H, 4.56; N, 7.24; S, 5.49.

Step F

A solution of the product from Step E (350 mg) with 1N NaOH solution (5 ml), methanol (5 ml) and THF (10 ml) was stirred at room temperature for 18 hours. The reaction was then concentrated to dryness and the residue treated with a 1:1 solution of TFA and methylene chloride (10 ml) at room temperature for 1 hour. The solvents were then removed and the residue purified via reverse phase HPLC using a water (0.5% TFA) and acetonitrile gradient as eluant to afford a white solid (293 mg). NMR was consistent with the proposed structure.

Analysis Calculated for $C_{23}H_{23}N_3O_2S.1.1$ TFA. C, 57.01; H, 4.58; N, 7.91; S, 6.04. Found: C, 56.82; H, 4.77; N, 8.13; S, 6.31.

EXAMPLE 88

3-[[[3-[(aminoiminomethyl)amino]phenyl]sulfinyl]methyl]-β-phenylbenzenepropanoic Acid, Trifluoroacetate Salt

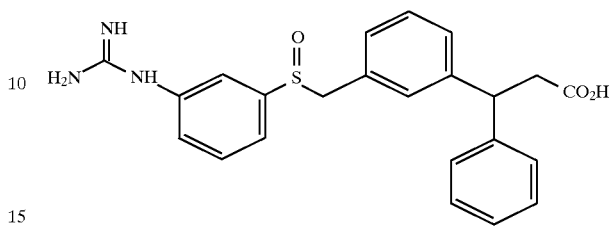

Step A

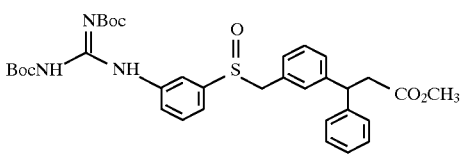

A solution of the product from Example 87, Step D (2.0 g) in methylene chloride (20 ml) was treated with tetra-n-butyl ammonium oxone (3.6 g) at room temperature for 30 minutes. The reaction mixture was then partitioned between water and methylene chloride. The aqueous phase was extracted with additional methylene chloride and the combined organic extracts were washed with water and saturated sodium chloride solution, dried over $Na_2SO_4$, concentrated and purified on a flash column eluting with 1:1 ethyl acetate—hexane to yield a white solid (1.4 g). NMR was consistent with the proposed structure.

Step B

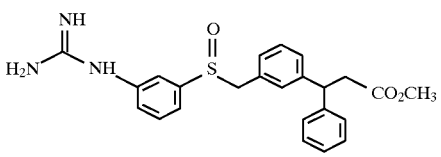

The title compound was prepared as described in Example 87, Step E using material from Step A (465 mg). The crude product was purified in similar manner to afford a white solid (372 mg). NMR was consistent with the proposed structure.

Analysis Calculated for $C_{24}H_{25}N_3O_3S.2.1$ TFA. C, 50.18; H, 4.05; N, 6.23; S, 4.75. Found: C, 49.97; H, 4.35; N, 6.35; S, 5.31.

Step C

The title compound was prepared as described in Example 87, Step F from the compound obtained from Step B (350 mg). The crude material was purified in similar style to afford a white powder (182 mg). NMR was consistent with the proposed structure.

Analysis Calculated for $C_{23}H_{23}N_3O_3S.1.6$ TFA. C, 52.10; H, 4.11; N, 6.96; S, 5.31. Found: C, 52.13; H, 4.25; N, 7.02; S, 5.49.

EXAMPLE 89

3-[[[3-[(aminoiminomethyl)amino]phenyl]sulfonyl]
methyl]-β-phenylbenzenepropanoic Acid,
Trifluoroacetate Salt

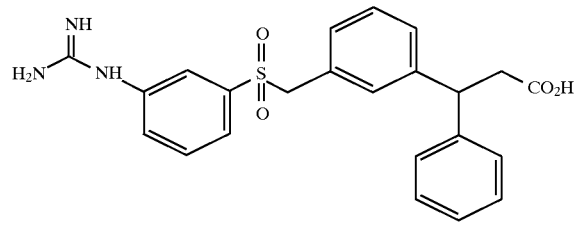

Step A

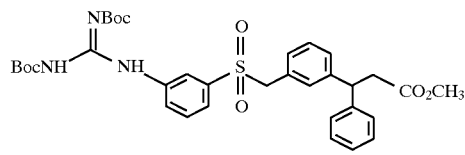

A solution of the product from Example 88, Step A (850 mg) in methylene chloride (10 ml) was treated with tetra-n-butyl ammonium oxone (3.0 g) at room temperature for 24 hours. The reaction mixture was worked up and purified as described in Example 88, Step A to yield a white solid (830 mg). NMR was consistent with the proposed structure.

Step B

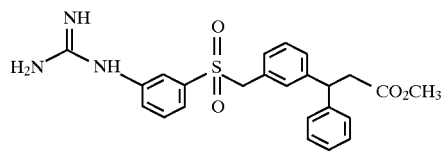

The above compound was prepared as described in Example 88, Step B from the compound prepared from Step A (500 mg). The crude product was purified in a similar fashion to afford a white solid (494 mg). NMR was consistent with the proposed structure.

Analysis Calculated for $C_{24}H_{25}N_3O_4S.1.75$ TFA. C, 50.73; H, 4.14; N, 6.45; S, 4.92. Found: C, 50.62; H, 4.09; N, 6.75; S, 4.82.

Step C

The title compound was prepared as described in Example 87, Step F using the product produced in Step B (500 mg). The crude material was purified in similar fashion to afford a white solid (250 mg). NMR was consistent with the proposed structure.

Analysis Calculated for $C_{23}H_{23}N_3O_4S.1.2$ TFA. C, 53.12; H, 4.25; N, 7.32; S, 5.58. Found: C, 53.34; H, 4.50; N. 7.46; S, 5.90.

EXAMPLE 90

β-[3-[[[3-[[amino[(aminocarbonyl)imino]methyl]
amino]phenyl]sulfonyl]amino]phenyl]-3,5-
dichlorobenzenepropanoic Acid, Trifluoroacetate
Salt

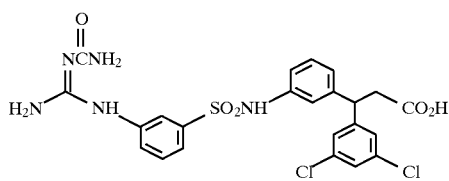

Step A

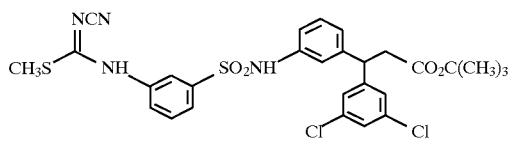

The above compound was prepared as described in Example 14, from the compound prepared from Example 77, Step E (1.0 g). The reaction was worked up and purified in a similar manner to afford a white solid (725 mg). NMR was consistent with the proposed structure.

Step B

The title compound was prepared from the product obtained in Step A utilizing the reactions described in Examples 15 and 16. The crude product was purified in similar fashion. NMR was consistent with the proposed structure.

Analysis Calculated for $C_{23}H_{21}N_5O_5SCl_2.1.5$ TFA. C, 43.29; H, 3.14; N, 9.71; Cl, 9.83; S, 4.44. Found C, 43.24; H, 3.05; N, 9.53; Cl, 9.97; S, 4.80.

EXAMPLE 91

β-[3-[[[3-[[amino[(aminocarbonyl)imino]methyl]
amino]phenyl]sulfonyl]amino]phenyl]-3,5-
difluorobenzenepropanoic Acid, Trifluoroacetate
Salt

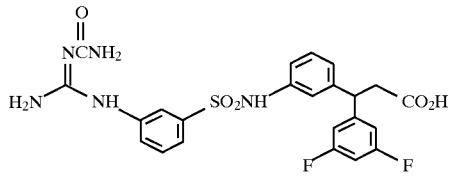

The above compound was prepared via the same sequence of reactions as described in Example 90 from the corresponding 3,5-difluoro intermediate. The crude material was purified in a similar manner. NMR was consistent with the proposed structure.

Analysis Calculated for $C_{23}H_{21}N_5O_5SF_2.1.4$ TFA. C, 45.76; H, 3.33; N, 10.34; S, 4.74. Found: C, 45.80; H, 3.36; N, 10.41; S, 5.18.

EXAMPLE 94

3-[[[3-[(aminoiminomethyl)amino]phenyl]sulfonyl]
amino]-β-ethylbenzenepropanoic Acid,
Trifluoroacetate Salt

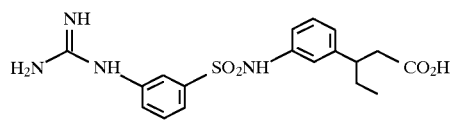

Step A

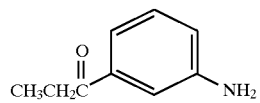

The above compound was prepared in an analogous manner as described in Example 77, Step A using propionyl chloride (5.0 g). The crude product was purified in a similar style to afford a viscous oil (2.4 g). NMR was consistent with the proposed structure.

Step B

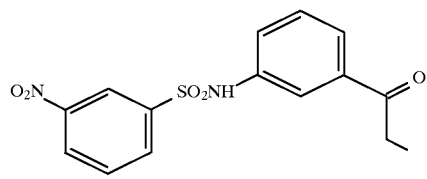

The above compound was prepared from the compound produced in Step A (2.4 g) utilizing similar reaction conditions as described in Example G. NMR was consistent with the proposed structure.

Step C

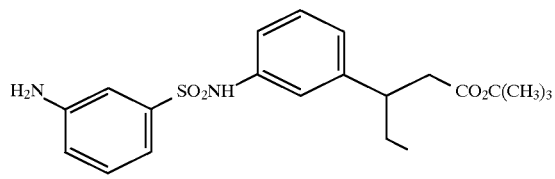

The above compound was prepared from the compound produced in Step B utilizing the reactions described in Examples E and F. NMR was consistent with the proposed structure.

Step D

The title compound was prepared from the compound produced in Step C using the methodologies described in Examples 1 and 74, Step I. NMR was consistent with the proposed structure.

Analysis Calculated for $C_{18}H_{22}N_4O_4S \cdot 1.7$ TFA. C, 43.99; H, 4.09; N, 9.59; S, 5.49. Found: C, 44.03; H, 4.11; N, 9.85; S, 5.73.

EXAMPLE 95

3-[[[3-[[amino[(aminocarbonyl)imino]methyl]
amino]phenyl]sulfonyl]amino]-β-
ethylbenzenepropanoic Acid, Trifluoroacetate Salt

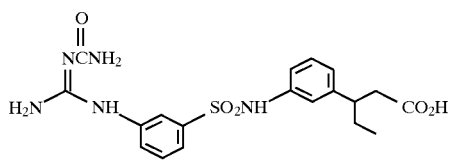

The above compound was prepared from the product produced in Example 94, Step C utilizing the reaction conditions described in Example 14 through 16. NMR was consistent with the proposed structure.

Analysis Calculated for $C_{19}H_{23}N_5O_5S \cdot 1.4$ TFA. C, 44.15; H, 4.15; N, 11.81; S, 5.41. Found: C, 44.14; H, 4.08; N, 11.65; S, 5.65.

EXAMPLE 96

3-[[3-[(aminoiminomethyl)amino]phenyl]methoxy]-
β-phenylbenzenepropanoic Acid, Trifluoroacetate
Salt

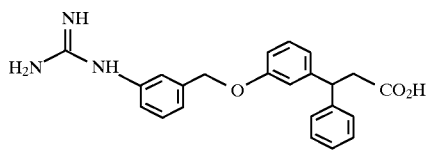

Step A

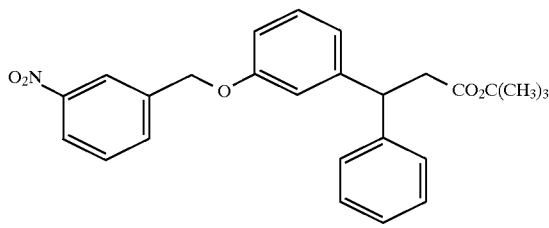

A solution of the product produced in Example 74, Step B (1.0 g), 3-nitrobenzyl bromide (735 mg), potassium carbonate (967 mg) and DMF (20 ml) was stirred at room temperature overnight. The reaction was partitioned between ethyl acetate and water and the aqueous portion was extracted with additional ethyl acetate. The combined organic extracts were washed with water, saturated sodium chloride solution, dried over $Na_2SO_4$, concentrated and purified on a flash column eluting with 20% ethyl acetate—80% hexane to afford a viscous oil (1.3 g). NMR was consistent with the proposed structure.

Step B

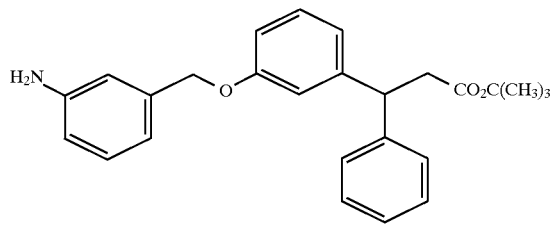

A solution of the product produced in Step A (1.3 g) in ethanol (40 ml) was hydrogenated under an atmosphere of 5 psi of hydrogen at room temperature for 3 hours using 3% platinum on carbon poisoned with sulfur. The crude product was purified on a flash column eluting with 20% ethyl acetate—80% hexane to afford a golden oil (1.1 g). NMR was consistent with the proposed structure.

Step C

The title compound was prepared from the product produced in Step B using the procedures described in Examples I and 74, Step I. The product was purified as previously described. NMR was consistent with the proposed structure.

Analysis Calculated for $C_{23}H_{23}N_3O_3 \cdot 1.15$ TFA$\cdot 0.5H_2O$. C, 57.38; H, 4.79; N, 7.93. Found: C, 57.28; H, 4.63; N, 8.19.

EXAMPLE 97

3,5-difluoro-β-[3-[[[3-[(1,4,5,6-tetrahydropyrimidin-2-yl)amino]phenyl]sulfonyl]amino]phenyl]benzenepropanoic Acid, Bis(trifluoroacetate) Salt

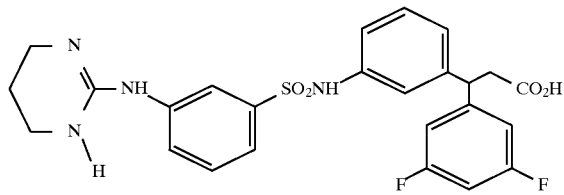

The above compound was prepared using the 3,5 difluoro precursor similarly as described in Example 77, Step E and coupling with N,N'-bis-(tert-butoxycarbonyl)-2-(1H)-tetrahydropyrimidinethione (using the same conditions described in Example I) followed by deprotection as described in Example 74, Step I. NMR was consistent with the proposed structure.

Analysis Calculated for $C_{25}H_{24}N_4O_4F_2S \cdot 2TFA$. C, 46.91; H, 3.53; N, 7.54; S, 4.32. Found: C, 47.11; H, 3.67; N, 7.78; S, 4.50.

EXAMPLE 98

β-[3-[[[3-[(4,5-dihydro-1H-imidazol-2-yl)amino]phenyl]sulfonyl]amino]phenyl]-3,5-difluorobenzenepropanoic Acid, Trifluoroacetate Salt

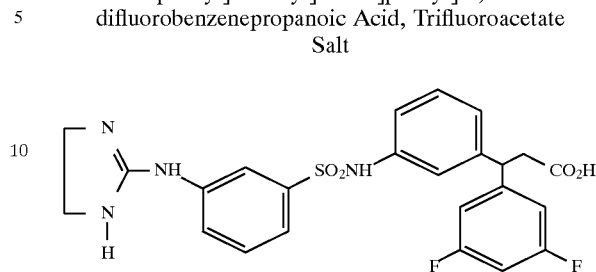

The above compound was prepared using the 3,5-difluoro precursor substantially as described in Example 77, Step E and coupling with, N,N'-bis-(tert-butoxycarbonyl)-2 imidazolidinethione (using the same conditions described in Example I) followed by deprotection as described in Example 74, Step I. NMR was consistent with the proposed structure.

Analysis Calculated for $C_{25}H_{25}N_3O_3F_2S \cdot 1.8$ TFA. C, 46.97; H, 3.40; N, 7.94; S, 4.54. Found: C, 46.84; H, 3.50; N, 8.08; S, 4.90.

EXAMPLE 99

3-[[3-[(4,5-dihydro-1H-imidazol-2-yl)amino]phenyl]methoxy]-β-phenylbenzenepropanoic Acid, Trifluoroacetate Salt

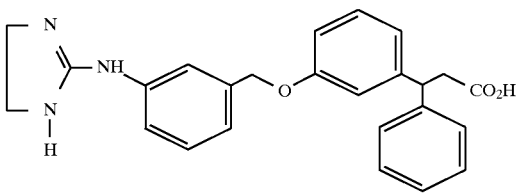

The above compound was prepared from the product produced in Example 96, Step B utilizing the methodology described in Example 98. NMR was consistent with the proposed structure.

Analysis Calculated for $C_{25}H_{25}N_3O_3S \cdot 1.5$ TFA. C, 57.34; N, 4.55; N, 7.16. Found: C, 57.65; H, 4.48; N, 7.30.

EXAMPLE 100

3-[(aminoiminomethyl)amino]-N-[3-(3,4-dihydro-2-oxo-2H-benzopyran-4-yl)phenyl]benzenesulfonamide, Trifluoroacetate Salt

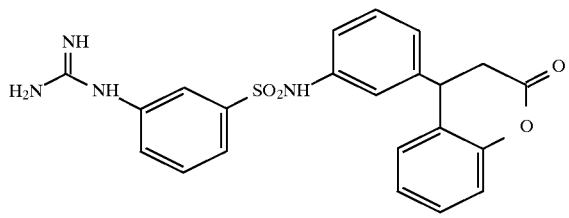

Step A

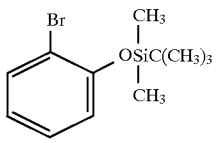

A solution of 2-bromophenol (10.0 g), dimethyl-t-butyl silyl chloride (9.8 g), imidazole (6.8 g) and DMF (100 ml) was stirred at room temperature for 18 hours. The reaction was partitioned between ethyl acetate and water and the aqueous portion was extracted with additional ethyl acetate. The combined organic extracts were washed with water, saturated sodium chloride solution, dried over sodium sulfate, concentrated and purified on a flash column eluting with 5% ethyl acetate—95% hexane to afford a colorless liquid (15.5 g). NMR was consistent with the proposed structure.

Step B

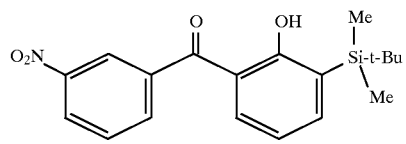

A Grignard reagent was prepared from the product produced in Step A (15.5 g) and magnesium turnings (1.3 g) in THF (150 ml). The Grignard reagent was added dropwise to a solution of 3-nitrobenzaldehyde in THF (50 ml) at room temperature. The reaction was stirred for 1 hour and then quenched with 1N HCl. The mixture was then partitioned between water and ethyl acetate. The aqueous portion was extracted several times with ethyl acetate and then the combined organic extracts were washed with water, saturated sodium chloride, dried over $Na_2SO_4$, concentrated and purified on a flash column eluting 20% EA—80% hexane to yield a yellow solid (9.2 g). NMR was consistent with the proposed structure.

Step C

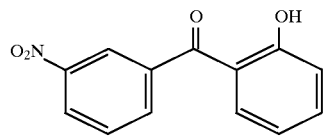

A solution of the product produced in Step B (3.9 g) was stirred at room temperature with a 1:1 solution of TFA and methylene chloride (50 ml) for 18 hours. The solvent was removed and the residue dried under high vacuum at 60° for 1 hour to afford a yellow solid (2.9 g). This material was used without further purification. NMR was consistent with the proposed structure.

Step D

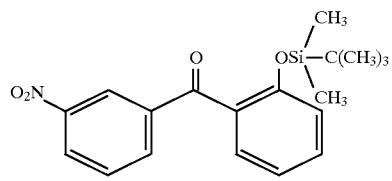

The above compound was prepared from the product produced in Step C (2.8 g) using the procedure described in Step A to yield a colorless oil (3.7 g) after purification via flash column eluting with 10% ethyl acetate—90% hexane. NMR was consistent with the proposed structure.

Step E

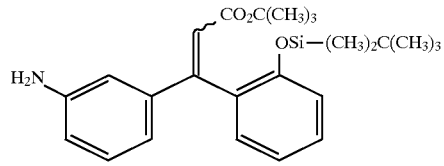

The above compound was prepared from the product produced in Step D using the methodologies described in Examples E and 74, Step G. The crude product was purified on a flash column eluting with 25% ethyl acetate—75% hexane. NMR was consistent with the proposed structure.

Step F

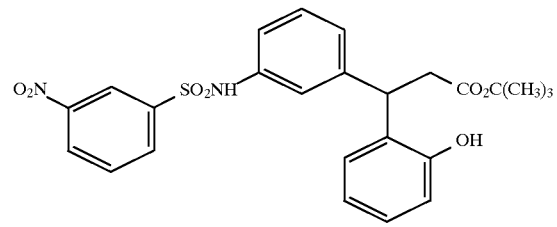

The above compound was prepared from the product produced in Step E using the procedures described in Example 77, Step C and Example G. The crude product was purified on a flash column eluting with 40% ethyl acetate—60% hexane. NMR was consistent with the proposed structure.

Step G

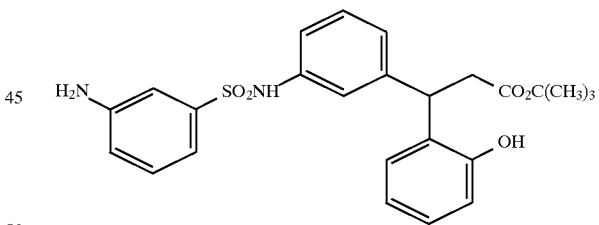

The above compound was prepared from the product produced in Step F utilizing the procedure described in Example 74, Step G. The crude product was purified on a flash column eluting with 1:1 ethyl acetate-hexane. NMR was consistent with the proposed structure.

Step H

The title compound was prepared from the product produced in Step G using the procedures described in Examples I and 74, Step I. NMR was consistent with the proposed structure.

Analysis Calculated for $C_{22}H_{20}N_4O_4S.1.75$ TFA. C, 48.00; H, 3.79; N, 8.96; S. 5.13. Found: C, 47.96; H, 3.48; N, 8.64; S, 5.44.

EXAMPLE 101

3-[(4,5-dihydro-1H-imidazol-2-yl)amino]-N-[3-(3,4-dihydro-2-oxo-2H-benzopyran-4-yl)phenyl]benzenesulfonamide, Trifluoroacetate Salt

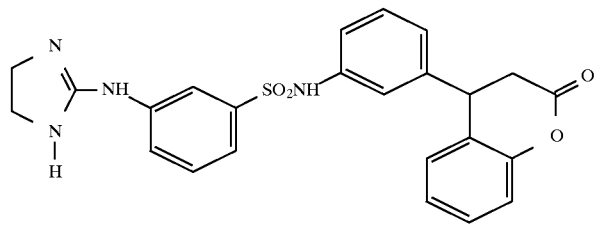

The above compound was prepared from the product produced in Example 100, Step G utilizing the methodology described in Example 98. NMR was consistent with the proposed structure.

Analysis Calculated for $C_{24}H_{22}N_4O_4S$ 1.75 TFA. C, 49.89; H, 3.62; N, 8.46; S, 4.84. Found: C, 50.10; H, 3.46; N, 8.48; S, 5.18.

EXAMPLE 102

Sodium β-[3-[[[3[(aminoiminomethyl)amino]phenyl]-sulfonyl]amino]phenyl]-2-hydroxybenzenepropanoate, Trifluoroacetate Salt

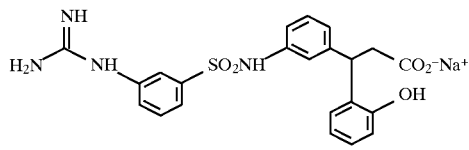

A mixture of the product produced in Example 100, Step H (113 mg), acetonitrile (2 ml), ethanol (2 ml) and 1N sodium hydroxide solution (0.5 ml) was stirred at room temperature overnight. The reaction mixture was concentrated to dryness and the residue taken up in ethanol and filtered through glass wool and reconcentrated. The residue was dried at 50° C. under high vacuum for 4 hours to afford a white solid (110 mg). NMR was consistent with the proposed structure.

The activity of the compounds of the present invention was tested in the following assays. The results of testing in the assays are tabulated in Table 1.

VITRONECTIN ADHESION ASSAY
MATERIALS

Human vitronectin receptor($\alpha_v\beta_3$) was purified from human placenta as previously described [Pytela et al., *Methods in Enzymology*, 144:475–489 (1987)). Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3):1415–1421 (1991)]. Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

METHODS
Solid Phase Receptor Assays

This assay was essentially the same as previously reported [Niiya et al., *Blood*, 70:475–483 (1987)]. The purified human vitronectin receptor ($\alpha_v\beta_3$) was diluted from stock solutions to 1.0 μg/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates were emptied and 200 μL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was $1.0 \times 10^{-4}$M. The competition occurred for two hours after which all wells were washed with a plate washer as before. Affinity purified horseradish peroxidase labeled goat antibiotin antibody was diluted 1:3000 in $TBS^{+++}$/BSA and 125 μL were added to each well. After 30 minutes, the plates were washed and incubated with OPD/$H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and %CV were determined for duplicate concentrations. The mean $A_{450}$ values were normalized to the mean of four maximum-binding controls (no competitor added)(B-MAX). The normalized values were subjected to a four parameter curve fit algorithm [Rodbard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

PURIFIED IIb/IIIa RECEPTOR ASSAY
MATERIALS

Human fibrinogen receptor ($\alpha_{IIb}\beta_3$) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

METHODS

Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70(1987):475–483. The purified human fibrinogen receptor ($\alpha_{IIb}\beta_3$) was diluted from stock solutions to 1.0 μg/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates were emptied and 200 μL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was $1.0 \times 10^{-4}$ M. The competition occurred for two hours after which all wells were washed with a plate washer as before. Affinity purified horseradish peroxidase labeled goat antibiotin antibody was diluted 1:3000 in $TBS^{+++}$/BSA and 125 μL were added to each well. After 30 minutes, the plates were washed and incubated with $ODD/H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and %CV were determined for duplicate concentrations. The mean $A_{450}$ values were normalized to the mean of four maximum-binding controls (no competitor added) (B-MAX). The normalized values were subjected to a four parameter curve fit algorithm, [Robard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino)-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

TABLE 1

| Example | AvB3 IC50 (nM) | IIb/IIIa IC50 (nM) |
|---|---|---|
| 1 | 16.7 | 625 |
| 2 | 499 | 3760 |
| 3 | 1.66 | 11.3 |
| 5 | 15300 | 21600 |
| 6 | 170 | 2380 |
| 8 | 641 | 11600 |
| 10 | 144 | 5540 |
| 11 | 554 | 2440 |
| 13 | 163 | 11800 |
| 15 | 40.4 | 1360 |
| 19 | >100000 | 57600 |
| 23 | >10000 | 4350 |
| 25 | 7460 | 26900 |
| 27 | 2120 | 7880 |
| 28 | >100000 | >100000 |
| 29 | 9370 | 32000 |
| 30 | >100000 | >100000 |
| 31 | 3570 | 5360 |
| 34 | 2930 | 66100 |
| 35 | 183 | 6080 |
| 36 | 13700 | 72400 |
| 37 | 32200 | 79000 |
| 38 | 8.95 | 364 |
| 39 | 8560 | 62400 |
| 40 | 11.6 | 2260 |
| 41 | 11300 | >100000 |
| 42 | 11.7 | 472 |
| 43 | 7.18 | 798 |
| 44 | 3210 | 94 |
| 45 | 72.3 | 1370 |
| 46 | 2440 | 2280 |
| 47 | 36500 | >100000 |
| 49 | 1680 | 12700 |
| 50 | >100000 | 55500 |
| 51 | 3090 | 10700 |
| 52 | 16600 | 39700 |
| 53 | 1670 | 2640 |
| 54 | 19.8 | 145 |
| 55 | 108 | 13400 |
| 56 | 6.88 | 1310 |
| 57 | 189 | 17600 |
| 58 | 11.6 | 5180 |
| 59 | 3.88 | 3130 |
| 60 | 4.58 | 286 |
| 61 | 1.33 | 712 |
| 62 | 0.87 | 1900 |
| 63 | 23.5 | 454 |
| 64 | 199 | 26400 |
| 65 | 23.0 | 4010 |
| 67 | 122 | 12900 |
| 69 | 425 | 10100 |
| 70 | 1710 | 7660 |
| 71 | 30.4 | 9750 |
| 72 | 168 | 8100 |
| 73 | 589 | 11300 |
| 74 | 1480 | 20100 |
| 75 | 54.5 | 6150 |
| 76 | 87.0 | 1770 |
| 77 | 32.5 | 5820 |
| 78 | 2.54 | 803 |
| 79 | 10.0 | 327 |
| 80 | 13.0 | 1370 |
| 81 | 86.0 | 2550 |
| 82 | 191 | 11700 |
| 83 | 122 | 18900 |
| 84 | 82.0 | 15100 |
| 87 | 51.2 | 3300 |
| 88 | 19.6 | 870 |
| 89 | 4.56 | 799 |
| 90 | 88.9 | 13800 |
| 91 | 8.39 | 1070 |
| 94 | 12.1 | 2050 |
| 95 | 35.7 | 8450 |
| 96 | 435 | 2280 |
| 97 | 0.75 | 262 |

TABLE 1-continued

| Example | AvB3 IC50 (nM) | IIb/IIIa IC50 (nM) |
|---|---|---|
| 98 | 0.85 | 642 |
| 99 | 48.6 | 1000 |
| 100 | 21.8 | 2340 |
| 101 | 50.3 | 3250 |
| 102 | 23.2 | 706 |

What is claimed is:

1. A compound of the formula

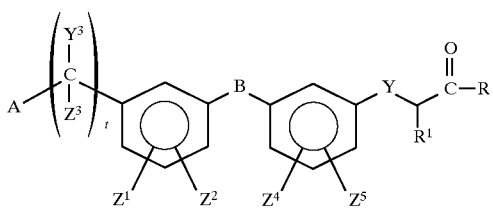

or a pharmaceutically acceptable salt thereof, wherein
A is

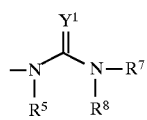

wherein $Y^1$ is selected from the group consisting of N—$R^2$, O, and S;

$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy, oxo and phenyl; or $R^2$ taken together with $R^7$ forms a 5 membered heteroaromatic ring; or $R^2$ taken together with $R^7$ forms a 5 membered heteroaromatic ring fused with a phenyl group optionally substituted with one or more substituent selected from the group consisting of alkoxycarbonyl and alkoxy;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —$SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein $R^{10}$ is defined above; or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl; or A is

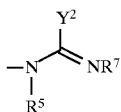

wherein

Y$^2$ is selected from the group consisting of hydrogen; alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; —S—R$^9$ and —O—R$^9$ wherein R$^9$ is selected from the group consisting of H; alkyl; aralkyl; aryl; alkenyl; and alkynyl; or R$^9$ taken together with R$^7$ forms a 4–12 membered mononitrogen containing sulfur or oxygen containing heterocyclic ring; and R$^5$ and R$^7$ are as defined above; or Y$^2$ (when Y$^2$ is carbon) taken together with R$^7$ forms a 4–12 membered mononitrogen containing ring optionally substituted with alkyl, aryl or hydroxy; or A is selected from the group consisting of

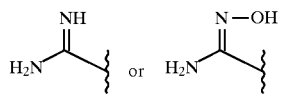

Z$^1$, Z$^2$, Z$^4$ and Z$^5$ are independently selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles; and A, wherein A is defined above;

B is selected from the group consisting of

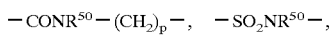

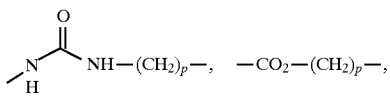

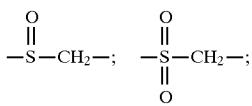

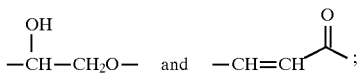

wherein p is an integer selected from the group consisting of 0, 1 and 2; wherein n is an integer selected from the group consisting of 0, 1, 2 and 3; R$^{50}$ is selected from the group consisting of H and alkyl;

Y is selected from the group consisting of

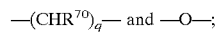

wherein q is an integer selected from the group consisting of 0 and 1; R$^{70}$ is selected from the group consisting of H, alkyl, aryl and aryl substituted with one or more substituent selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles;

t is an integer 0, 1 or 2;

R is X—R$^3$ wherein X is selected from the group consisting of 0, S and NR , wherein R$^3$ and R$^4$ are independently selected from the group consisting of hydrogen; alkyl; alkenyl; alkynyl; haloalkyl; aryl; arylalkyl; sugars; steroids and in the case of the free acid, all pharmaceutically acceptable salts thereof; or X—R$^3$ is

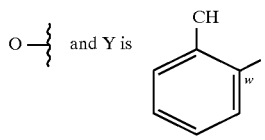

wherein the X—R$^3$ group is attached to the phenyl of the Y group at the para position to form a lactone;

Y$^3$ and Z$^3$ are independently selected from the group consisting of H, alkyl, aryl, cycloalkyl and aralkyl;

R$^1$ is selected from the group consisting of hydrogen; alkyl; aryl;

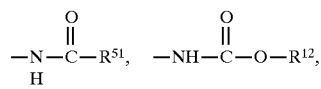

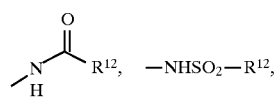

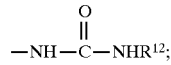

R$^{12}$ is selected from the group consisting of H, alkyl, cycloalkyl, aralkyl and aryl; and R$^{51}$ is selected from the group consisting of N-substituted pyrrolidinyl, piperidinyl and morpholinyl.

2. A compound according to claim 1 wherein Y is —(CHR$^{70}$)$_q$—.

3. A compound according to claim 2 wherein q is 1.

4. A compound according to claim 3 of the formula

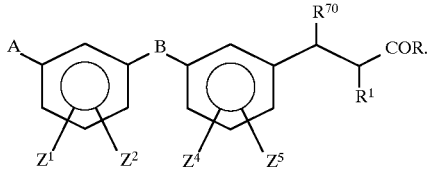

5. A compound according to claim 4 wherein the compound is selected from the group consisting of
β-[3-[[[[3-(aminoiminomethyl)amino]phenyl]carbonyl]amino]methyl]phenyl]-3,5-dichlorobenzenepropanoic acid;
3-[[[3-[(aminoiminomethyl)amino]phenyl]sulfonyl]amino]-β-phenylbenzenepropanoic acid;
3-[[[3-[(aminoiminomethyl)amino]phenyl]carbonyl]amino]-β-phenylbenzenepropanoic acid;
1,1-dimethylethyl 3-[[[3-[(aminocarbonyl)amino]phenyl]carbonyl]amino]-β-phenylbenzenepropanoate;
3-[[[3-[(aminocarbonyl)amino]phenyl]carbonyl]amino]-β-phenylbenzenepropanoic acid;
3-[[[4-[(aminoiminomethyl)amino]phenyl]sulfonyl]methylamino]-β-phenylbenzenepropanoic acid;
1,1-dimethylethyl 3-[[[3-[(aminocarbonyl)amino]phenyl]sulfonyl]amino]-β-phenylbenzenepropanoate;
3-[[[3-[(aminocarbonyl)amino]phenyl]sulfonyl]amino]-β-phenylbenzenepropanoic acid;
1,1-dimethylethyl 3-[[[3-[(aminothioxomethyl)amino]phenyl]sulfonyl]amino]-β-phenylbenzenepropanoate;
3-[[[3-[(aminothioxomethyl)amino]phenyl]sulfonyl]amino]-β-phenylbenzenepropanoic acid;
3-[[[3-[(aminoiminomethyl)amino]phenyl]methyl]amino]-β-phenylbenzenepropanoic acid;
1,1-dimethylethyl 3-[[[3-[[(phenylmethyl)amino]carbonyl]amino]phenyl]sulfonyl]amino]-β-phenylbenzenepropanoate;
3-[[[3-[[[(phenylmethyl)amino]carbonyl]amino]phenyl]sulfonyl]amino]-β-phenylbenzenepropanoic acid;
1,1-dimethylethyl 3-[[[3-[[(cyanoimino)(methylthio)methyl]amino]phenyl]sulfonyl]amino]-β-phenylbenzenepropanoate;
1,1-dimethylethyl 3-[[[3-[[amino(cyanoimino)methyl]amino]phenyl]sulfonyl]amino]-β-phenylpropanoate;
3-[[[3-[[amino[(aminocarbonyl)imino]methyl]amino]phenyl]sulfonyl]amino]-β-phenylbenzenepropanoic acid;
ethyl 3-[2-[3-[(aminoiminomethyl)amino]phenyl]ethyl]-β-phenylbenzenepropanoate;
3-[2-[3-[(aminoiminomethyl)amino]phenyl]ethyl]-β-phenylbenzenepropanoic acid;
ethyl 3-[[[[3-(aminoiminomethyl)phenyl]carbonyl]amino]methyl]benzenepropanoate;
ethyl 3-[[[[3-[aminoiminomethyl]phenyl]carbonyl]amino]methyl]benzenepropanoate;
3-[[[[3-(aminoiminomethyl)phenyl]carbonyl]amino]methyl]benzenepropanoic acid;
3-[[[[3-[(aminothioxomethyl)amino]phenyl]carbonyl]amino]methyl]benzenepropanoic acid;
3-[[[[3-[(aminothioxomethyl)amino]phenyl]carbonyl]amino]methyl]benzenepropanoic acid;
ethyl 3-[[[[3-[(aminocarbonyl)amino]phenyl]carbonyl]amino]methyl]benzenepropanoate;
3-[[[[3-[(aminocarbonyl)amino]phenyl]carbonyl]amino]methyl]benzenepropanoic acid;
ethyl 3-[[[[3-[[(phenylmethyl)amino]carbonyl]amino]phenyl]carbonyl]amino]methyl]benzenepropanoate;
3-[[[[3-[[(phenylmethyl)amino]carbonyl]amino]phenyl]carbonyl]amino]methyl]benzenepropanoic acid;
ethyl 3-[[[[3-[[[(phenylmethyl)amino]carbonyl]amino]phenyl]carbonyl]amino]methyl)-β-phenylbenzenepropanoate;
3-[[[[3-[[[(phenylmethyl)amino]carbonyl]amino]phenyl]carbonyl]amino]methyl]-β-phenylbenzenepropanoic acid;
ethyl 3-[[[[3-[(aminoiminomethyl)amino]phenyl]carbonyl]amino]methyl]benzenepropanoate;
3-[[[[3-[(aminoiminomethyl)amino]phenyl]carbonyl]amino]methyl]benzenepropanoic acid;
3-[[[3-[(aminoiminomethyl)amino]phenyl]carbonyl]amino]benzenepropanoic acid;
ethyl 3-[[[[3-[(aminoiminomethyl)amino]phenyl]carbonyl]amino]methyl]-β-phenylbenzenepropanoate;
3-[[[[3-[(aminoiminomethyl)amino]phenyl]carbonyl]amino]methyl]-β-phenylbenzenepropanoic acid;
1,1-dimethylethyl 3-[[[[3-[(aminoiminomethyl)amino]phenyl]carbonyl]amino]methyl]-β-methylbenzenepropanoate;
3-[[[[3-[(aminoiminomethyl)amino]phenyl]carbonyl]amino]methyl]-β-methylbenzenepropanoic acid;
ethyl 3-[[[[3-[(aminoiminomethyl)amino]phenyl]carbonyl]amino]methyl]-β-ethylbenzenepropanoate;
3-[[[[3-[(aminoiminomethyl)amino]phenyl]carbonyl]amino]methyl]-β-ethylbenzenepropanoic acid;
3-[[[[3-[(aminoiminomethyl)amino]phenyl]carbonyl]amino]methyl]-β-(1-methylethyl) benzenepropanoic acid;
N-acetyl-3-[[[[3-[(aminoiminomethyl)amino]phenyl]carbonyl]amino]methyl]phenylalanine;
3-[[[3-[(aminoiminomethyl)amino]phenyl]acetyl]amino]benzenepropanoic acid;
3-[[[[3-[(aminoiminomethyl)amino]phenyl]amino]carbonyl]amino]benzenepropanoic acid;
3-[[[[3-[(aminoiminomethyl)amino]phenyl]amino]carbonyl]amino]methyl]benzenepropanoic acid;
3-[[[3-[[(cyanoimino)(methylamino)methyl]amino]phenyl]carbonyl]amino]methyl]-β-phenylbenzenepropanoic acid;
3-[[[[3-[(aminoiminomethyl)amino]phenyl]carbonyl]amino]methyl]-βR-methylbenzenepropanoic acid;
3-[[[[3-[(aminoiminomethyl)amino]phenyl]carbonyl]amino]methyl]-βS-methylbenzenepropanoic acid;
(±) 3-[[[[3-((aminoiminomethyl)amino]-4-chlorophenyl]carbonyl]amino]methyl]-β-ethylbenzenepropanoic acid;
(±) 3-[[[[3-[(aminoiminomethyl)amino]-5-(trifluoromethyl)phenyl]carbonyl]amino]methyl]-β-ethylbenzenepropanoic acid;
(±) β-[3-[[[[3-[(aminoiminomethyl)amino]phenyl]carbonyl]amino]methyl]phenyl]-3,5-difluorobenzenepropanoic acid;
(±) β-[3-[[[[3-[(aminoiminomethyl)amino]-5-(trifluoromethyl)phenyl]carbonyl]amino]methyl]phenyl]-3,5-difluorobenzenepropanoic acid;
(±) 3,5-difluoro-β-[3-[[[[3-[(1,4,5,6-tetrahydropyrimidin-2-yl)amino]phenyl]carbonyl]amino]methyl]phenyl]benzenepropanoic acid;
(±) β-[3-[[[3-[(aminoiminomethyl)amino]phenyl]carbonyl]amino]methyl]phenyl]-2-methoxybenzenepropanoic acid;
(±) 3[[[3-[[amino(cyanoimino)methyl]amino]phenyl]carbonyl]amino]methyl]-β-methylbenzenepropanoic acid;
(±) 3[[[3-[[amino[(aminocarbonyl)imino]methyl]amino]phenyl]carbonyl]amino]methyl]-β-methylbenzenepropanoic acid;
(±) 3-[[[[3-[(4,5-dihydro-4-oxo-1H-imidazol-2-yl)amino]phenyl]carbonyl]amino]methyl]-β-methylbenzenepropanoic acid;

(±) 3-[[[[3-[(1H-benzimidazol-2-yl)amino]phenyl]carbonyl]amino]methyl]-β-methylbenzenepropanoic acid;
(±) 3-[[[[3-[(5-methoxy-1H-benzimidazol-2-yl)amino]phenyl]carbonyl]amino]methyl]-β-methylbenzenepropanoic acid;
3-[2-[3-[(4,5-dihydro-1H-imidazol-2-yl)amino]phenyl]-2-hydroxyethoxy]benzenepropanoic acid;
3-[2-[3-[(aminoiminomethyl)amino]phenyl]ethynyl]-β-phenylbenzenepropanoic acid;
3-[2E-[3-[(aminoiminomethyl)amino]phenyl]ethenyl]-β-phenylbenzenepropanoic acid;
3-[2Z-[3-[(aminoiminomethyl)amino]phenyl]ethenyl]-β-phenylbenzenepropanoic acid;
β-[3-[[[3-[(aminoiminomethyl)amino]phenyl]sulfonyl]amino]phenyl]-3,5-dichlorobenzenepropanoic acid;
β-[3-[[[3-[(aminoiminomethyl)amino]phenyl]sulfonyl]amino]phenyl]-3,5-difluorobenzenepropanoic acid;
β-[3-[[[3-[(aminoiminomethyl)amino]phenyl]sulfonyl]amino]phenyl]-4-fluorobenzenepropanoic acid;
β-[3-[[[3-[(aminoiminomethyl)amino]phenyl]sulfonyl]amino]phenyl]-3,4,5-trifluorobenzenepropanoic acid;
β-[3-[[[3-[(aminoiminomethyl)amino]phenyl]sulfonyl]amino]phenyl]perfluorobenzenepropanoic acid;
β-[3-[[[3-[(aminoiminomethyl)amino]phenyl]sulfonyl]amino]phenyl]-2,3,5,6-tetrafluorobenzenepropanoic acid;
3,5-difluoro-β-[3-[[[3-[[[(phenylmethyl)amino]carbonyl]amino]phenyl]sulfonyl]amino]phenyl]benzenepropanoic acid;
3,5-difluoro-β-[3-[[[3-[[[(phenylmethyl)imino]methyl]amino]phenyl]sulfonyl]amino]phenyl]benzenepropanoic acid;
3-[[3-[(aminoiminomethyl)amino]phenylthio]methyl]-β-phenylbenzenepropanoic acid;
3-[[[3-[(aminoiminomethyl)amino]phenyl]sulfinyl]methyl]-β-phenylbenzenepropanoic acid;
3-[[[3-[(aminoiminomethyl)amino]phenyl]sulfonyl]methyl]-β-phenylbenzenepropanoic acid;
β-3-[3-[[[3-[[amino[(aminocarbonyl)imino]methyl]amino]phenyl]sulfonyl]amino]phenyl]-3,5-dichlorobenzenepropanoic acid;
β-[3-[[[3-[[amino[(aminocarbonyl)imino]methyl]amino]phenyl]sulfonyl]amino]phenyl]-3,5-difluorobenzenepropanoic acid;
3-[[[3-[(aminoiminomethyl)amino]phenyl]sulfonyl]amino]-β-ethylbenzenepropanoic acid;
3-[[[3-[[amino[(aminocarbonyl)imino]methyl]amino]phenyl]sulfonyl]amino]-β-ethylbenzenepropanoic acid;
3-[[3-[(aminoiminomethyl)amino]phenyl]methoxy]-β-phenylbenzenepropanoic acid;
3,5-difluoro-β-[3-[[[3-[(1,4,5,6-tetrahydropyrimidin-2-yl)amino]phenyl]sulfonyl]amino]phenyl]benzenepropanoic acid;
β-[3-[[[3-[(4,5-dihydro-1H-imidazol-2-yl)amino]phenyl]sulfonyl]amino]phenyl]-3,5-difluorobenzenepropanoic acid;
3-[[3-[(4,5-dihydro-1H-imidazol-2-yl)amino]phenyl]methoxy]-β-phenylbenzenepropanoic acid; and
sodium β-[3-[[[3-[(aminoiminomethyl)amino]-phenyl]sulfonyl]amino]phenyl]-2-hydroxybenzenepropanoate.

6. A compound according to claim 1 wherein Y is (CHR$^{70}$)$_q$ and q is 0 or Y is —O—.

7. A compound according to claim 6 wherein the compound is selected from the group consisting of
ethyl 3-[[[3-[amino(hydroxyimino)methyl]phenyl]carbonyl]amino]benzeneacetate;
3-[[[3-(aminoiminomethyl)phenyl]carbonyl]amino]benzeneacetic acid;
3-[2-[[[3-[(aminoiminomethyl)amino]phenyl]carbonyl]amino]ethyl]benzeneacetic acid;
methyl 3-[[[[3-[(aminoiminomethyl)amino]phenyl]carbonyl]amino]methyl]benzeneacetate;
ethyl 3-[[[3-(aminoiminomethyl)phenyl]carbonyl]amino]benzeneacetate;
3-[[[[3-[(aminoiminomethyl)amino]phenyl]carbonyl]amino]methyl]benzeneacetic acid;
3-[[[3-[(aminoiminomethyl)amino]phenyl]carbonyl]amino]benzeneacetic acid;
2-[3-[3-[3-[(4,5-dihydro-1H-imidazol-2-yl)amino]phenyl]-1-oxo-2-propenyl]phenoxy]acetic acid;
2-[3-[3-[3-[(aminoiminomethyl)amino]phenyl]-1-oxopropenyl]phenoxy]acetic acid; and
[3-[[[[3-[(aminoiminomethyl)amino]phenyl]amino]carbonyl]amino]phenoxy]acetic acid.

8. A compound according to claim 1 selected from the group consisting of
3-[(aminoiminomethyl)amino]-N-[3-(3,4-dihydro-2-oxo-2H-benzopyran-4-yl)phenyl]benzenesulfonamide; and
3-[(4,5-dihydro-1H-imidazol-2-yl)amino]-N-[3-(3,4-dihydro-2-oxo-2H-benzopyran-4-yl)phenyl]benzenesulfonamide.

9. A pharmaceutical composition comprising a therapeutically effective amount of a compound of the formula

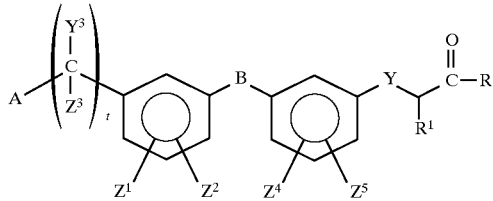

or a pharmaceutically acceptable salt thereof, wherein
A is

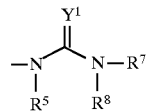

wherein Y$^1$ is selected from the group consisting of N—R$^2$, O, and S;
R$^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy, oxo and phenyl; or $R^2$ taken together with $R^7$ forms a 5 membered heteroaromatic ring; or $R^2$ taken together with $R^7$ forms a 5 membered heteroaromatic ring fused with a phenyl group optionally substituted with one or more substituent selected from the group consisting of alkoxy and alkoxycarbonyl;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —$SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein $R^{10}$ is defined above; or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl; or A is

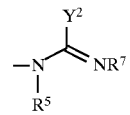

wherein $Y^2$ is selected from the group consisting of hydrogen; alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; —S—$R^9$ and —O—$R^9$ wherein $R^9$ is selected from the group consisting of H; alkyl; aralkyl; aryl; alkenyl; and alkynyl; or $R^9$ taken together with $R^7$ forms a 4–12 membered mononitrogen containing sulfur or oxygen containing heterocyclic ring; and $R^5$ and $R^7$ are as defined above; or $Y^2$ (when $Y^2$ is carbon) taken together with $R^7$ forms a 4–12 membered mononitrogen containing ring optionally substituted with alkyl, aryl or hydroxy; or A is selected from the group consisting of

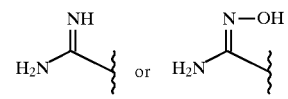

$Z^1$, $Z^2$, $Z^4$ and $Z^5$ are independently selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles; and A, wherein A is defined above;

B is selected from the group consisting of

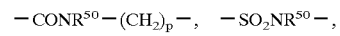

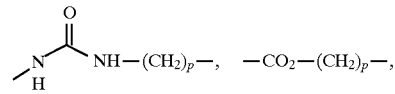

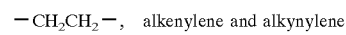

optionally substituted by oxo;

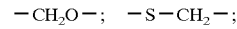

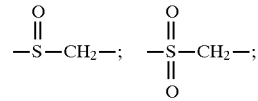

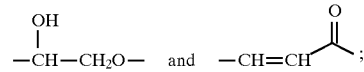

wherein p is an integer selected from the group consisting of 0, 1 and 2; wherein n is an integer selected from the group consisting of 0, 1, 2 and 3; $R^{50}$ is selected from the group consisting of H and alkyl;

Y is selected from the group consisting of

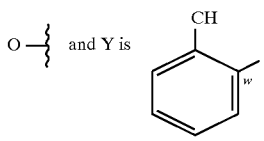

wherein q is an integer selected from the group consisting of 0 and 1; $R^{70}$ is selected from the group consisting of H, alkyl, aryl and aryl substituted with one or more substituent selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles;

t is an integer 0, 1 or 2;

R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; aryl; arylalkyl; sugars; steroids and in the case of the free acid, all pharmaceutically acceptable salts thereof; or X—$R^3$ is

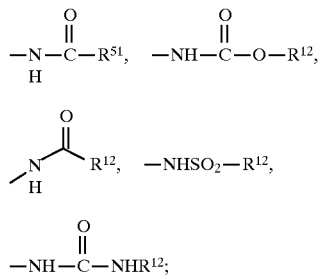

wherein the X—$R^3$ group is attached to the phenyl of the Y group at the para position to form a lactone;

$Y^3$ and $Z^3$ are independently selected from the group consisting of H, alkyl, aryl, cycloalkyl and aralkyl;

$R^1$ is selected from the group consisting of hydrogen; alkyl; aryl;

$$-\underset{H}{N}-\overset{O}{\underset{\|}{C}}-R^{51}, \quad -NH-\overset{O}{\underset{\|}{C}}-O-R^{12},$$

$$\underset{H}{\overset{}{N}}\overset{O}{\underset{\|}{C}}R^{12}, \quad -NHSO_2-R^{12},$$

$$-NH-\overset{O}{\underset{\|}{C}}-NHR^{12};$$

$R^{12}$ is selected from the group consisting of H, alkyl, cycloalkyl, aralkyl and aryl;

$R^{51}$ is selected from the group consisting of N-substituted pyrrolidinyl, piperidinyl and morpholinyl; and a pharmaceutically acceptable carrier.

10. A pharmaceutical composition according to claim 9 wherein Y is $(CHR^{70})_q$ or —O—.

11. A pharmaceutical composition according to claim 10 wherein when Y is $(CHR^{70})_q$, q is 0 or 1.

12. A pharmaceutical composition according to claim 11 of the formula

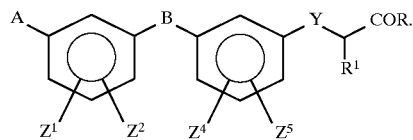

13. A pharmaceutical composition according to claim 12 wherein the compound is selected from the group consisting of β-[3-[[[3-(aminoiminomethyl)amino]phenyl]carbonyl]amino]methyl]phenyl]-3,5-dichlorobenzenepropanoic acid;

3-[[[3-[(aminoiminomethyl)amino]phenyl]sulfonyl]amino]-β-phenylbenzenepropanoic acid;

3-[[[3-[(aminoiminomethyl)amino]phenyl]carbonyl]amino]-β-phenylbenzenepropanoic acid;

1,1-dimethylethyl 3-[[[3-[(aminocarbonyl)amino]phenyl]carbonyl]amino]-β-phenylbenzenepropanoate;

3-[[[3-[(aminocarbonyl)amino]phenyl]carbonyl]amino]-β-phenylbenzenepropanoic acid;

3-[[[4-[(aminoiminomethyl)amino]phenyl]sulfonyl]methylamino]-β-phenylbenzenepropanoic acid;

1,1-dimethylethyl 3-[[[3-[(aminocarbonyl)amino]phenyl]sulfonyl]amino]-β-phenylbenzenepropanoate;

3-[[[3-[(aminocarbonyl)amino]phenyl]sulfonyl]amino]-β-phenylbenzenepropanoic acid;

1,1-dimethylethyl 3-[[[3-[(aminothioxomethyl)amino]phenyl]sulfonyl]amino]-β-phenylbenzenepropanoate;

3-[[[3-[(aminothioxomethyl)amino]phenyl]sulfonyl]amino]-β-phenylbenzenepropanoic acid;

3-[[[3-[(aminoiminomethyl)amino]phenyl]methyl]amino]-β-phenylbenzenepropanoic acid;

1,1-dimethylethyl 3-[[[3-[[[(phenylmethyl)amino]carbonyl]amino]phenyl]sulfonyl]amino]-β-phenylbenzenepropanoate;

3-[[[3-[[[(phenylmethyl)amino]carbonyl]amino]phenyl]sulfonyl]amino]-β-phenylbenzenepropanoic acid;

1,1-dimethylethyl 3-[[[3-[[(cyanoimino)(methylthio)methyl]amino]phenyl]sulfonyl]amino]-β-phenylbenzenepropanoate;

1,1-dimethylethyl 3-[[[3-[[amino(cyanoimino)methyl]amino]phenyl]sulfonyl]amino]-β-phenylpropanoate;

3-[[[3-[[amino[(aminocarbonyl)imino]methyl]amino]phenyl]sulfonyl]amino]-β-phenylbenzenepropanoic acid;

ethyl 3-[2-[3-[(aminoiminomethyl)amino]phenyl]ethyl]-β-phenylbenzenepropanoate;

3-[2-[3-[(aminoiminomethyl)amino]phenyl]ethyl]-β-phenylbenzenepropanoic acid;

ethyl 3-[[[[3-(aminoiminomethyl)phenyl]carbonyl]amino]methyl)benzenepropanoate;

ethyl 3-[[[[3-[aminoiminomethyl]phenyl]carbonyl]amino]methyl]benzenepropanoate;

3-[[[[3-(aminoiminomethyl)phenyl]carbonyl]amino]methyl]benzenepropanoic acid;

3-[[[[3-[(aminothioxomethyl)amino]phenyl]carbonyl]amino]methyl]benzenepropanoic acid;

3-[[[[3-[(aminothioxomethyl)amino]phenyl]carbonyl]amino]methyl]benzenepropanoic acid;

ethyl 3-[[[[3-[(aminocarbonyl)amino]phenyl]carbonyl]amino]methyl]benzenepropanoate;

3-[[[[3-[(aminocarbonyl)amino)phenyl]carbonyl]amino]methyl]benzenepropanoic acid;

ethyl 3-[[[[3-[[[(phenylmethyl)amino]carbonyl]amino]phenyl]carbonyl]amino]methyl]benzenepropanoate;

3-[[[[3-[[[(phenylmethyl)amino]carbonyl]amino]phenyl]carbonyl]amino]methyl]benzenepropanoic acid;

ethyl 3-[[[[3-[[[(phenylmethyl)amino]carbonyl]amino]phenyl]carbonyl]amino]methyl]-β-phenylbenzenepropanoate;
3-[[[[3-[[[(phenylmethyl)amino]carbonyl]amino]phenyl]carbonyl]amino]methyl]-β-phenylbenzenepropanoic acid;
ethyl 3-[[[[3-[(aminoiminomethyl)amino]phenyl]carbonyl]amino]methyl]benzenepropanoate;
3-[[[[3-[(aminoiminomethyl)amino]phenyl]carbonyl]amino]methyl]benzenepropanoic acid;
3-[[[3-[(aminoiminomethyl)amino]phenyl]carbonyl]amino benzenepropanoic acid;
ethyl 3-[[[[3-[(aminoiminomethyl)amino]phenyl]carbonyl]amino]methyl]-β-phenylbenzenepropanoate;
3-[[[[3-[(aminoiminomethyl)amino]phenyl]carbonyl]amino]methyl]-β-phenylbenzenepropanoic acid;
1,1-dimethylethyl 3-[[[[3-[(aminoiminomethyl)amino]phenyl]carbonyl]amino]methyl]-β-methylbenzenepropanoate;
3-[[[[3-[(aminoiminomethyl)amino]phenyl]carbonyl]amino]methyl]-β-methylbenzenepropanoic acid;
ethyl 3-[[[[3-[(aminoiminomethyl)amino]phenyl]carbonyl]amino]methyl]-β-ethylbenzenepropanoate;
3-[[[[3-[(aminoiminomethyl)amino]phenyl]carbonyl]amino]methyl]-β-ethylbenzenepropanoic acid;
3-[[[[3-[(aminoiminomethyl)amino]phenyl]carbonyl]amino]methyl]-β-(1-methylethyl) benzenepropanoic acid;
N-acetyl-3-[[[[3-[(aminoiminomethyl)amino]phenyl]carbonyl]amino]methyl]phenylalanine;
3-[[[3-[(aminoiminomethyl)amino]phenyl]acetyl]amino benzenepropanoic acid;
3-[[[[3-[(aminoiminomethyl)amino]phenyl]amino]carbonyl]amino]benzenepropanoic acid;
3-[[[[[3-[(aminoiminomethyl)amino]phenyl]amino]carbonyl]amino]methyl]benzenepropanoic acid;
3-[[[[3-[[(cyanoimino)(methylamino)methyl]amino]phenyl]carbonyl]amino]methyl]-β-phenylbenzenepropanoic acid;
3-[[[[3-[(aminoiminomethyl)amino]phenyl]carbonyl]amino]methyl]-βR-methylbenzenepropanoic acid;
3-[[[[3-[(aminoiminomethyl)amino]phenyl]carbonyl]amino]methyl]-βS-methylbenzenepropanoic acid;
(±) 3-[[[[3-[(aminoiminomethyl)amino]-4-chlorophenyl]carbonyl]amino]methyl]-β-ethylbenzenepropanoic acid;
(±) 3-[[[[3-[(aminoiminomethyl)amino]-5-(trifluoromethyl)phenyl]carbonyl]amino]methyl]-β-ethylbenzenepropanoic acid;
(±) β-[3-[[[[3-[(aminoiminomethyl)amino]phenyl]carbonyl]amino]methyl]phenyl]-3,5-difluorobenzenepropanoic acid;
(±) β-[3-[[[[3-[(aminoiminomethyl)amino]-5-(trifluoromethyl)phenyl]carbonyl]amino]methyl]phenyl]-3,5-difluorobenzenepropanoic acid;
(±) 3,5-difluoro-β-[3-[[[[3-[(1,4,5,6-tetrahydropyrimidin-2-yl)amino]phenyl]carbonyl]amino]methyl]phenyl]benzenepropanoic acid;
(±) β-[3-[[[[3-[(aminoiminomethyl)amino]phenyl]carbonyl]amino]methyl]phenyl]-2-methoxybenzenepropanoic acid;
(±) 3[[[[3-[[amino(cyanoimino)methyl]amino]phenyl]carbonyl]amino]methyl]-β-methylbenzenepropanoic acid;
(±) 3[[[[3-[[amino[(aminocarbonyl)imino]methyl]amino]phenyl]carbonyl]amino]methyl]-β-methylbenzenepropanoic acid;
(±) 3-[[[[3-[(4,5-dihydro-4-oxo-1H-imidazol-2-yl)amino]phenyl]carbonyl]amino]methyl]-β-methylbenzenepropanoic acid;
(±) 3-[[[[3-[(1H-benzimidazol-2-yl)amino]phenyl]carbonyl]amino]methyl]-β-methylbenzenepropanoic acid;
(±) 3-[[[[3-[(5-methoxy-1H-benzimidazol-2-yl)amino]phenyl]carbonyl]amino]methyl]-β-methylbenzenepropanoic acid;
3-[2-[3-[(4,5-dihydro-1H-imidazol-2-yl)amino]phenyl]-2-hydroxyethoxy]benzenepropanoic acid;
3-[2-[3-[(aminoiminomethyl)amino]phenyl]ethynyl]-β-phenylbenzenepropanoic acid;
3-[2E-[3-[(aminoiminomethyl)amino]phenyl]ethenyl]-β-phenylbenzenepropanoic acid;
3-[2Z-[3-[(aminoiminomethyl)amino]phenyl]ethenyl]-β-phenylbenzenepropanoic acid;
β-[3-[[[3-[(aminoiminomethyl)amino]phenyl]sulfonyl]amino]phenyl]-3,5-dichlorobenzenepropanoic acid;
β-[3-[[[3-[(aminoiminomethyl)amino]phenyl]sulfonyl]amino]phenyl]-3,5-difluorobenzenepropanoic acid;
β-[3-[[[3-[(aminoiminomethyl)amino]phenyl]sulfonyl]amino]phenyl]-4-fluorobenzenepropanoic acid;
β-[3-[[[3-[(aminoiminomethyl)amino]phenyl]sulfonyl]amino]phenyl]-3,4,5-trifluorobenzenepropanoic acid;
β-[3-[[[3-[(aminoiminomethyl)amino]phenyl]sulfonyl]amino]phenyl]perfluorobenzenepropanoic acid;
β-[3-[[[3-[(aminoiminomethyl)amino]phenyl]sulfonyl]amino]phenyl]-2,3,5,6-tetrafluorobenzenepropanoic acid;
3,5-difluoro-β-[3-[[[3-[[[(phenylmethyl)amino]carbonyl]amino]phenyl]sulfonyl]amino]phenyl]benzenepropanoic acid;
3,5-difluoro-β-[3-[[[3-[[[(phenylmethyl)imino]methyl]amino]phenyl]sulfonyl]amino]phenyl]benzenepropanoic acid;
3-[[3-[(aminoiminomethyl)aminophenylthio]methyl]-β-phenylbenzenepropanoic acid;
3-[[[3-[(aminoiminomethyl)amino]phenyl]sulfinyl]methyl]-β-phenylbenzenepropanoic acid;
3-[[[3-[(aminoiminomethyl)amino]phenyl]sulfonyl]methyl)-β-phenylbenzenepropanoic acid;
β-[3-[[[3-[[amino[(aminocarbonyl)imino]methyl]amino]phenyl]sulfonyl]amino]phenyl]-3,5-dichlorobenzenepropanoic acid;
β-[3-[[[3-[[amino[(aminocarbonyl)imino]methyl]amino]phenyl]sulfonyl]amino]phenyl]-3,5-difluorobenzenepropanoic acid;
3-[[[3-[(aminoiminomethyl)amino]phenyl]sulfonyl]amino]-β-ethylbenzenepropanoic acid;
3-[[[3-[[amino[(aminocarbonyl)imino]methyl]amino]phenyl]sulfonyl]amino]-β-ethylbenzenepropanoic acid;
3-[[3-[(aminoiminomethyl)amino]phenyl]methoxy]-β-phenylbenzenepropanoic acid;
3,5-difluoro-β-[3-[[[3-[(1,4,5,6-tetrahydropyrimidin-2-yl)amino]phenyl]sulfonyl]amino]phenyl]benzenepropanoic acid;
β-[3-[[[3-[(4,5-dihydro-1H-imidazol-2-yl)amino]phenyl]sulfonyl]amino]phenyl]-3,5-difluorobenzenepropanoic acid;
3-[[3-[(4,5-dihydro-1H-imidazol-2-yl)amino]phenyl]methoxy]-β-phenylbenzenepropanoic acid;
sodium β-[3-[[[3-[(aminoiminomethyl)amino]phenyl]sulfonyl]amino]phenyl]-2-hydroxybenzenepropanoate;
ethyl 3-[[[3-[amino(hydroxyimino)methyl]phenyl]carbonyl]amino]benzeneacetate;
3-[[[3-(aminoiminomethyl)phenyl]carbonyl]amino]benzeneacetic acid;
3-[2-[[[3-[(aminoiminomethyl)amino]phenyl]carbonyl]amino]ethyl]benzeneacetic acid;
methyl 3-[[[[3-[(aminoiminomethyl)amino]phenyl]carbonyl]amino]methyl]benzeneacetate;

ethyl 3-[[[3-(aminoiminomethyl)phenyl]carbonyl]amino]
   benzeneacetate;
3-[[[[3-[(aminoiminomethyl)amino]phenyl]carbonyl]
   amino]methyl]benzeneacetic acid;
3-[[[3-[(aminoiminomethyl)amino]phenyl]carbonyl]amino]
   benzeneacetic acid;
2-[3-[3-[3-[(4,5-dihydro-1H-imidazol-2-yl)amino]phenyl]-
   1-oxo-2-propenyl]phenoxy]acetic acid;
2-[3-[3-[3-[(aminoiminomethyl)amino]phenyl]-1-
   oxopropenyl]phenoxy]acetic acid; and
[3-[[[[3-[(aminoiminomethyl)amino]phenyl]amino]
   carbonyl]amino]phenoxy]acetic acid.

14. A pharmaceutical composition according to claim 9 wherein the compound is selected from the group consisting of 3-[(aminoiminomethyl)amino]-N-[3-(3,4-dihydro-2-oxo-
   2H-benzopyran-4-yl)phenyl]benzenesulfonamide; and
3-[(4,5-dihydro-1H-imidazol-2-yl)amino]-N-[3-(3,4-
   dihydro-2-oxo-2H-benzopyran-4-yl)phenyl]
   benzenesulfonamide.

15. A method for treating conditions mediated by the $\alpha_v\beta_3$ integrin in a mammal in need of such treatment comprising administering an effective $\alpha_v\beta_3$ inhibiting amount of a compound of the formula

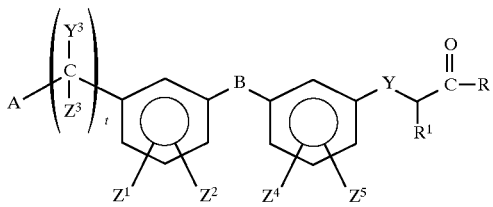

or a pharmaceutically acceptable salt thereof, wherein
A is

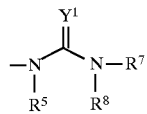

wherein $Y^1$ yl is selected from the group consisting of
   $N—R^2$, O, and S;
$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or
$R^2$ taken together with $R^7$ forms a 4–12 membered dinitrogen containing heterocycle optionally substituted with one or more substituent selected from the group consisting of lower alkyl, hydroxy, oxo and phenyl; or $R^2$ taken together with $R^7$ forms a 5 membered heteroaromatic ring; or $R^2$ taken together with $R^7$ forms a 5 membered heteroaromatic ring fused with a phenyl group optionally substituted with one or more substituent selected from the group consisting of alkoxy and alkoxycarbonyl;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —$SO_2R^{10}$ wherein $R_{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein $R^{10}$ is defined above; or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl; or A is

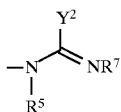

wherein $Y^2$ is selected from the group consisting of hydrogen; alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; —S—$R^9$ and —O—$R^9$ wherein $R^9$ is selected from the group consisting of H; alkyl; aralkyl; aryl; alkenyl; and alkynyl; or $R^5$ taken together with $R^7$ forms a 4–12 membered mononitrogen containing sulfur or oxygen containing heterocyclic ring; and $R^5$ and $R^7$ are as defined above; or $Y^2$ (when $Y^2$ is carbon) taken together with $R^7$ forms a 4–12 membered mononitrogen containing ring optionally substituted with alkyl, aryl or hydroxy; or A is selected from the group consisting of

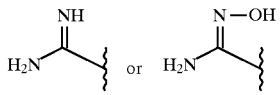

$Z^1$, $Z^2$, $Z^4$ and $Z^5$ are independently selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles; and A, wherein A is defined above;

B is selected from the group consisting of

—CONR$^{50}$—(CH$_2$)$_p$—, —SO$_2$NR$^{50}$—,

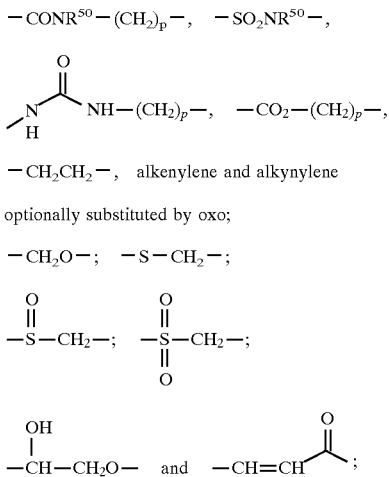

—CH$_2$CH$_2$—, alkenylene and alkynylene optionally substituted by oxo;

—CH$_2$O—; —S—CH$_2$—;

wherein p is an integer selected from the group consisting of 0, 1 and 2; wherein n is an integer selected from the group consisting of 0, 1, 2 and 3; $R^{50}$ is selected from the group consisting of H and alkyl;

Y is selected from the group consisting of

—(CHR$^{70}$)$_q$— and —O—;

wherein q is an integer selected from the group consisting of 0 and 1; $R^{70}$ is selected from the group consisting of H, alkyl, aryl and aryl substituted with one or more substituent selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles;

t is an integer 0, 1 or 2;

R is X—$R^3$ wherein X is selected from the group consisting of O, S and NR$^4$, wherein $R^3$ and $R^4$ are independently selected from the group consisting of hydrogen; alkyl; alkenyl; alkynyl; haloalkyl; aryl; arylalkyl; sugars; steroids and in the case of the free acid, all pharmaceutically acceptable salts thereof; or X—$R^3$ is

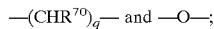

wherein the X—$R^3$ group is attached to the phenyl of the Y group at the para position to form a lactone;

$Y^3$ and $Z^3$ are independently selected from the group consisting of H, alkyl, aryl, cycloalkyl and aralkyl;

$R^1$ is selected from the group consisting of hydrogen; alkyl; aryl;

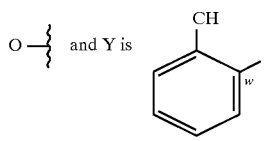

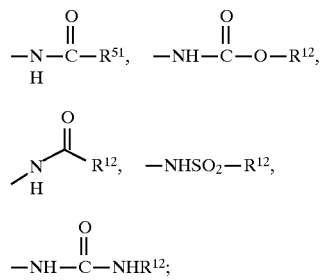

$R^{12}$ is selected from the group consisting of H, alkyl, cycloalkyl, aralkyl and aryl; and $R^{51}$ is selected from the group consisting of N-substituted pyrrolidinyl, piperidinyl and morpholinyl.

16. A method according to claim 15 wherein the compound is selected from the group consisting of β-[3-[[[3-(aminoiminomethyl)amino]phenyl]carbonyl]amino]methyl]phenyl]-3,5-dichlorobenzenepropanoic acid;

3-[[[3-[(aminoiminomethyl)amino]phenyl]sulfonyl]amino]-β-phenylbenzenepropanoic acid;

3-[[[3-[(aminoiminomethyl)amino]phenyl]carbonyl]amino]-β-phenylbenzenepropanoic acid;

1,1-dimethylethyl 3-[[[3-[(aminocarbonyl)amino]phenyl]carbonyl]amino]-β-phenylbenzenepropanoate;

3-[[[3-[(aminocarbonyl)amino]phenyl]carbonyl]amino]-β-phenylbenzenepropanoic acid;

3-[[[4-[(aminoiminomethyl)amino]phenyl]sulfonyl]
methylamino]-β-phenylbenzenepropanoic acid;
1,1-dimethylethyl 3-[[[3-[(aminocarbonyl)amino]phenyl]
sulfonyl]amino]-β-phenylbenzenepropanoate;
3-[[[3-[(aminocarbonyl)amino]phenyl]sulfonyl]amino]-β-
phenylbenzenepropanoic acid;
1,1-dimethylethyl 3-[[[3-[(aminothioxomethyl)amino]
phenyl]sulfonyl]amino]-β-phenylbenzenepropanoate;
3-[[[3-[(aminothioxomethyl)amino]phenyl]sulfonyl]amino]
-β-phenylbenzenepropanoic acid;
3-[[[3-[(aminoiminomethyl)amino]phenyl]methyl]amino]-
β-phenylbenzenepropanoic acid;
1,1-dimethylethyl 3-[[[3-[[[(phenylmethyl)amino]carbonyl]
amino]phenyl]sulfonyl]amino]-β-
phenylbenzenepropanoate;
3-[[[3-[[[(phenylmethyl)amino]carbonyl]amino]phenyl]
sulfonyl]amino]-β-phenylbenzenepropanoic acid;
1,1-dimethylethyl 3-[[[3-[[(cyanoimino)(methylthio)
methyl]amino]phenyl]sulfonyl]amino]-β-
phenylbenzenepropanoate;
1,1-dimethylethyl 3-[[[3-[[amino(cyanoimino)methyl]
amino]phenyl]sulfonyl]amino]-β-phenylpropanoate;
3-[[[3-[[amino[(aminocarbonyl)imino]methyl]amino]
phenyl]sulfonyl]amino]-β-phenylbenzenepropanoic acid;
ethyl 3-[2-[3-[(aminoiminomethyl)amino]phenyl]ethyl]-β-
phenylbenzenepropanoate;
3-[2-[3-[(aminoiminomethyl)amino]phenyl]ethyl]-β-
phenylbenzenepropanoic acid;
ethyl 3-[[[[3-(aminoiminomethyl)phenyl]carbonyl]amino]
methyl]benzenepropanoate;
ethyl 3-[[[[3-[aminoiminomethyl)phenyl]amino]carbonyl]amino]
methyl]benzenepropanoate;
3-[[[[3-(aminoiminomethyl)phenyl]carbonyl]amino]
methyl]benzenepropanoic acid;
3-[[[[3-[(aminothioxomethyl)amino]phenyl]carbonyl]
amino]methyl]benzenepropanoic acid;
3-[[[[3-[(aminothioxomethyl)amino]phenyl]carbonyl]
amino]methyl]benzenepropanoic acid;
ethyl 3-[[[[3-[(aminocarbonyl)amino]phenyl]carbonyl]
amino]methyl]benzenepropanoate;
3-[[[[3-[(aminocarbonyl)amino]phenyl]carbonyl]amino]
methyl]benzenepropanoic acid;
ethyl 3-[[[[3-[[[(phenylmethyl)amino]carbonyl]amino]
phenyl]carbonyl]amino]methyl]benzenepropanoate;
3-[[[[3-[[[(phenylmethyl)amino]carbonyl]amino]phenyl]
carbonyl]amino]methyl]benzenepropanoic acid;
ethyl 3-[[[[3-[[[(phenylmethyl)amino]carbonyl]amino]
phenyl]carbonyl]amino]methyl]-β-
phenylbenzenepropanoate;
3-[[[[3-[[[(phenylmethyl)amino]carbonyl]amino]phenyl]
carbonyl]amino]methyl]-β-phenylbenzenepropanoic
acid;
ethyl 3-[[[[3-[(aminoiminomethyl)amino]phenyl]carbonyl]
amino]methyl]benzenepropanoate;
3-[[[[3-[(aminoiminomethyl)amino]phenyl]carbonyl]
amino]methyl]benzenepropanoic acid;
3-[[[3-[(aminoiminomethyl)amino]phenyl]carbonyl]amino]
benzenepropanoic acid;
ethyl 3-[[[[3-[(aminoiminomethyl)amino]phenyl]carbonyl]
amino]methyl]-β-phenylbenzenepropanoate;
3-[[[[3-[(aminoiminomethyl)amino]phenyl]carbonyl]
amino]methyl]-β-phenylbenzenepropanoic acid;
1,1-dimethylethyl 3-[[[[3-[(aminoiminomethyl)amino]
phenyl]carbonyl)amino]methyl]-β-methyl benzenepropanoate;
3-[[[[3-[(aminoiminomethyl)amino]phenyl]carbonyl]
amino]methyl]-β-methylbenzenepropanoic acid;

ethyl 3-[[[[3-[(aminoiminomethyl)amino]phenyl]carbonyl]
amino]methyl]-β-ethylbenzenepropanoate;
3-[[[(3-[(aminoiminomethyl)amino]phenyl]carbonyl]
amino]methyl]-β-ethylbenzenepropanoic acid;
3-[[[[3-[(aminoiminomethyl)amino]phenyl]carbonyl)
amino]methyl)-β-(1-methylethyl) benzenepropanoic
acid;
N-acetyl-3-[[[[3-[(aminoiminomethyl)amino]phenyl]
carbonyl]amino]methyl]phenylalanine;
3-[[[3-[(aminoiminomethyl)amino]phenyl]acetyl]amino]
benzenepropanoic acid;
3-[[[[3-[(aminoiminomethyl)amino]phenyl]amino]
carbonyl]amino]benzenepropanoic acid;
3-[[[[[3-[(aminoiminomethyl)amino]phenyl]amino]
carbonyl]amino]methyl]benzenepropanoic acid;
3-[[[3-[[(cyanoimino)(methylamino)methyl]amino]phenyl]
carbonyl]amino]methyl]-β-phenylbenzenepropanoic
acid;
3-[[[[3-[(aminoiminomethyl)amino]phenyl]carbonyl]
amino]methyl]-βR-methylbenzenepropanoic acid;
3-[[[[3-[(aminoiminomethyl)amino]phenyl]carbonyl]
amino]methyl]-βS-methylbenzenepropanoic acid;
(±) 3-[[[[3-[(aminoiminomethyl)amino]-4-chlorophenyl]
carbonyl]amino]methyl]-β-ethylbenzenepropanoic acid;
(±) 3-[[[[3-[(aminoiminomethyl)amino]-5-(trifluoromethyl)
phenyl]carbonyl]amino]methyl]-β-
ethylbenzenepropanoic acid;
(±) β-[3-[[[[3-[(aminoiminomethyl)amino]phenyl]carbonyl]
amino]methyl]phenyl]-3,5-difluorobenzenepropanoic
acid;
(±) β-[3-[[[[3-[(aminoiminomethyl)amino]-5-
(trifluoromethyl)phenyl]carbonyl]amino]methyl]phenyl]-
3,5-difluorobenzenepropanoic acid;
(±) 3,5-difluoro-β-[3-[[[[3-[(1,4,5,6-tetrahydropyrimidin-2-
yl)amino]phenyl]carbonyl]amino]methyl]phenyl]
benzenepropanoic acid;
(±) β-[3-[[[[3-[(aminoiminomethyl)amino]phenyl]carbonyl]
amino]methyl]phenyl]-2-methoxybenzenepropanoic
acid;
(±) 3[[[[3-[[amino(cyanoimino)methyl]amino]phenyl]
carbonyl]amino]methyl]-β-methylbenzenepropanoic
acid;
(±) 3[[[[3-[[amino[(aminocarbonyl)imino]methyl]amino]
phenyl]carbonyl]amino]methyl]-β-
methylbenzenepropanoic acid;
(±) 3-[[[(3-[(4,5-dihydro-4-oxo-1H-imidazol-2-yl)amino]
phenyl]carbonyl]amino]methyl]-β-
methylbenzenepropanoic acid;
(±) 3-[[((3-[(1H-benzimidazol-2-yl)amino]phenyl]
carbonyl]amino]methyl]-β-methylbenzenepropanoic
acid;
(±) 3-[[[[3-[(5-methoxy-1H-benzimidazol-2-yl)amino]
phenyl]carbonyl]amino]methyl]-β-
methylbenzenepropanoic acid;
3-[2-[3-[(4,5-dihydro-1H-imidazol-2-yl)amino]phenyl]-2-
hydroxyethoxy]benzenepropanoic acid;
3-[2-[3-[(aminoiminomethyl)amino]phenyl]ethynyl]-β-
phenylbenzenepropanoic acid;
3-[2E-[3-[(aminoiminomethyl)amino]phenyl]ethenyl]-β-
phenylbenzenepropanoic acid;
3-[2Z-[3-[(aminoiminomethyl)amino]phenyl]ethenyl]-β-
phenylbenzenepropanoic acid;
β-[3-[[[3-[(aminoiminomethyl)amino]phenyl]sulfonyl]
amino]phenyl]-3,5-dichlorobenzenepropanoic acid;
β-[3-[[[3-[(aminoiminomethyl)amino]phenyl]sulfonyl]
amino]phenyl]-3,5-difluorobenzenepropanoic acid;
β-[3-[[[3-[(aminoiminomethyl)amino]phenyl]sulfonyl]
amino]phenyl]-4-fluorobenzenepropanoic acid;

β-[3-[[[3-[(aminoiminomethyl)amino]phenyl]sulfonyl]amino]phenyl]-3,4,5-trifluorobenzenepropanoic acid;
β-[(3-[[[3-[(aminoiminomethyl)amino]phenyl]sulfonyl]amino]phenyl]perfluorobenzenepropanoic acid;
β-[3-[[[3-[(aminoiminomethyl)amino]phenyl]sulfonyl]amino]phenyl]-2,3,5,6-tetrafluorobenzenepropanoic acid;
3,5-difluoro-β-[3-[[[3-[[[(phenylmethyl)amino]carbonyl]amino]phenyl]sulfonyl]amino]phenyl]benzenepropanoic acid;
3,5-difluoro-β-[3-[[[3-[[[(phenylmethyl)imino]methyl]amino]phenyl]sulfonyl]amino]phenyl]benzenepropanoic acid;
3-[[3-[(aminoiminomethyl)amino]phenylthio]methyl]-β-phenylbenzenepropanoic acid;
3-[[[3-[(aminoiminomethyl)amino]phenyl]sulfinyl]methyl]-β-phenylbenzenepropanoic acid;
3-[[[3-[(aminoiminomethyl)amino]phenyl]sulfonyl]methyl]-β-phenylbenzenepropanoic acid;
β-[3-[[[3-[[amino[(aminocarbonyl)imino]methyl]amino]phenyl]sulfonyl]amino]phenyl]-3,5-dichlorobenzenepropanoic acid;
β-[3-[[[3-[[amino[(aminocarbonyl)imino]methyl]amino]phenyl]sulfonyl]amino]phenyl]-3,5-difluorobenzenepropanoic acid;
3-[[[3-[(aminoiminomethyl)amino]phenyl]sulfonyl]amino]-β-ethylbenzenepropanoic acid;
3-[[[3-[[amino[(aminocarbonyl)imino]methyl]amino]phenyl]sulfonyl]amino]-β-ethylbenzenepropanoic acid;
3-[[3-[(aminoiminomethyl)amino]phenyl]methoxy]-β-phenylbenzenepropanoic acid;
3,5-difluoro-β-[3-[[[3-[(1,4,5,6-tetrahydropyrimidin-2-yl)amino]phenyl]sulfonyl]amino]phenyl]benzenepropanoic acid;
β-[3-[[[3-[(4,5-dihydro-1H-imidazol-2-yl)amino]phenyl]sulfonyl]amino]phenyl]-3,5-difluorobenzenepropanoic acid;
3-[[3-[(4,5-dihydro-1H-imidazol-2-yl)amino]phenyl]methoxy]-β-phenylbenzenepropanoic acid;
sodium β-[3-[[[3-[(aminoiminomethyl)amino]phenyl]sulfonyl]amino]phenyl]-2-hydroxybenzenepropanoate;
ethyl 3-[[[3-[amino(hydroxyimino)methyl]phenyl]carbonyl]amino]benzeneacetate;
3-[[[3-(aminoiminomethyl)phenyl]carbonyl]amino]benzeneacetic acid;
3-[2-[[[3-[(aminoiminomethyl)amino]phenyl]carbonyl]amino]ethyl]benzeneacetic acid;
methyl 3-[[[[3-[(aminoiminomethyl)amino]phenyl]carbonyl]amino]methyl]benzeneacetate;
ethyl 3-[[[3-(aminoiminomethyl)phenyl]carbonyl]amino]benzeneacetate;
3-[[[3-[(aminoiminomethyl)amino]phenyl]carbonyl]amino]methyl]benzeneacetic acid;
3-[[[3-[(aminoiminomethyl)amino]phenyl]carbonyl]amino]benzeneacetic acid;
2-[3-[3-[(4,5-dihydro-1H-imidazol-2-yl)amino]phenyl]-1-oxo-2-propenyl]phenoxy]acetic acid;
2-[3-[3-[(aminoiminomethyl)amino]phenyl]-1-oxopropenyl]phenoxy]acetic acid;
[3-[[[[3-[(aminoiminomethyl)amino]phenyl]amino]carbonyl]amino]phenoxy]acetic acid;
3-[(aminoiminomethyl)amino]-N-[3-(3,4-dihydro-2-oxo-2H-benzopyran-4-yl)phenyl]benzenesulfonamide; and
3-[(4,5-dihydro-1H-imidazol-2-yl)amino]-N-[3-(3,4-dihydro-2-oxo-2H-benzopyran-4-yl)phenyl]benzenesulfonamide.

17. The method according to claim 15 wherein the condition treated is tumor metastasis.

18. The method according to claim 16 wherein the condition treated is tumor metastasis.

19. The method according to claim 15 wherein the condition treated is solid tumor growth.

20. The method according to claim 16 wherein the condition treated is solid tumor growth.

21. The method according to claim 15 wherein the condition treated is angiogenesis.

22. The method according to claim 16 wherein the condition treated is angiogenesis.

23. The method according to claim 15 wherein the condition treated is osteoporosis.

24. The method according to claim 16 wherein the condition treated is osteoporosis.

25. The method according to claim 15 wherein the condition treated is humoral hypercalcemia of malignancy.

26. The method according to claim 16 wherein the condition treated is humoral hypercalcemia of malignancy.

27. The method according to claim 15 wherein the condition treated is smooth muscle cell migration.

28. The method according to claim 16 wherein the condition treated is smooth muscle cell migration.

29. The method according to claim 15 wherein restenosis is inhibited.

30. The method according to claim 16 wherein restenosis is inhibited.

* * * * *